(12) United States Patent
Soula et al.

(10) Patent No.: US 9,700,599 B2
(45) Date of Patent: Jul. 11, 2017

(54) RAPID-ACTING INSULIN FORMULATION COMPRISING A SUBSTITUTED ANIONIC COMPOUND

(71) Applicant: ADOCIA, Lyons (FR)

(72) Inventors: Olivier Soula, Meyzieu (FR); Gérard Soula, Meyzieu (FR); Emmanuel Dauty, Lyons (FR); Richard Charvet, Rillieux-la-Pape (FR)

(73) Assignee: ADOCIA, Lyons (FR)

( * ) Notice: Subject to any disclaimer, the term of this patent is extended or adjusted under 35 U.S.C. 154(b) by 338 days.

(21) Appl. No.: 14/079,516

(22) Filed: Nov. 13, 2013

(65) Prior Publication Data

US 2014/0142034 A1    May 22, 2014
US 2014/0378373 A2    Dec. 25, 2014

Related U.S. Application Data

(60) Provisional application No. 61/726,349, filed on Nov. 14, 2012, provisional application No. 61/725,775, filed on Nov. 13, 2012.

(30) Foreign Application Priority Data

Nov. 13, 2012  (FR) .................................... 12 60808
Nov. 14, 2012  (FR) .................................... 12 60855

(51) Int. Cl.
| | | |
|---|---|---|
| A61K 38/28 | (2006.01) | |
| A61K 9/00 | (2006.01) | |
| A61K 47/26 | (2006.01) | |
| A61K 47/36 | (2006.01) | |
| A61K 47/02 | (2006.01) | |
| A61K 47/12 | (2006.01) | |
| A61K 47/34 | (2017.01) | |
| C07K 5/00 | (2006.01) | |

(52) U.S. Cl.
CPC ............ *A61K 38/28* (2013.01); *A61K 9/0019* (2013.01); *A61K 47/02* (2013.01); *A61K 47/12* (2013.01); *A61K 47/26* (2013.01); *A61K 47/34* (2013.01); *A61K 47/36* (2013.01); *C07K 5/00* (2013.01)

(58) Field of Classification Search
None
See application file for complete search history.

(56) References Cited

U.S. PATENT DOCUMENTS

| | | |
|---|---|---|
| 2,387,201 A | 10/1945 | Weiner |
| 2,847,385 A | 8/1958 | Hiler |
| 4,006,059 A | 2/1977 | Butler |
| 4,011,137 A | 3/1977 | Thompson et al. |
| 4,126,628 A | 11/1978 | Paquet |
| 4,438,029 A | 3/1984 | Erickson et al. |
| 4,472,385 A | 9/1984 | Brange et al. |
| 4,826,818 A | 5/1989 | Mori et al. |
| 5,204,366 A | 4/1993 | Lavanish et al. |
| 5,310,937 A | 5/1994 | Lavanish et al. |
| 5,929,027 A | 7/1999 | Takama et al. |
| 6,991,798 B1 | 1/2006 | Gschneidner et al. |
| 8,241,620 B2 | 8/2012 | Dahri-Correia et al. |
| 9,089,476 B2 | 7/2015 | Soula et al. |
| 2004/0131583 A1 | 7/2004 | Barritault et al. |
| 2004/0234616 A1 | 11/2004 | Sabetsky |
| 2005/0175611 A1 | 8/2005 | Mahler et al. |
| 2007/0191757 A1 | 8/2007 | Steiner et al. |
| 2007/0235365 A1 | 10/2007 | Pohl et al. |
| 2008/0014250 A1 | 1/2008 | Soula et al. |
| 2008/0039365 A1 | 2/2008 | Steiner et al. |
| 2008/0039368 A1 | 2/2008 | Steiner et al. |
| 2008/0096800 A1 | 4/2008 | Pohl et al. |
| 2008/0234227 A1 | 9/2008 | Soula et al. |
| 2009/0048412 A1 | 2/2009 | Soula et al. |
| 2009/0221805 A1 | 9/2009 | Dahri-Correia et al. |
| 2009/0291114 A1 | 11/2009 | Soula et al. |
| 2010/0137456 A1 | 6/2010 | Soula et al. |
| 2010/0166867 A1 | 7/2010 | Soula et al. |
| 2010/0167991 A1 | 7/2010 | Soula et al. |

(Continued)

FOREIGN PATENT DOCUMENTS

| | | |
|---|---|---|
| CN | 1613862 A | 5/2005 |
| CN | 101835493 A | 9/2010 |

(Continued)

OTHER PUBLICATIONS

Giger, Katie et al., "Suppression of Insulin Aggregation by Heparin," Biomacromolecules, 2008, vol. 9, pp. 2338-2344.

Lou, Xianwen et al., "Simulation of size exclusion chromatography for characterization of supramolecular complex: a theoretical study," Journal of Chromatography A, 2004, vol. 1029, pp. 67-75.

Tschantz, William R. et al., "Substrate Binding Is Required for Release of Product from Mammalian Protein Farnesyltransferase," The Journal of Biological Chemistry, 1997, vol. 272, No. 15, pp. 9989-9993.

Oct. 14, 2009 Search Report issued in French Patent Application No. 723351.

Jul. 12, 2010 Written Opinion issued in International Patent Application No. PCT/IB2010/000711.

(Continued)

*Primary Examiner* — Eric Olson
*Assistant Examiner* — Dale R Miller
(74) *Attorney, Agent, or Firm* — Oliff PLC

(57) ABSTRACT

The invention relates to a composition in aqueous solution, including insulin and at least one substituted anionic compound chosen from substituted anionic compounds consisting of a backbone formed from a discrete number u of between 1 and 8 (1≤u≤8) of identical or different saccharide units, linked via identical or different glycoside bonds, said saccharide units being chosen from the group consisting of hexoses, in cyclic form or in open reduced form, said compound comprising partially substituted carboxyl functional groups, the unsubstituted carboxyl functional groups being salifiable. The invention also relates to a pharmaceutical formulation comprising a composition as claimed in any one of the preceding claims.

14 Claims, 10 Drawing Sheets

(56) References Cited

U.S. PATENT DOCUMENTS

Figure 1:
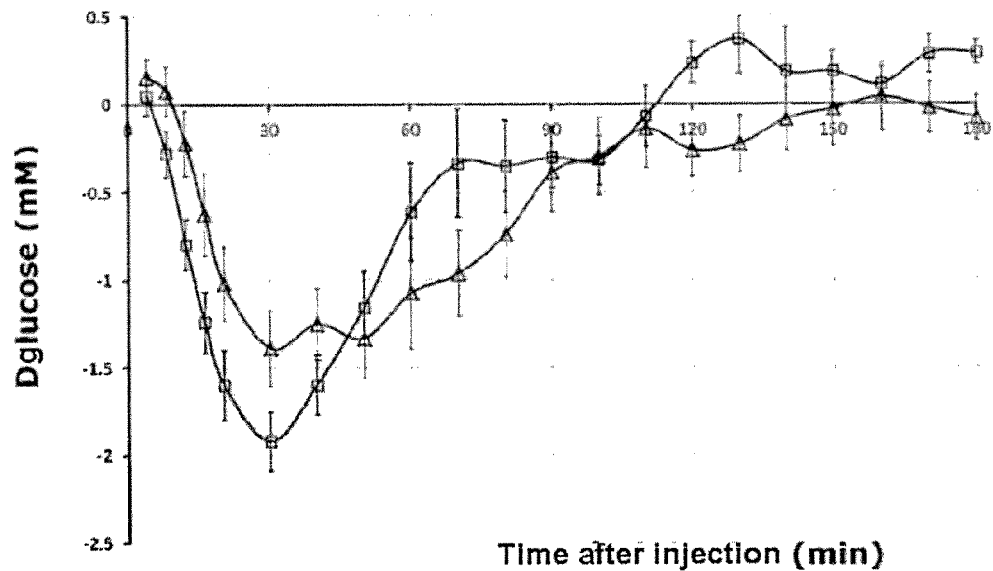

| | | | |
|---|---|---|---|
| 2010/0184965 A1 | 7/2010 | Soula et al. | |
| 2010/0227795 A1 | 9/2010 | Steiner et al. | |
| 2010/0249020 A1 | 9/2010 | Soula et al. | |
| 2011/0014189 A1 | 1/2011 | Soula et al. | |
| 2011/0159068 A1 | 6/2011 | Soula et al. | |
| 2011/0172166 A1 | 7/2011 | Charvet et al. | |
| 2011/0195025 A1* | 8/2011 | Kett | C07H 3/06 424/9.1 |
| 2011/0195913 A1 | 8/2011 | Charvet et al. | |
| 2011/0212901 A1 | 9/2011 | Akiyoshi et al. | |
| 2011/0244530 A1 | 10/2011 | Toda et al. | |
| 2011/0250653 A1 | 10/2011 | Toda et al. | |
| 2011/0318429 A1 | 12/2011 | Ko | |
| 2012/0041079 A1 | 2/2012 | Soula et al. | |
| 2012/0094902 A1 | 4/2012 | Soula et al. | |
| 2012/0178675 A1* | 7/2012 | Pohl | A61K 9/0019 514/6.4 |
| 2012/0295833 A1 | 11/2012 | Charvet et al. | |
| 2012/0309680 A1 | 12/2012 | Charvet et al. | |
| 2013/0231281 A1 | 9/2013 | Soula et al. | |
| 2014/0142034 A1 | 5/2014 | Soula et al. | |
| 2014/0378373 A2 | 12/2014 | Soula et al. | |

FOREIGN PATENT DOCUMENTS

| | | |
|---|---|---|
| CN | 101920019 A | 12/2010 |
| CN | 102300586 A | 12/2011 |
| DE | 103 55 251 A1 | 6/2005 |
| EP | 0 093 551 A2 | 11/1983 |
| EP | 0 190 041 A2 | 8/1986 |
| EP | 0 214 826 A2 | 3/1987 |
| EP | 0 441 563 A2 | 8/1991 |
| EP | 0608445 A1 | 8/1994 |
| EP | 0 648 495 A2 | 4/1995 |
| EP | 0 681 833 A2 | 11/1995 |
| EP | 0 700 683 A1 | 3/1996 |
| EP | 0 787 497 A2 | 8/1997 |
| EP | 1 623 979 A1 | 2/2006 |
| EP | 2 319 500 A1 | 5/2011 |
| EP | 2711077 A1 | 3/2014 |
| FR | 2 224 164 A1 | 10/1974 |
| FR | 2 914 305 A1 | 10/2008 |
| FR | 2 936 800 A1 | 4/2010 |
| FR | 2 943 538 A1 | 10/2010 |
| FR | 2 980 796 A1 | 4/2013 |
| JP | S47-22571 B | 11/1972 |
| JP | S61-12899 B2 | 4/1986 |
| JP | H03-153653 A | 7/1991 |
| JP | H07-82225 A | 3/1995 |
| JP | 2007/177182 A | 7/2007 |
| JP | 2007/177185 A | 7/2007 |
| JP | 2015/010075 A | 1/2015 |
| PL | 149145 B1 | 1/1990 |
| PT | 103003 A | 2/2005 |
| RU | 94026279 A | 6/1996 |
| WO | 88/06599 A1 | 9/1988 |
| WO | 90/10645 A1 | 9/1990 |
| WO | 91/09617 A1 | 7/1991 |
| WO | 96/33699 A1 | 10/1996 |
| WO | 97/49386 A1 | 12/1997 |
| WO | 99/34821 A1 | 7/1999 |
| WO | 00/64845 A1 | 11/2000 |
| WO | 02/20466 A1 | 3/2002 |
| WO | 02/053190 A2 | 7/2002 |
| WO | 03/000202 A2 | 1/2003 |
| WO | 03/014371 A1 | 2/2003 |
| WO | 03/057650 A2 | 7/2003 |
| WO | 2004/050620 A2 | 6/2004 |
| WO | 2004/093833 A2 | 11/2004 |
| WO | 2005/072803 A1 | 8/2005 |
| WO | 2005/089722 A1 | 9/2005 |
| WO | 2007/038773 A1 | 4/2007 |
| WO | 2007/041481 A1 | 4/2007 |
| WO | 2007/074456 A2 | 7/2007 |
| WO | 2007/116143 A1 | 10/2007 |
| WO | 2007/121256 A2 | 10/2007 |
| WO | 2008/038111 A1 | 4/2008 |
| WO | 2008/062466 A2 | 5/2008 |
| WO | 2008/084237 A2 | 7/2008 |
| WO | 2008/124522 A2 | 10/2008 |
| WO | 2008/152106 A1 | 12/2008 |
| WO | 2009/048945 A1 | 4/2009 |
| WO | 2009/048959 A1 | 4/2009 |
| WO | 2009/106386 A1 | 9/2009 |
| WO | 2009/127940 A1 | 10/2009 |
| WO | 2009/136500 A1 | 11/2009 |
| WO | 2010/018324 A1 | 2/2010 |
| WO | 2010/028055 A1 | 3/2010 |
| WO | 2010/041119 A1 | 4/2010 |
| WO | 2010/041138 A2 | 4/2010 |
| WO | 2010/053140 A1 | 5/2010 |
| WO | 2010/058106 A1 | 5/2010 |
| WO | 2010/067613 A1 | 6/2010 |
| WO | 2010/102020 A1 | 9/2010 |
| WO | WO 2010/122385 A1 | 10/2010 |
| WO | 2010/149772 A1 | 12/2010 |
| WO | 2011/077405 A1 | 6/2011 |
| WO | 2011/098962 A2 | 8/2011 |
| WO | 2012/002450 A1 | 1/2012 |
| WO | 2012/078760 A1 | 6/2012 |
| WO | 2012/124513 A1 | 9/2012 |
| WO | 2012/153070 A1 | 11/2012 |
| WO | 2012/153071 A2 | 11/2012 |
| WO | 2012/157656 A1 | 11/2012 |
| WO | 2013/021143 A1 | 2/2013 |
| WO | WO 2013/064787 A1 | 5/2013 |
| WO | 2014/076423 A1 | 5/2014 |

OTHER PUBLICATIONS

Jul. 12, 2010 Search Report issued in International Patent Application No. PCT/IB2010/000711.

Sep. 19, 2012 Office Action issued in U.S. Appl. No. 12/662,036.

Arranz et al., "Water-insoluble dextrans by grafting, 3a) Reaction of dextran with butyl isocyanate. Chemical hydrolysis," Makromol. Chem., vol. 188, pp. 2831-2838, 1987.

Carpino et al., "Efficiency in Peptide Coupling: 1-Hydroxy-7-azabenzotriazole vs 3,4-Dihydro-3-hydroxy-4-oxo-1,2,3-benzotriazine," Journal of Organic Chemistry, vol. 60, pp. 3561-3564, 1995.

Caulfield et al., "The Permeability of Glomerular Capillaries to Graded Dextrans," The Journal of Cell Biology, vol. 63, pp. 883-903, 1974.

Chang et al., "Permselectivity of the glomerular capillary wall: III. Restricted transport of polyanions," Kidney International, vol. 8, pp. 212-218, 1975.

Demitras et al, Inorganic Chemistry, Prentice-Hall International Inc., 1972, enclosed pp. 1-5.

Engelmann et al., "Preparation of Starch Carbamates in Homogeneous Phase using Different Mixing Conditions," Starch/Stärke, 2001, pp. 560-569, vol. 53, Wiley-VCH Verlag GmbH.

Larsen, "Dextran prodrugs—structure and stability in relation to therapeutic activity," Advanced Drug Delivery Reviews, 1989, pp. 103-154, vol. 3, Elsevier.

Ouari et al., "Synthesis of a Glycolipidic Amphiphilic Nitrone as a New Spin Trap," J. Org. Chem., 1999, pp. 3554-3556, vol. 64, American Chemical Society (with 10 pages of supporting information).

Shen et al., "Synthesis and Characterization of Cellulose Carbamates Having alpha-Amino Acid Moieties," Polymer Bulletin, 2005, pp. 317-322, vol. 55.

Tsai et al., "Synthesis of Amino Acid Ester Isocyanates: Methyl (S)-2-Isocyanato-3-Phenylpropanoate [Benzenepropanoic acid, alpha-isocyanato-, methyl ester, (S)]," Organic Syntheses Coll., vol. 10, p. 544, 2004; vol. 78, p. 220, 2002.

Won, "Synthesis of heterobifunctional poly(ethylene glycol) containing an acryloyl group at one end and an isocyanate group at the other end," Polymer Bulletin, 2004, pp. 109-115, vol. 52.

(56) References Cited

OTHER PUBLICATIONS

Definition of Phenylalanine, from Croatian English Chemistry Dictionary & Glossary (http://glossary.periodni.com/glossary.php?en=phenylalanine, enclosed, pp. 1-2, Accessed Jan. 17, 2013.
May 3, 2012 French Search Report issued in French Patent Application No. 1158885.
Feb. 22, 2013 Office Action issued in U.S. Appl. No. 12/662,036.
Feb. 28, 2013 Office Action issued in U.S. Appl. No. 13/468,799.
U.S. Appl. No. 12/662,036 to Soula et al., filed Mar. 29, 2010.
U.S. Appl. No. 13/287,793 to Soula et al., filed Nov. 2, 2011.
U.S. Appl. No. 13/468,799 to Charvet et al., filed May 10, 2012.
U.S. Appl. No. 13/468,849 to Charvet et al., filed Jul. 11, 2012.
Heinze et al.; "Functional Polymers Based on Dextran;" Adv. Polym. Sci.; 2006; pp. 199-291; vol. 205; Springer-Verlag Berlin Heidelberg.
May 28, 2014 Office Action issued in U.S. Appl. No. 13/468,849.
Jul. 24, 2013 Office Action issued in U.S. Appl. No. 12/662,036.
R. Janowski, et al., "Two Polymorphs of a Covalent Complex Between Papain and a Diazomethylketone Inhibitor," J. Peptide Res. 64, 2004, pp. 141-150.
Apr. 2, 2013 International Search Report issued in PCT/FR2012/052543.
Jun. 25, 2014 Office Action issued in U.S. Appl. No. 13/668,000.
Definition of derivative and analog, from http://cancerweb.ncl.ac.uk/omd/about.html, pp. 1-5, accessed Jul. 7, 2005.
Polymer Molecular Weight Distribution and Definitions of MW Averages, from www.agilent.com/chem, pp. 1-4, Jun. 10, 2011.
Dec. 12, 2011 French Search Report issued in French Patent Application No. 1154039.
Rudd, Pauline M. et al., "Glycoforms modify the dynamic stability and functional activity of an enzyme." Biochemistry (1994) 33 p. 17-22.
MEMO, Myriad-Mayo guidance, Mar. 2014.
BOVINE ribonuclease b sequence (protein data bank, accession No. 1RBJ_, upload Oct. 10, 2012).
Solomons, T.W. Graham; Organic Chemistry, 4th editon, (1988) ISBN 0-471-83659-1, p. 751.
Heinze, Thomas et al.; "Functional Polymers based on dextran." Adv. Polym. Sci. (2006) 205 p. 199-291.
Roussel et al., "Monolayer lipid membrane-forming dissymmetrical bolaamphiphiles derived from alginate oligosaccharides;" Chem. Communication; 2006; pp. 3622-3624.
Watanabe et al., "Synthesis of lipid A type carboxymethyl derivatives with ether chains instead of ester chains and their LPS-antagonistic activities;" Carbohydrate Research; 2003; pp. 47-54; vol. 338.
Song et al., "6-o-Amino-2-o-carboxymethyl Glucopyranoside as Novel Glycoaminoxy Acid Building Block for the Construction of Oligosaccharide Mimetics;" Synthesis; 2011; pp. 2761-2766; No. 17.
Tareq et al., "Ieodoglucomides A and B from a Marine-Derived Bacterium Bacillus lichentiformis;" Organic Letters; 2012; pp. 1464-1467; vol. 14, No. 6.
Pal et al., "Molecular mechanism of physical gelation of hydrocarbons by fatty acid amides of natural amino acids," Tetrahedron; 2007; pp. 7334-7348; vol. 63.
Bhaskar et al., "The Selective Silylation of d-Mannitol Assisted by Phenylboronic Acid and the Solid State and Solution Structures of the Intermediate 1,6-bis(silyl) bis(phenylboronates);" Journal of Carbohydrate Chemistry; 2003; pp. 867-879; vol. 22, 9.
Edwards et al., "Dispiroketals in Synthesis (Part 18): Regioselective and Enantioselective Protection of Symmetric Polyol Substrates Using an Enantiopure (2S,2S)-Dimethyl-bis-dihydropyran;" Synlett; 1995; pp. 898-900; vol. 9.
Ruiz-Pena et al., "Physico-chemical studies of molecular interactions between non-ionic surfactants and bovine serum albumin;" Colloids and Surfaces B: Biointerfaces: 2010; pp. 282-289; vol. 75.
Sawardeker, Jawahar S. et al., "Quantitative determination of monosaccharides as their alditol acetates by gas liquid chromatography." Anal. Chem. (1965) 37 (12) p. 1602-1604.

Class notes for physical chemistry form the Univesity of Washington http://www.ocean.washington.edu/courses/oc400/Lecture_Notes/CHPT6.pdf, Oct. 2004.
Granger, Elisabeth et al., "Simplified syntheses of complex multifunctional nanomaterials." Chem. Communication (2008) 4792-4794.
Oct. 15, 2014 Office Action issued in U.S. Appl. No. 14/079,437.
May 21, 2015 Office Action issued in U.S. Appl. No. 14/079,437.
U.S. Appl. No. 14/079,437, filed Nov. 13, 2013 in the name of Soula et al.
U.S. Appl. No. 14/581,239, filed Dec. 23, 2014 in the name of Soula et al.
Dec. 18, 2015 Office Action issued in U.S. Appl. No. 14/079,437.
Wagner, Herman L., "The Mark-Houwink-Sakurada equation for the viscosity of linear polyethylene." J. Phys. Chem. Ref. Data (1985) 14(2) p. 611-617.
Wayne, Richard P., Principles and applications of photochemistry (1988) ISBN 0-19-855234-3.
Shimadzu scientific publication SC-AP-GC-0138, downloaded Dec. 1, 2015.
Jan. 22, 2016 Office Action issued in U.S. Appl. No. 14/581,239.
Brange et al.; "Insulin analogs with improved pharmacokinetic profiles;" Advanced Drug Delivery Reviews; 1999; pp. 307-335; vol. 35.
Baudys et al.; "Extending Insulin Action in Vivo by Conjugation to Carboxymethyl Dextran;" Bioconjugate Chem.; 1998; pp. 176-183; vol. 9.
Huus et al.; "Thermal Dissociation and Unfolding of Insulin;" Biochemistry; 2005; pp. 11171-11177; vol. 44.
Uversky et al.; Predication of the Association State of Insulin Using Spectral Parameters; Journal of Pharmaceutical Sciences; Apr. 2003; pp. 847-858; vol. 92, No. 4.
Smoot et al.; "Oligosaccharide Synthesis: From Conventional Methods to Modern Expeditious Strategies;" Advances in Carbohydrate Chemistry and Biochemistry; 2009;pp. 161-250; vol. 62.
Lindhorst; O-Glycoside synthesis; Essentials of Carbohydrate Chemistry and Biochemistry; 2007; pp. 157-208.
Apr. 27, 2016 Office Action issued in Chinese Application No. 201380059092.4.
Yalpani, Manssur et al., "Selective Chemical Modifications of Dextran", Journal of Polymer Science, 1985, vol. 23, pp. 1395-1405.
Cho, Byung Tae et al., "Direct and indirect reductive amination of aldehydes and ketones with solid acid-activated sodium borohydride under solvent-free conditions", Tetrahedron, 2005, vol. 61, pp. 5725-5734.
Zhang, Tianhong et al., "Novel Polysaccharide Surfactants: Synthesis of Model Compounds and Dextran-Based Surfactants", Macromolecules, 1994, vol. 27, pp. 7302-7308.
Takeoka, Shinji et al., "Physical properties and packing states of molecular assemblies of synthetic glycolipids in aqueous dispersions", Journal of the Chemical Society, Faraday Transactions, 1998, vol. 94, No. 15, pp. 2151-2158.
Sisu, Ioana et al., "Synthesis and structural characterization of amino-functionalized polysaccharides", Central European Journal of Chemistry, 2009, vol. 7, No. 1, pp. 66-73.
Kalra, Sanjay et al., "Ultra-fast acting insulin analogies", Recent Patents on Endocrine, Metabolic & Immune Drug Discovery, 2014, vol. 8-2, pp. 117-123.
May 17, 2016 Office Action Issued Un U.S. Appl. No. 14/711,378.
Nov. 15, 2016 International Preliminary Report on Patentability issued in International Application No. PCT/EP2015/060716.
Ramesh & Chandrasekaran, But-2-ynylbisoxycarbonyl Chloride: A Novel C2-Symmetric Reagent for the Protection of Amines and Amino Acids, Organic Letters, 2005, 7(22), 4947-4950.
Kartvelishvili et al, Amino acid based bioanalogous polymers. Synthesis of novel poly(urethane amide)s based on N, N'-(trimethylenedioxy-dicarbonyl)bis(phenylalanine), Macromolecular Chemistry and Physics, 1996, 197, 249-257.
Coker et al, "Pathways for the Decay of Organic Dichloramines and Liberation of Antimicrobial Chloramine Gases", Chemical Research in Toxicology, 2008, 21(12), 2334-2343.

(56) References Cited

OTHER PUBLICATIONS

Schuster et al, "Chymotryspin-catalyzed peptide synthesis in ice: use of unprotected amino acids as acyl acceptors", Tetrahedron Letters, 1993, 34(36), 5701-5702.
Votano et al, "Inhibition of deoxyhemoglobin S polymerization by biaromatic peptides found to associate with the hemoglobin molecule at a preferred site", Biochemistry, 1985, 24, 1966-1970.
Gorecki et al, "Peptide inhibitors of sickle hemoglobin aggregation: effect of hydrophobicity", Biochemistry, 1980, 19(8), 1564-1568.
Behe et al, "Quantitative assessment of the noncovalent inhibition of sickle hemoglobin gelation by phenyl derivatives and other known agents", Biochemistry, 1979, 18(19), 4196-4201.
Khosla et al, "Synthesis of mixed Na, N?-peptides of lysine through direct N?-peptidation", Journal of Scientific and Industrial Research, Section B: Physical Sciences, 1962, 21B, 318-321.
Liwschitz et al, The reaction of N-maleoylamino acids with benzylamine, Journal of the Chemical Society, 1962, 3726-3729.
Huffman et al, "Substrate specificity of isopenicillin N synthase", Journal of Medicinal Chemistry, 1992, 35, 1897-1914.
Swamy et al, "Synthesis of iron (III), cobalt (II), nickel (II), copper (II) and zinc (II) complexes with new quadridentate N, O-donor ligands", Oriental Journal of Chemistry, 2008, 24(3), 1103-1106.
Bergeron; "An investigation of the Impact of Molecular Geometry upon Microcapsule Self-Assembly", Journal of American Chemical Society, 1995, 117(25), 6658-65.
Coker et al, Supporting information for "Antimicrobial activity of chlorinated amino acids and peptides." Chemical Research in Toxicology, 2008, 21(12), 2334-2343.
Tse et al, "Translation of a DNA into a Library of 13000 Synthetic Small-Molecule Macrocycles Suitable for in Vitro Selection", Journal of the American Chemical Society, 2008, 130(46), 15611-15626.
Liu et al, "Ring opening polymerization of aliphatic cyclic carbonates in the presence of natural amino acids", Journal of Applied Polymer Science, 2008, 107(5), 3275-3279.
Gartner et al, "Multistep small-molecule synthesis programmed by DNA templates", Journal of the American Chemical Society, 2002, 124(35), 10304-10306.
Siddique & Duhamel, "Effect of Polypeptide Sequence on Polypeptide Self-Assembly", Langmuir, 2011, 27(11), 6639-6650.
Sun et al, "Homo-cysteinyl peptide inhibitors of the L1 metallo-β-lactamase, and SAR as determined by combinatorial library synthesis", Bioorganic Medicinal Chemistry Letters, 2006, 16(19), 5169-5175.
Hong et al, "Determination of inhibitory constants for CPA by competitive spectrophotometry", Peptides: Biology and Chemistry, Proceedings of the Chinese Peptide Symposium, 5th, Lanzhou, China, Jul. 14-17, 1998 (2000).
Humme, "Amino acid derivatives hydrolyzable by an enzyme of rennet. III. Peptides", Nederlands Melk-en Zuiveltijdschrift, 1971, 25(1), 3-14.
Fruchart et al, "A new linker fot the synthesis of C-terminal peptide-oxo-aldehydes," Tetrahedron Letters, 1999, 40, 6225-6228.
U.S. Statutory Invention Registration No. H645, published Jun. 6, 1989.
Siddique & Duhamel, Supporting Information for "Effect of Polypeptide Sequence on Polypeptide Self-Assembly", Langmuir, 2011, 27(11), 6639-6650.
Lodi et al, "Chiral aminoaci containing acyclic ligands. I. Syntheses and conformations", Tetrahedron, 1982, vol. 38, N° 14, pp. 2055-2060.
Marchelli et al, "Chiral aminoaci containing acyclic ligands. II. Compexation of alkaline earth cations", Tetrahedron, 1982, vol. 38, N°14, pp. 2061-2067.
Menzenski et al, "Self-assembly of supramolecular nanostructures from phenylalanine derived bolaamphiphiles", New Journal of Chemistry, 2007, vol. 31, pp. 1674-1680.
Jul. 22, 2016 Office Action Issued in U.S. Appl. No. 14/712,696.
Nov. 15, 2016 Search Report and Written Opinion issued in PCT Patent Application No. PCT/EP2015/060820.
Adediran, S.A. et al., "Deacylation Transition States of a Bacterial DD-Peptidase" Biochemistry, 45, 13074-13082 (2006).
Nov. 15, 2016 Search Report and Written Opinion issued in PCT Patent Application No. PCT/EP2015/060732.
Wu et al.; Reactive Impurities in Excipients: Profiling, Identification and Mitigation of Drug-Excipient Incompatibility; AAPS PharmSciTech; Dec. 2011; pp. 1249-1263; vol. 12, No. 4.
Gildersleeve et al.; Improved Procedure for Direct Coupling of Carbohydrates to Proteins via Reductive Amination; Bioconjug Chem.; Jul. 2008; pp. 1485-1490; vol. 19, No. 7.
U.S. Appl. No. 15/410,524, filed Jan. 19, 2017 in the name of Soula et al.
U.S. Appl. No. 14/711,378, filed May 13, 2015 in the name of Soula et al.
U.S. Appl. No. 14/712,696, filed May 14, 2015 in the name of Soula et al.
U.S. Appl. No. 15/353,522, filed Nov. 16, 2016 in the name of Soula et al.
"Chemical Book" (downloaded online on Jan. 17, 2017 from URL: <http://www.chemicalbook.com/ProductChemicalPropertiesCB7932982_EN.htm>).
ChEBI-70976 (downloaded online on Jan. 17, 2017 from URL: <http://www.ebi.ac.uk/chebi/searchld.do;isessionid=0C30621862A25C54A3A6EFBB1CFB84D0?chebild=CHEBI:70976>).
"Sigma-Aldrich L-tryptophan" (downloaded online on Jan. 18, 2017 from URL: <http:///www.sigmaaldrich.com/catalog/substance/ltrytophan204237322311?lang=en&region=US#>).
"Sigma-Aldrich L-tyrosine" (downloaded online on Jan. 18, 2017 from URL: <http://www.sigmaaldrich.com/catalog/substance/ltyrosine181196018411?lang=en&region=US>).
Mar. 7, 2017 Office Action issued in U.S. Appl. No. 14/711,378.
Mar. 1, 2017 Office Action issued in U.S. Appl. No. 14/712,328.
Feb. 8, 2017 Office Action issued in Chinese Application No. 201380059092.4.
March 16, 2017 European Office Action issued in European Patent Application No. 13 801 655.5.
Apr. 21, 2017 Office Action issued in Chinese Patent Application No. 201380059136.3.
Apr. 26, 2017 Office Action issued in Japanese Patent Application No. 2015-542338.
Apr. 27, 2017 Office Action issued in Eurasian Patent Application No. 201590937/28.

* cited by examiner

RAPID-ACTING INSULIN FORMULATION COMPRISING A SUBSTITUTED ANIONIC COMPOUND

The present invention relates to a rapid-acting insulin formulation.

Since the production of insulin by genetic engineering, at the start of the 1980s, diabetic patients have benefited from human insulin for their treatment. This product has greatly improved this therapy, since the immunological risks associated with the use of non-human insulin, in particular pig insulin, are eliminated. However, subcutaneously-injected human insulin has a hypoglycemiant effect only after 60 minutes, which means that diabetic patients treated with human insulin must take the injection 30 minutes before a meal.

One of the problems to be solved for improving the health and comfort of diabetic patients is that of providing them with insulin formulations which afford a faster hypoglycemiant response than that of human insulin, if possible a response approaching the physiological response of a healthy person. The secretion of endogenous insulin in a healthy individual is immediately triggered by the increase in glycemia. The object is to minimize the delay between the injection of insulin and the start of the meal.

At the present time, it is accepted that the provision of such formulations is useful in order for the patient to receive the best possible health care.

Genetic engineering has made it possible to afford a response with the development of rapid insulin analogs. These insulins are modified on one or two amino acids so as to be more rapidly absorbed into the blood compartment after a subcutaneous injection. These insulins lispro (Humalog®, Lilly), aspart (Novolog®, Novo) and glulisine (Apidra®, Sanofi Aventis) are stable insulin solutions with a faster hypoglycemiant response than that of human insulin. Consequently, patients treated with these rapid insulin analogs can take an insulin injection only 15 minutes before a meal.

The principle of rapid insulin analogs is to form hexamers at a concentration of 100 IU/mL to ensure the stability of the insulin in the commercial product while at the same time promoting very rapid dissociation of these hexamers into monomers after subcutaneous injection so as to obtain rapid action.

Human insulin as formulated in its commercial form does not make it possible to obtain a hypoglycemiant response close in kinetic terms to the physiological response generated by the start of a meal (increase in glycemia), since, at the working concentration (100 IU/mL), in the presence of zinc and other excipients such as phenol or m-cresol, it assembles to form a hexamer, whereas it is active in monomer and dimer form. Human insulin is prepared in the form of hexamers so as to be stable for up to 2 years at 4° C., since, in the form of monomers, it has a very high propensity to aggregate and then to fibrillate, which makes it lose its activity. Furthermore, in this aggregated form, it presents an immunological risk to the patient.

The dissociation of the hexamers into dimers and of the dimers into monomers delay its action by close to 20 minutes when compared with a rapid insulin analog (Brange J., et al., Advanced Drug Delivery Review, 35, 1999, 307-335).

In addition, the kinetics of passage of the insulin analogs into the blood and their glycemia reduction kinetics are not optimal, and there is a real need for a formulation which has an even shorter action time in order to come close to the kinetics of endogenous insulin secretion in healthy individuals.

The company Biodel has proposed a solution to this problem with a human insulin formulation comprising EDTA and citric acid as described in patent application US 200839365. The capacity of EDTA to complex zinc atoms and the interactions of citric acid with the cationic regions present at the surface of insulin are described as destabilizing the hexameric form of insulin and thus as reducing its action time.

However, such a formulation especially has the drawback of disassociating the hexameric form of insulin, which is the only stable form capable of meeting the stability requirements of the pharmaceutical regulations.

PCT patent application WO 2010/122385 in the name of the Applicant is also known, describing human insulin or insulin analog formulations that can solve the various problems mentioned above via the addition of a substituted polysaccharide comprising carboxyl groups.

However, the requirements entailed by the chronic and intensive use or even the pediatric use of such formulations lead a person skilled in the art to seek to use excipients whose molar mass and size are as small as possible in order to facilitate their elimination.

The polysaccharides described in patent applications WO 2010/122385A1 and US 2012/094902A1 as excipients are compounds consisting of chains whose lengths are statistically variable and which are very rich in possible sites of interaction with protein active principles. This richness might induce a lack of specificity in terms of interaction, and a smaller and better defined molecule might make it possible to be more specific in this respect.

In addition, a molecule with a well-defined backbone is generally more easily traceable (for example MS/MS) in biological media during pharmacokinetic or ADME (administration, distribution, metabolism, elimination) experiments when compared with a polymer which generally gives a very diffuse and noisy signal in mass spectrometry.

Conversely, it is not excluded that a well-defined and shorter molecule might have a deficit of possible sites of interaction with protein active principles. Specifically, on account of their reduced size, they do not have the same properties as polymers of polysaccharide type since there is loss of the polymer effect, as is demonstrated in the comparative examples of the experimental section; see especially the tests of insulin dissolution at the isoelectric point and the tests of interaction with a model protein such as albumin.

Despite these discouraging results, the Applicant has succeeded in developing formulations that are capable of accelerating insulin by using a substituted anionic compound in combination with a polyanionic compound.

Furthermore, as in the case of the use of polysaccharides, the hexameric nature of insulin is not affected, and thus the stability of the formulations is not affected, as is moreover confirmed by the examples of state of association of human insulin and insulin analog via circular dichroism in the presence of a substituted anionic compound according to the invention.

The present invention makes it possible to solve the various problems outlined above since it makes it possible especially to prepare a human insulin or insulin analog formulation, which is capable, after administration, of accelerating the passage of the human insulin or of analogs thereof into the blood and of more quickly reducing glycemia when compared with the corresponding commercial insulin products.

Following is a brief description of the drawings.

FIG. 1: DGlucose (mM) as a function of time after injection (min.). Curve plotted with the squares corresponding to example B8, glucose Tmin=30±11 min, curve plotted with the triangles corresponding to example B2, glucose Tmin=44±14 min.

Figure 2:
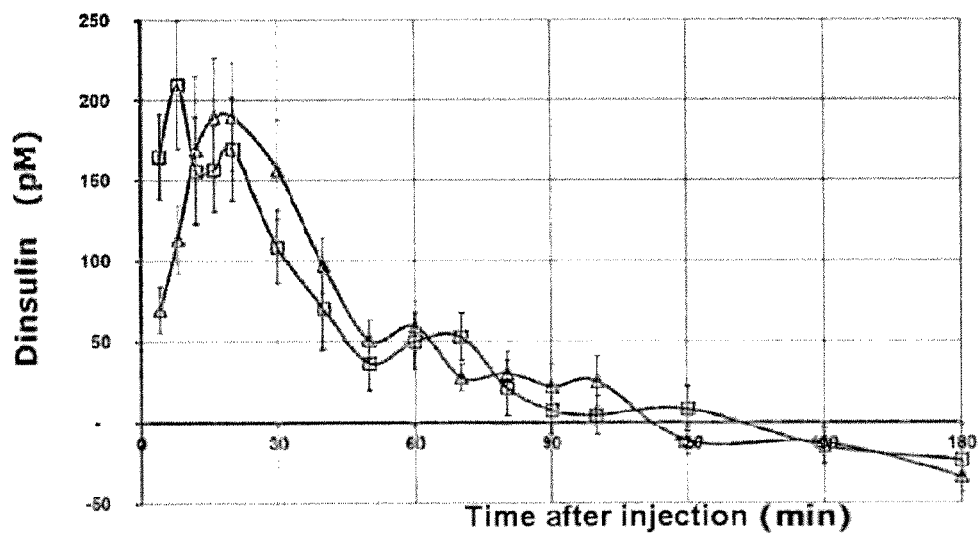

FIG. 2: DInsulin (pM) as a function of time after injection (min.). Curve plotted with the squares corresponding to example B8, insulin Tmax=11±6 min, curve plotted with the triangles corresponding to example B2, insulin Tmax=18±8 min.

Figure 3:
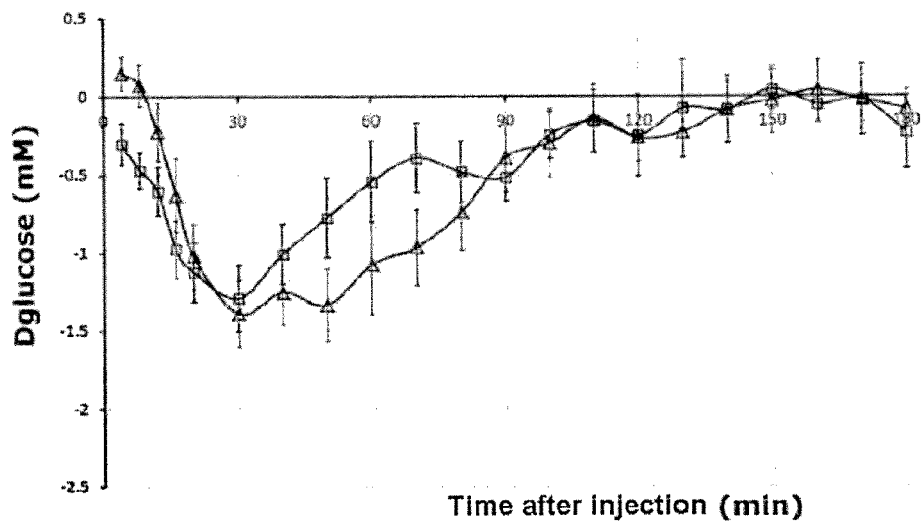

FIG. 3: DGlucose (mM) as a function of time after injection (min.). Curve plotted with the squares corresponding to example B10, glucose Tmin=33±13 min, curve plotted with the triangles corresponding to example B2, glucose Tmin=44±14 min.

Figure 4:
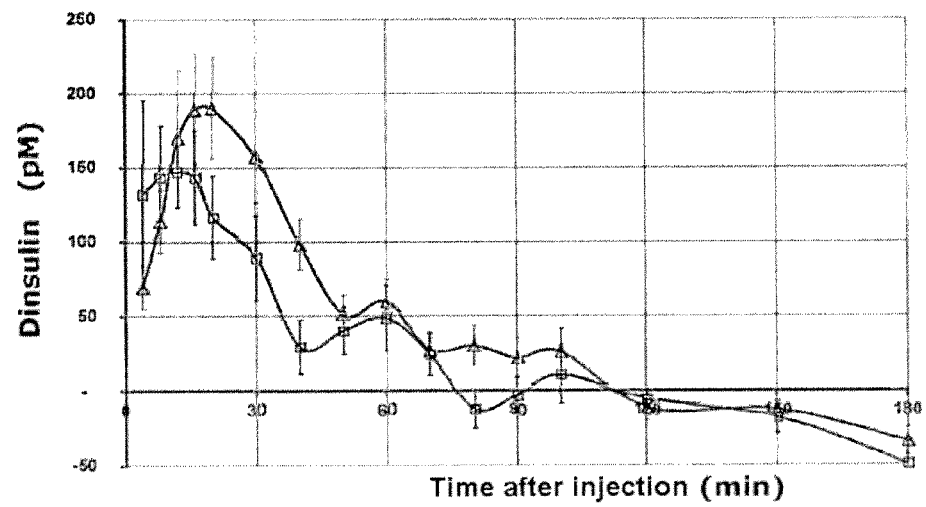

FIG. 4: DInsulin (pM) as a function of time after injection (min.). Curve plotted with the squares corresponding to example B10, insulin Tmax=15±9 min, curve plotted with the triangles corresponding to example B2, insulin Tmax=18±8 min.

Figure 5:
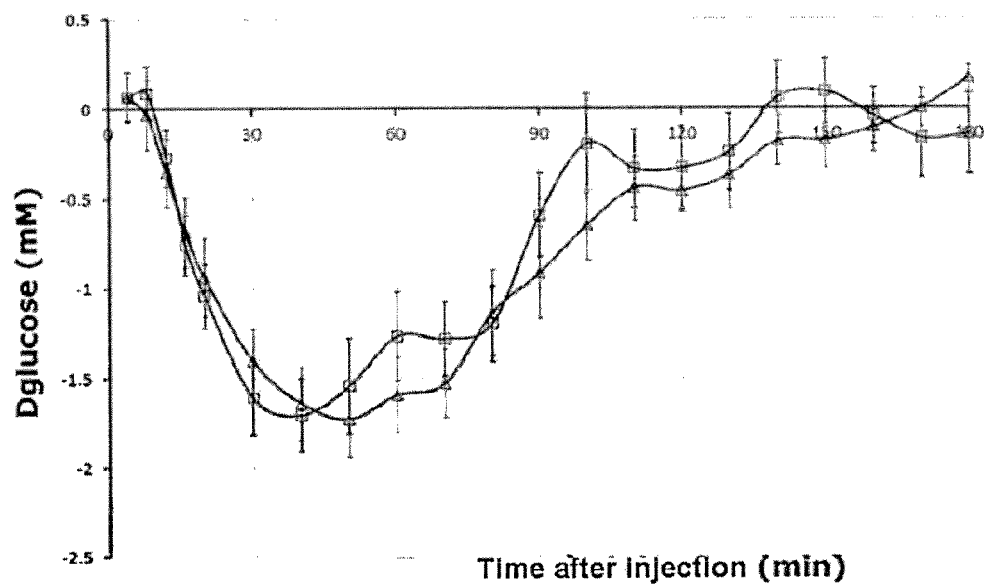

FIG. 5: DGlucose (mM) as a function of time after injection (min.). Curve plotted with the squares corresponding to example B7, glucose Tmin=41±16 min, curve plotted with the triangles corresponding to example B2, glucose Tmin=50±14 min.

Figure 6:
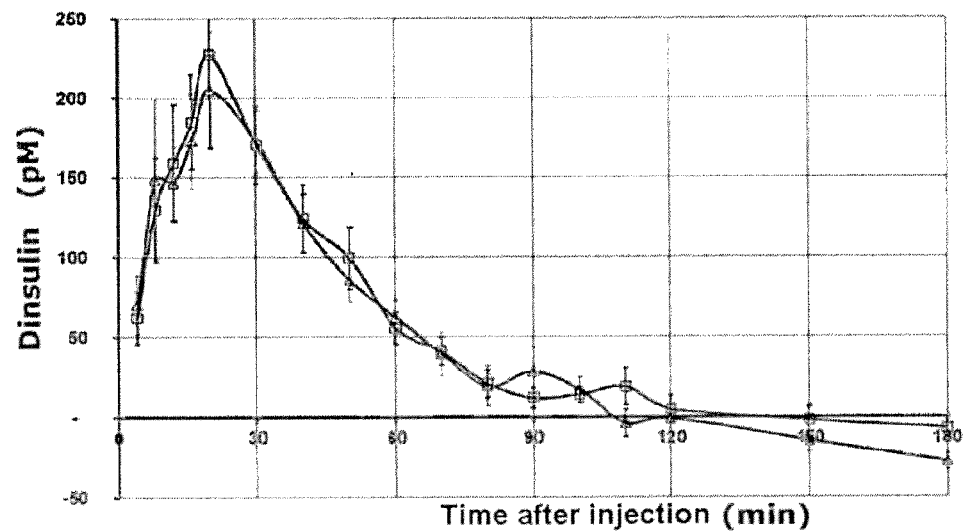

FIG. 6: DInsulin (pM) as a function of time after injection (min.). Curve plotted with the squares corresponding to example B2, insulin Tmax=21±10 min, curve plotted with the triangles corresponding to example B2, insulin Tmax=20±9 min.

Figure 7:
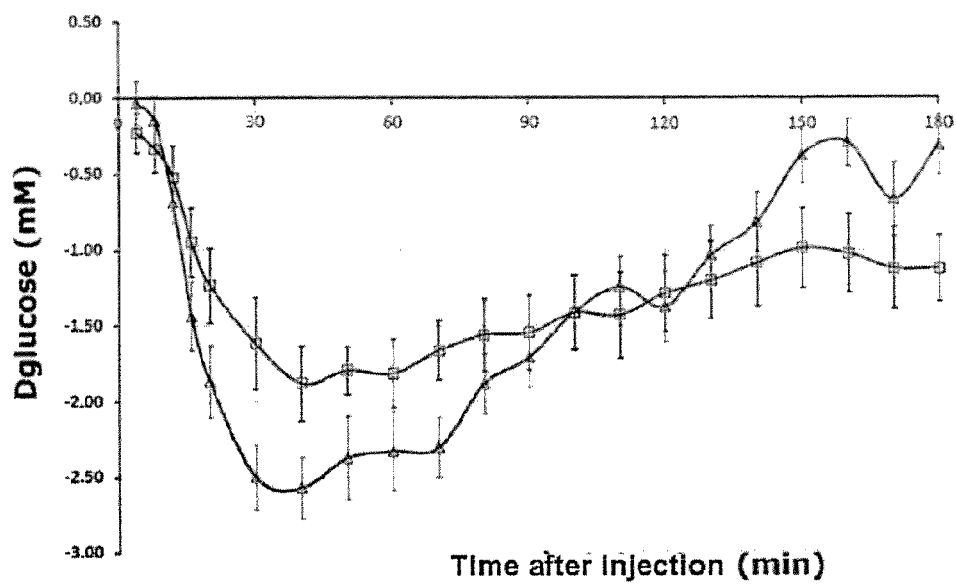

FIG. 7: DGlucose (mM) as a function of time after injection (min.). Curve plotted with the squares corresponding to example B3, glucose Tmin=61±31 min, curve plotted with the triangles corresponding to example B1, glucose Tmin=44±13 min.

Figure 8:
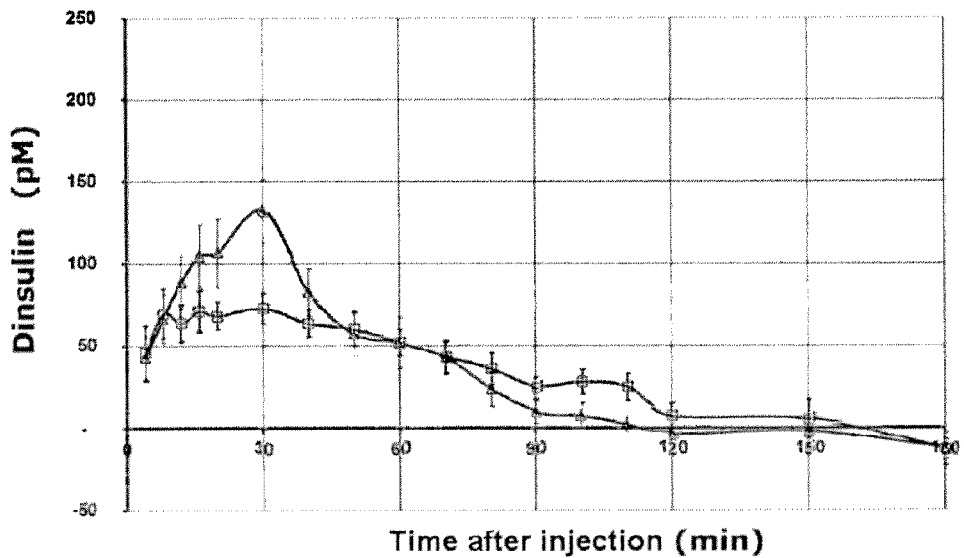

FIG. 8: DInsulin (pM) as a function of time after injection (min.). Curve plotted with the squares corresponding to example B3, insulin Tmax=36±33 min, curve plotted with the triangles corresponding to example B1, insulin Tmax=28±13 min.

Figure 9:
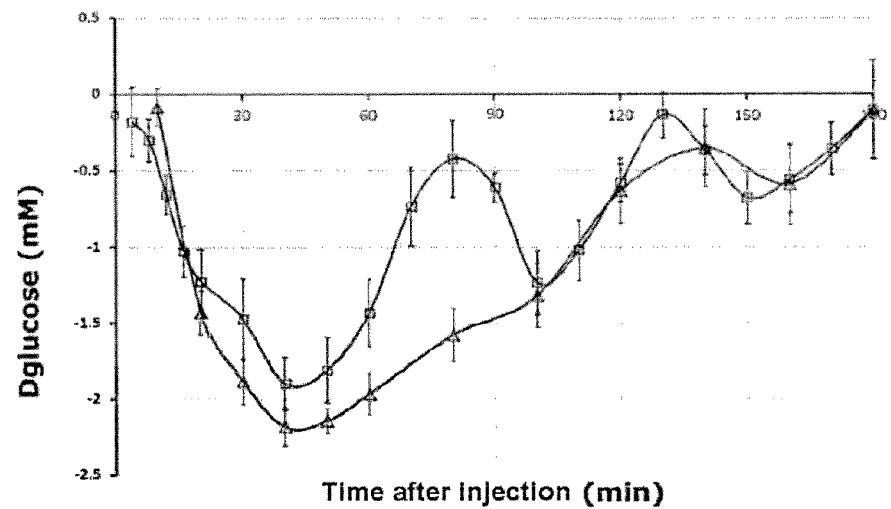

FIG. 9: DGlucose (mM) as a function of time after injection (min.). Curve plotted with the squares corresponding to example B39, glucose Tmin=46±9 min, curve plotted with the triangles corresponding to example B1, glucose Tmin=53±24 min.

Figure 10:
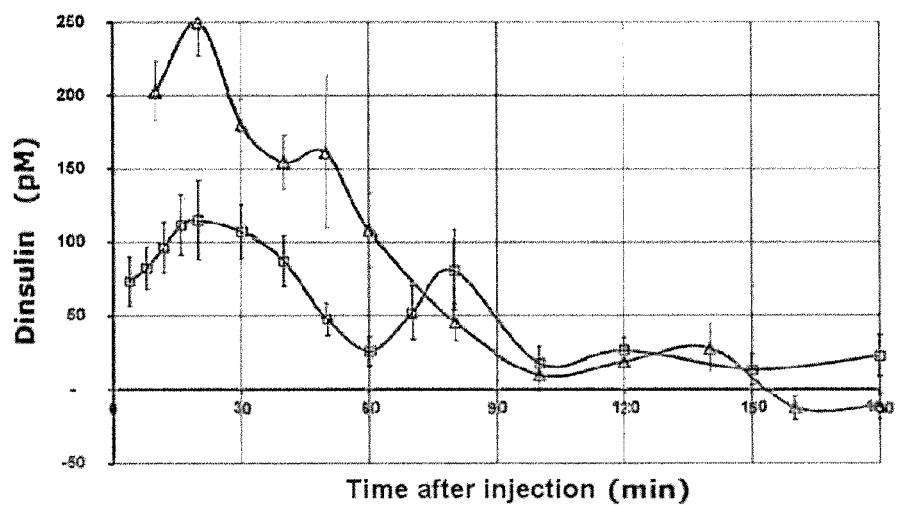

FIG. 10: DInsulin (pM) as a function of time after injection (min.). Curve plotted with the squares corresponding to example B39, insulin Tmax=20±7 min, curve plotted with the triangles corresponding to example B1, insulin Tmax=22±10 min.

Figure 11:
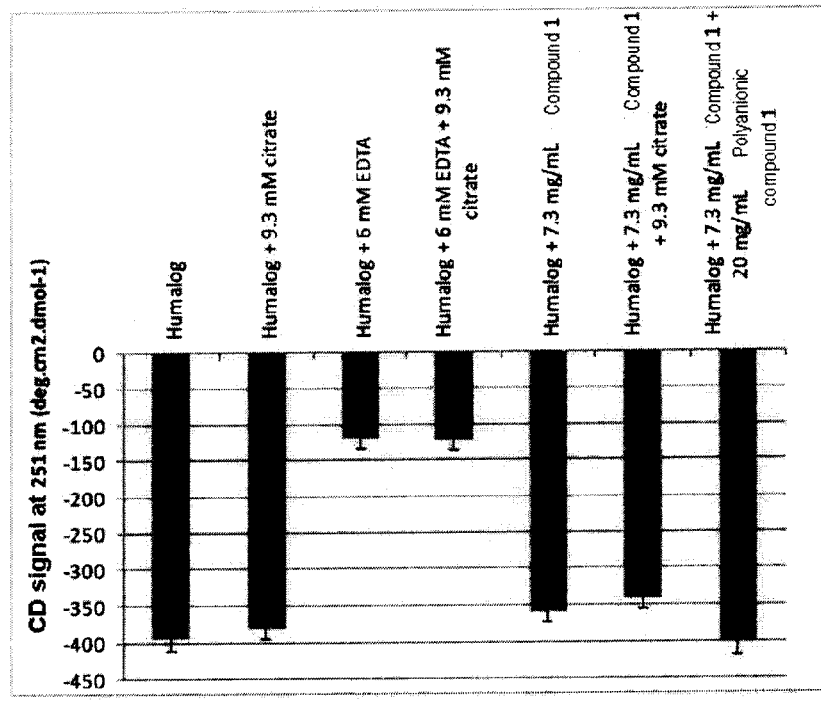

FIG. 11 describes on the x-axis, from left to right:
Humalog
Humalog+9.3 mM citrate
Humalog+6 mM EDTA
Humalog+6 mM EDTA+9.3 mM citrate
Humalog+7.3 mg/ml Compound 1
Humalog+7.3 mg/ml Compound 1+9.3 mM citrate
Humalog+7.3 mg/ml Compound 1+20 mg/ml Polyanionic compound 1 and on the y-axis the CD signal at 251 nm (deg·cm$^2$·dmol$^{-1}$).

Figure 12:
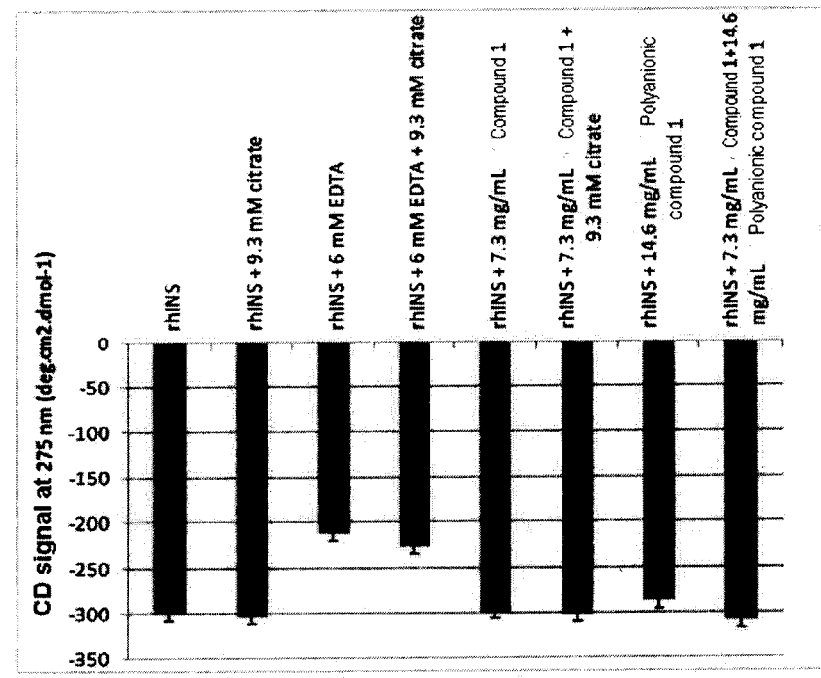

FIG. 12 describes on the x-axis, from left to right:
rhINS
rhINS+9.3 mM citrate
rhINS+6 mM EDTA
rhINS+6 mM EDTA+9.3 mM citrate
rhINS+7.3 mg/ml Compound 1
rhINS+7.3 mg/ml Compound 1+9.3 mM citrate
rhINS+7.3 mg/ml Compound 1+20 mg/ml Polyanionic compound 1
and on the y-axis the CD signal at 275 nm (deg·cm$^2$·dmol$^{-1}$).

Figure 13:
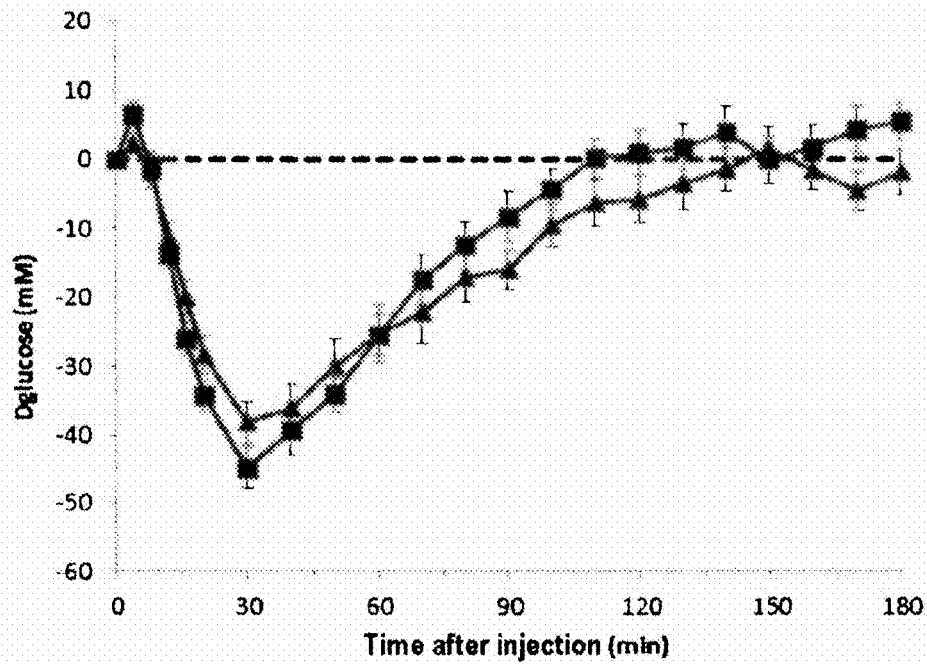

FIG. 13: DGlucose (mM) as a function of time after injection (min.). Curve plotted with the squares corresponding to example B11, glucose Tmin=32±10 min, curve plotted with the triangles corresponding to example B2, glucose Tmin=41±21 min.

Figure 14:
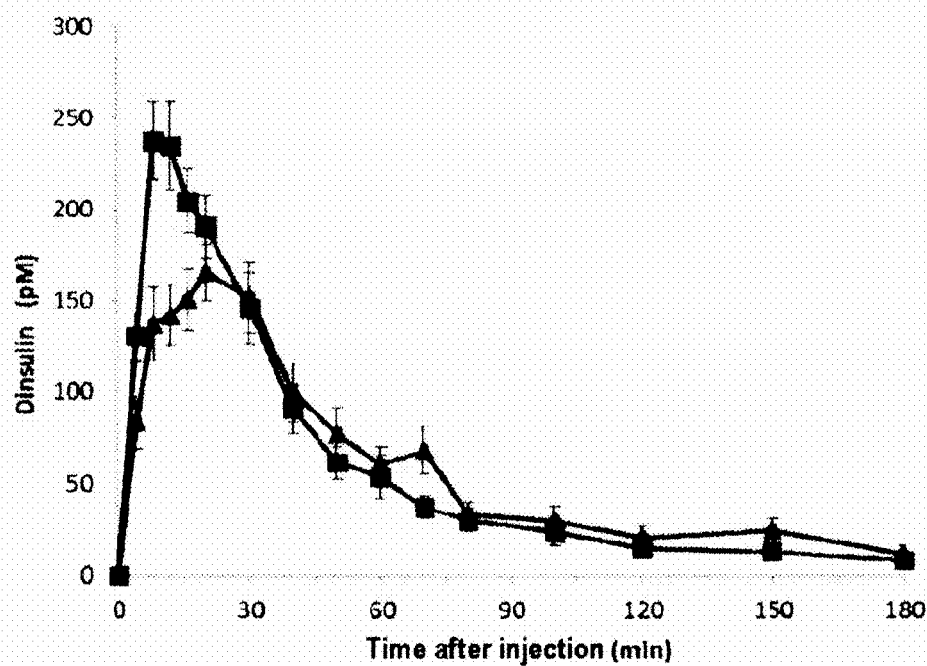

FIG. 14: DInsulin (pM) as a function of time after injection (min.). Curve plotted with the squares corresponding to example B11, insulin Tmax=13±5 min, curve plotted with the triangles corresponding to example B2, insulin Tmax=22±13 min.

Figure 15:
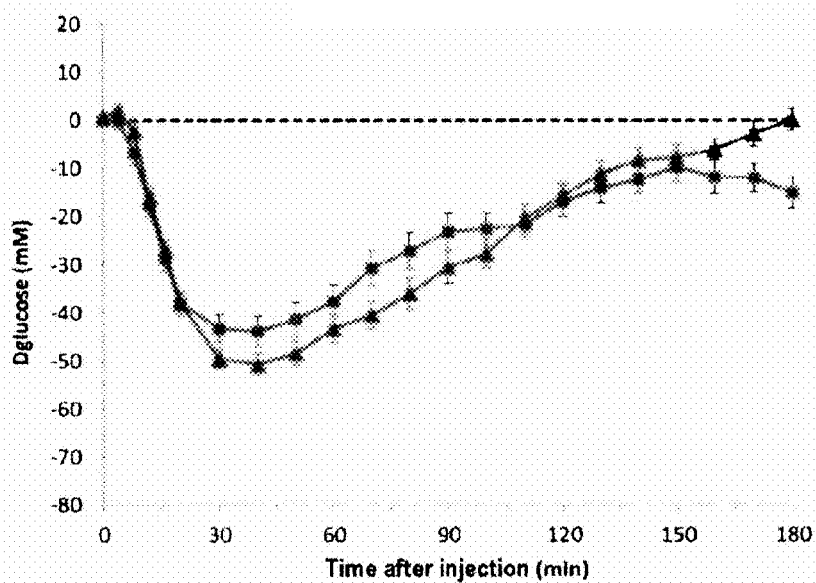

FIG. 15: DGlucose (mM) as a function of time after injection (min.). Curve plotted with the squares corresponding to example B102, glucose Tmin=47±30 min, curve plotted with the triangles corresponding to example B1, glucose Tmin=47±15 min.

Figure 16:
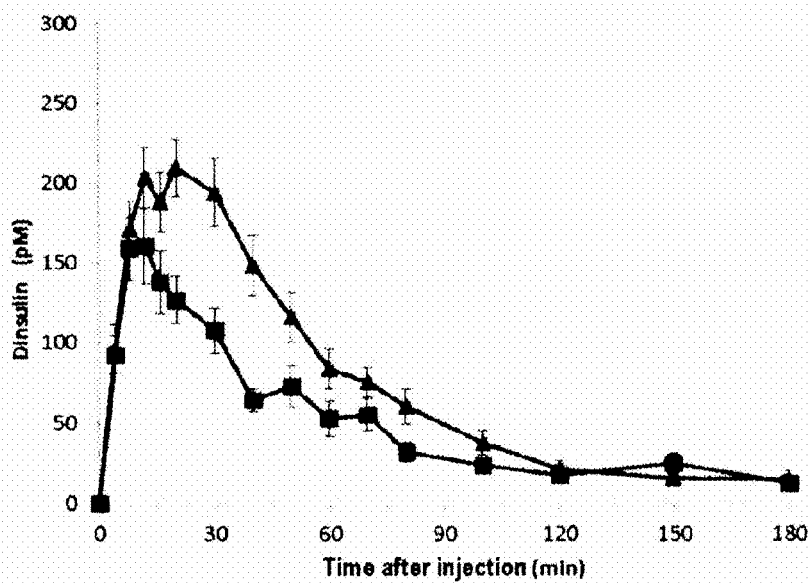

FIG. 16: DInsulin (pM) as a function of time after injection (min.). Curve plotted with the squares corresponding to example B38, insulin Tmax=22±21 min, curve plotted with the triangles corresponding to example B1, insulin Tmax=19±12 min.

Figure 17:
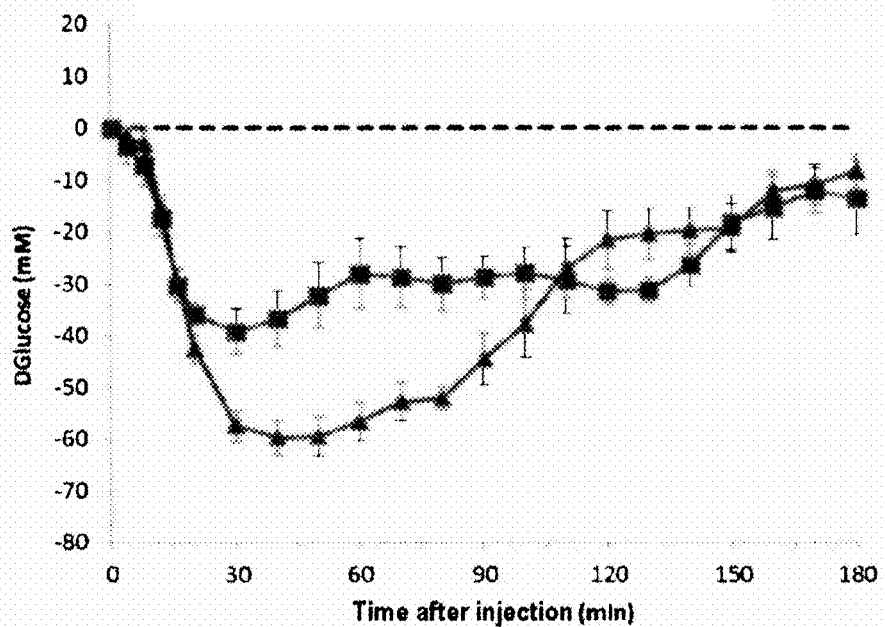

FIG. 17: DGlucose (mM) as a function of time after injection (min.). Curve plotted with the squares corresponding to example B53, glucose Tmin=63±36 min, curve plotted with the triangles corresponding to example B1, glucose Tmin=53±19 min.

Figure 18:
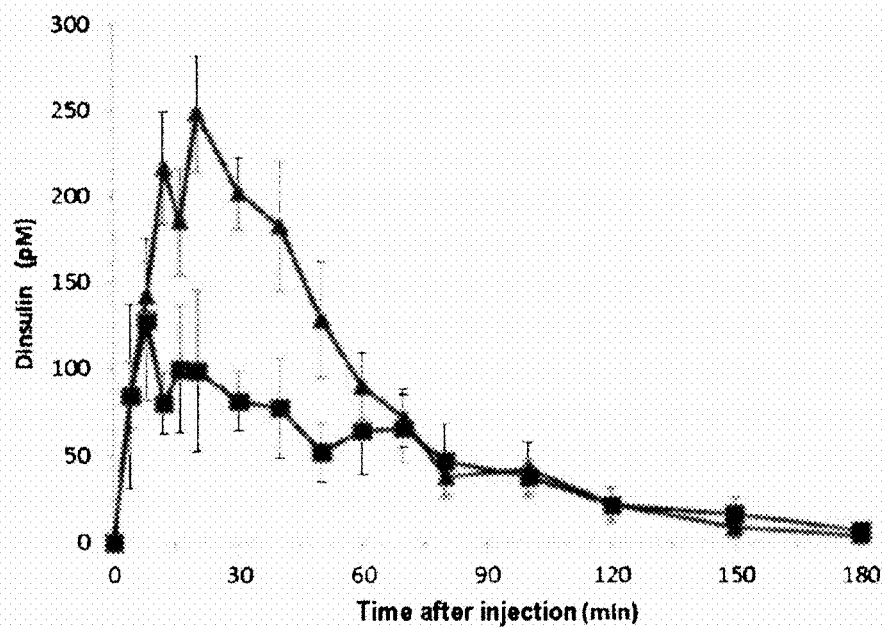

FIG. 18: DInsulin (pM) as a function of time after injection (min.). Curve plotted with the squares corresponding to example B53, insulin Tmax=19±12 min, curve plotted with the triangles corresponding to example B1, insulin Tmax=19±6 min.

Figure 19:
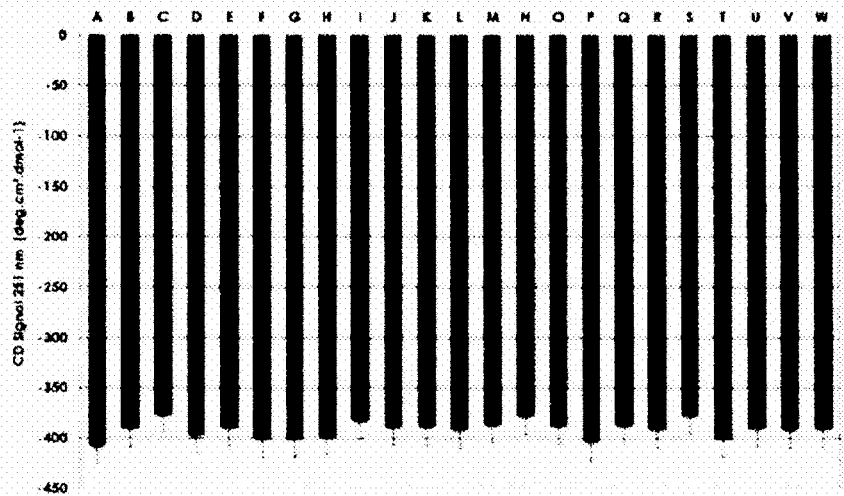

FIG. 19 describes on the x-axis:
A: lispro insulin (100 IU/mL)
B: lispro insulin+7.3 mg/mL of compound 2
C: lispro insulin+7.3 mg/mL of compound 2+citrate at 9.3 mM
D: lispro insulin+7.3 mg/mL of compound 1
E: lispro insulin+7.3 mg/mL of compound 1+citrate at 9.3 mM
F: lispro insulin+7.3 mg/mL of compound 3
G: lispro insulin+7.3 mg/mL of compound 3+citrate at 9.3 mM
H: lispro insulin+7.3 mg/mL of compound 4
I: lispro insulin+7.3 mg/mL of compound 4+citrate at 9.3 mM
J: lispro insulin+7.3 mg/mL of compound 5
K: lispro insulin+7.3 mg/mL of compound 5+citrate at 9.3 mM
L: lispro insulin+7.3 mg/mL of compound 6
M: lispro insulin+7.3 mg/mL of compound 6+citrate at 9.3 mM
N: lispro insulin+7.3 mg/mL of compound 7
O: lispro insulin+7.3 mg/mL of compound 7+citrate at 9.3 mM
P: lispro insulin+7.3 mg/mL of compound 8
Q: lispro insulin+7.3 mg/mL of compound 8+citrate at 9.3 mM
R: lispro insulin+7.3 mg/mL of compound 9
S: lispro insulin+7.3 mg/mL of compound 9+citrate at 9.3 mM
T: lispro insulin+7.3 mg/mL of compound 10

U: lispro insulin+7.3 mg/mL of compound 10+citrate at 9.3 mM
V: lispro insulin+7.3 mg/mL of compound 11
W: lispro insulin+7.3 mg/mL of compound 11+citrate at 9.3 mM and on the y-axis the circular dichroism signal at 251 nm (deg·cm$^2$·dmol$^{-1}$).

Figure 20:
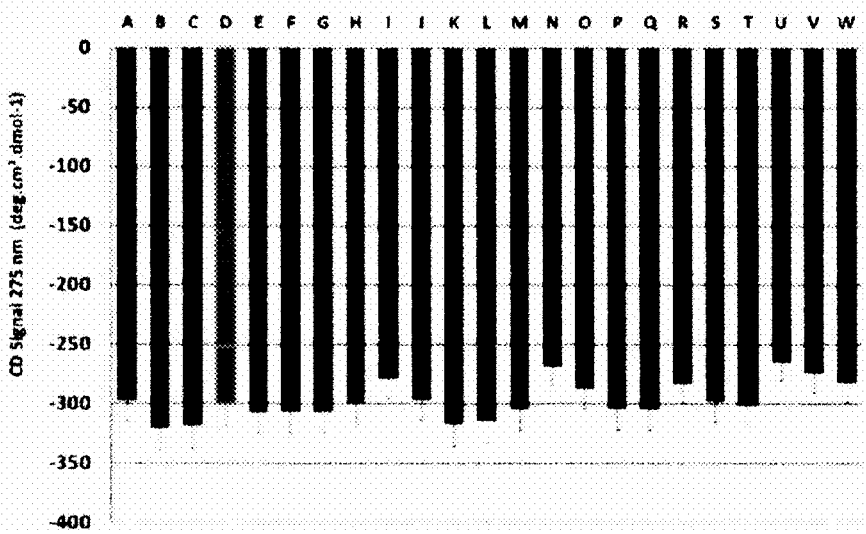

FIG. 20 describes on the x-axis:
A: human insulin (100 IU/mL)
B: human insulin+7.3 mg/mL of compound 2
C: human insulin+7.3 mg/mL of compound 2+citrate at 9.3 mM
D: human insulin+7.3 mg/mL of compound 1
E: human insulin+7.3 mg/mL of compound 1+citrate at 9.3 mM
F: human insulin+7.3 mg/mL of compound 3
G: human insulin+7.3 mg/mL of compound 3+citrate at 9.3 mM
H: human insulin+7.3 mg/mL of compound 4
I: human insulin+7.3 mg/mL of compound 4+citrate at 9.3 mM
J: human insulin+7.3 mg/mL of compound 5
K: human insulin+7.3 mg/mL of compound 5+citrate at 9.3 mM
L: human insulin+7.3 mg/mL of compound 6
M: human insulin+7.3 mg/mL of compound 6+citrate at 9.3 mM
N: human insulin+7.3 mg/mL of compound 7
O: human insulin+7.3 mg/mL of compound 7+citrate at 9.3 mM
P: human insulin+7.3 mg/mL of compound 8
Q: human insulin+7.3 mg/mL of compound 8+citrate at 9.3 mM
R: human insulin+7.3 mg/mL of compound 9
S: human insulin+7.3 mg/mL of compound 9+citrate at 9.3 mM
T: human insulin+7.3 mg/mL of compound 10
U: human insulin+7.3 mg/mL of compound 10+citrate at 9.3 mM
V: human insulin+7.3 mg/mL of compound 11
W: human insulin+7.3 mg/mL of compound 11+citrate at 9.3 mM and on the y-axis the circular dichroism signal at 275 nm (deg·cm$^2$·dmol$^{-1}$).

The invention consists of a composition, in aqueous solution, comprising insulin in hexameric form, at least one substituted anionic compound and a non-polymeric polyanionic compound.

The term "substituted anionic compound" means compounds consisting of a saccharide backbone formed from a discrete number u of between 1 and 8 ($1 \leq u \leq 8$) of identical or different saccharide units, linked via identical or different glycoside bonds, said saccharide units being chosen from the group consisting of hexoses, in cyclic form or in open reduced form, said compound comprising partially substituted carboxyl functional groups, the unsubstituted carboxyl functional groups being salifiable.

In one embodiment, the insulin is in hexameric form.
In one embodiment, the insulin is human insulin.

The term "human insulin" means an insulin obtained by synthesis or recombination, whose peptide sequence is the sequence of human insulin, including the allelic variations and homologs.

In one embodiment, the insulin is a recombinant human insulin as described in the European Pharmacopea and the American Pharmacopea.

In one embodiment, the insulin is an insulin analog.

The term "insulin analog" means a recombinant insulin whose primary sequence contains at least one modification relative to the primary sequence of human insulin.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the substituted anionic compound is chosen from substituted anionic compounds, in isolated form or as a mixture, consisting of a backbone formed from a discrete number u of between 1 and 8 ($1 \leq u \leq 8$) of identical or different saccharide units, linked via identical or different glycoside bonds, said saccharide units being chosen from the group consisting of hexoses, in cyclic form or in open reduced form, characterized in that they are substituted with:

a) at least one substituent of general formula I:

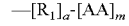
　　　　　　　　　　　　　　　　　　　　　　Formula I the substituents being identical or different when there are at least two substituents, in which:
the radical -[AA] denotes an amino acid residue,
the radical —R$_1$— being:
　either a bond and then a=0 and the amino acid residue -[AA] is directly linked to the backbone via a function G,
　or a C2 to C15 carbon-based chain, and then a=1, optionally substituted and/or comprising at least one heteroatom chosen from O, N and S and at least one acid function before the reaction with the amino acid, said chain forming with the amino acid residue -[AA] an amide function, and is attached to the backbone by means of a function F resulting from a reaction between a hydroxyl function borne by the backbone and a function or substituent borne by the precursor of the radical —R$_1$—,
F is a function chosen from ether, ester and carbamate functions,
G is a carbamate function,
m is equal to 1 or 2,
the degree of substitution of the saccharide units, j, in —[R$_1$]$_a$-[AA]$_m$ being strictly greater than 0 and less than or equal to 6, 0<j≤6 b) and, optionally, one or more substituents —R'$_1$,
the substituent —R'$_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —R'$_1$,
F' is an ether, ester or carbamate function,
the degree of substitution of the saccharide units, i, in —R'$_1$, being between 0 and 6−j, 0≤i≤6−j, and
F and F' are identical or different,
F and G are identical or different,
i+j≤6,
—R'$_1$ is identical to or different from —R$_1$—,
the free salifiable acid functions borne by the substituent —R'$_1$ are in the form of alkali metal cation salts, said glycoside bonds, which may be identical or different, being chosen from the group consisting of glycoside bonds of (1,1), (1,2), (1,3), (1,4) or (1,6) type, in an alpha or beta geometry.

In one embodiment, the substituted anionic compound, in isolated form or as a mixture, is chosen from substituted anionic compounds consisting of a saccharide backbone formed from a discrete number u of between 1 and 8 ($1 \leq u \leq 8$) of identical or different saccharide units, linked via identical or different glycoside bonds, said saccharide units being chosen from hexoses, in cyclic form or in open reduced form, characterized a) in that they are randomly substituted with:
at least one substituent of general formula I:

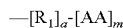  Formula I the substituents being identical or different when there are at least two substituents, in which:
the radical -[AA]- denotes an amino acid residue, said amino acid being chosen from the group consisting of phenylalanine, alpha-methylphenylalanine, 3,4-dihydroxyphenylalanine, tyrosine, alpha-methyltyrosine, O-methyltyrosine, alpha-phenylglycine, 4-hydroxyphenylglycine and 3,5-dihydroxyphenylglycine, and the alkali metal cation salts thereof, said derivatives being of L or D absolute configuration, -[AA] is attached to the backbone of the molecule via a linker arm —$R_1$— or directly linked to the backbone via a function G,
—$R_1$— being:
either a bond G, and then a=0,
or a C2 to C15 carbon-based chain, and then a=1, which is optionally substituted and/or comprising at least one heteroatom chosen from O, N and S and bearing at least one acid function before the reaction with the amino acid, said chain forming with the amino acid residue -[AA] an amide bond, and is attached to the saccharide backbone via a function F resulting from a reaction between a hydroxyl function borne by the backbone and a function borne by the precursor of $R_1$,
F is an ether, ester or carbamate function,
G is a carbamate function,
m is equal to 1 or 2,
the degree of substitution, j, in —$[R_1]_a$-$[AA]_m$ being strictly greater than 0 and less than or equal to 6, $0<j\leq6$, and, optionally,
one or more substituents —$R'_1$;
—$R'_1$ being a C2 to C15 carbon-based chain, which is optionally substituted and/or comprising at least one heteroatom (such as O, N and S) and bearing at least one acid function in the form of an alkali metal cation salt, said chain being attached to the saccharide backbone via a function F' resulting from a reaction between a hydroxyl function borne by the backbone and a function borne by the precursor of —$R'_1$,
F' is an ether, ester or carbamate function,
the degree of substitution, i, in —$R'_1$, being between 0 and 6−j, $0\leq i\leq 6-j$, and
—$R'_1$— is identical to or different from —$R_1$,
F and F' are identical or different,
F' and G are identical or different,
the free salifiable acid functions are in the form of alkali metal cation salts,
b) said glycoside bonds, which may be identical or different, being chosen from the group consisting of glycoside bonds of (1,1), (1,2), (1,3), (1,4) or (1,6) type, in an alpha or beta geometry,
c) $i+j\leq6$.

In one embodiment, m is equal to 1.
In one embodiment, —$R_1$ and —$R'_1$, which may be identical or different, are a C2 to C8 carbon-based chain.
In one embodiment, —$R_1$ and —$R'_1$, which may be identical or different, are a C2 to C4 carbon-based chain.

i and j are statistical degrees of substitution and represent the mean number of substituents per saccharide unit. Since each saccharide unit bears several hydroxyl functions of different reactivity, the distribution of the substituents on the substituted anionic compounds may be different from one saccharide unit to another within the same polyanionic compound.

In one embodiment, $0.3\leq i$.
In one embodiment, $0.4\leq i$.
In one embodiment, $i\leq 3$.
In one embodiment, $i\leq 2.5$.
In one embodiment, $0.3\leq j$.
In one embodiment, $0.4\leq j$.
In one embodiment, $j\leq 2$.
In one embodiment, $j\leq 1.8$.
In one embodiment, i and j are such that $0<i+j\leq 6$.
In one embodiment, $0<i+j\leq 5$.
In one embodiment, $0<i+j\leq 4$.
In one embodiment, $0<i+j\leq 3$.
In one embodiment, $0<i+j\leq 2.5$.
In one embodiment, $0<i+j\leq 2$.
In one embodiment, $0.5\leq i+j\leq 3$.
In one embodiment, $0.5\leq i+j\leq 2.5$.
In one embodiment, $0.5\leq i+j\leq 2$.
In one embodiment, $0.6\leq i+j\leq 3.5$.
In one embodiment, $0.8\leq i+j\leq 2.5$.
In one embodiment, $0.7\leq i+j\leq 2.5$.
In one embodiment, $0.7\leq i+j\leq 2$.
In one embodiment, $1<i+j\leq 2.5$.
In one embodiment, $1<i+j\leq 2$.
In one embodiment, —R1 and —R'1 are attached to the backbone via an ether bond.
In one embodiment, when —R1- is a carbon-based chain, it is directly attached to the backbone via an ether bond.
In one embodiment, when —R1- is a carbon-based chain, it optionally comprises a heteroatom chosen from the group consisting of O, N and S.
In one embodiment, —R1- forms with the amino acid residue AA an amide bond, and is directly attached to the backbone via an ether function F.
In one embodiment, —R1- forms with the amino acid residue AA an amide bond, and is directly attached to the backbone via a carbamate function F.
In one embodiment, —R1- forms with the amino acid residue AA an amide bond, and is directly attached to the backbone via an ester function F.
In one embodiment, —R1- and —R'1 are chosen from radicals of formulae II and III

  Formula II

Formula III

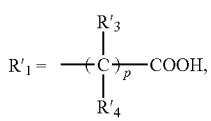

in which:

o and p, which may be identical or different, are greater than or equal to 1 and less than or equal to 12, and R₃, —R'₃, —R₄ and —R'₄, which may be identical or different, are chosen from the group consisting of a hydrogen atom, a saturated or unsaturated, linear, branched or cyclic C1 to C6 alkyl, a benzyl, a C7 to C10 alkylaryl and optionally comprising heteroatoms chosen from the group consisting of O, N and/or S, or functions chosen from the group consisting of carboxylic acid, amine, alcohol and thiol functions.

In one embodiment, —R1- before attachment to -AA-, is —CH₂—COOH.

In one embodiment, the substituted anionic compounds according to the invention are characterized in that the radical —R'1 is —CH₂—COOH.

In one embodiment, —R1- before optional attachment to -AA-, is derived from citric acid.

In one embodiment, —R1- before optional attachment to -AA-, is derived from malic acid.

In one embodiment, —R'1 is derived from citric acid.

In one embodiment, —R'1 is derived from malic acid.

In one embodiment, —R'1-, before attachment to -AA-, is chosen from the following groups, in which * represents the site of attachment to F:

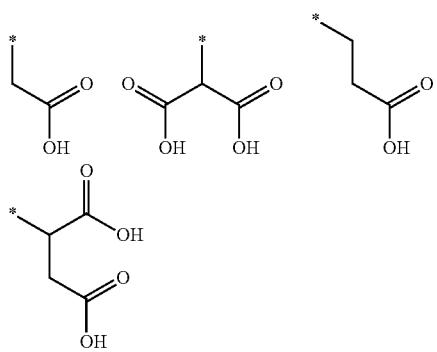

or the salts thereof with alkali metal cations chosen from the group consisting of Na⁺ and K⁺.

In one embodiment, —R'₁ is chosen from the following groups, in which * represents the site of attachment to F:

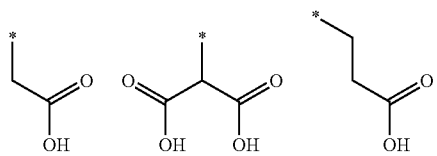

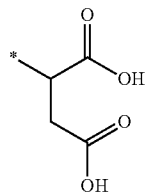

or the salts thereof with alkali metal cations chosen from the group consisting of Na⁺ and K⁺.

In one embodiment, the radical -[AA] is a residue of phenylalanine and of alkali metal cation salts thereof of L, D or racemic absolute configuration.

In one embodiment, the radical -[AA] is a residue of alpha-methylphenylalanine and of alkali metal cation salts thereof of L, D or racemic absolute configuration.

In one embodiment, the radical -[AA] is a residue of 3,4-dihydroxyphenylalanine and of alkali metal cation salts thereof of L, D or racemic absolute configuration.

In one embodiment, the radical -[AA] is a residue of tyrosine and of alkali metal cation salts thereof of L, D or racemic absolute configuration.

In one embodiment, the radical -[AA] is a residue of alpha-methyltyrosine and of alkali metal cation salts thereof of L, D or racemic absolute configuration.

In one embodiment, the radical -[AA] is a residue of O-methyltyrosine and of alkali metal cation salts thereof of L, D or racemic absolute configuration.

In one embodiment, the radical -[AA] is a residue of alpha-phenylglycine and of alkali metal cation salts thereof of L, D or racemic absolute configuration.

In one embodiment, the radical -[AA] is a residue of 4-hydroxyphenylglycine and of alkali metal cation salts thereof of L, D or racemic absolute configuration.

In one embodiment, the radical -[AA] is a residue of 3,5-dihydroxyphenylglycine and of alkali metal cation salts thereof of L, D or racemic absolute configuration.

In one embodiment, the radical -[AA] is an amino acid residue in the form of a racemic mixture.

In one embodiment, the radical -[AA] is an amino acid residue in the form of isolated isomers of D absolute configuration.

In one embodiment, the radical -[AA] is an amino acid residue in the form of isolated isomers of L absolute configuration.

In one embodiment, u is between 1 and 5.
In one embodiment, u is between 3 and 5.
In one embodiment, u=8.
In one embodiment, u=7.
In one embodiment, u=6.
In one embodiment, u=5.
In one embodiment, u=4.
In one embodiment, u=3.
In one embodiment, u=2.
In one embodiment, u=1.

In one embodiment, hexoses are chosen from the group consisting of mannose, glucose, fructose, sorbose, tagatose, psicose, galactose, allose, altrose, talose, idose, gulose, fucose, fuculose, rhamnose, mannitol, sorbitol and galactitol (dulcitol).

In one embodiment, the glycoside bonds are of (1,4) or (1,6) type.

In one embodiment, the substituted anionic compound is chosen from anionic compounds consisting of a saccharide backbone formed from a discrete number u=2 of identical or different saccharide units chosen from hexoses linked via a glycoside bond of (1,1) type.

In one embodiment, the substituted anionic compound is chosen from anionic compounds consisting of a saccharide backbone formed from a discrete number u=2 of different saccharide units chosen from hexoses and linked via a glycoside bond of (1,1) type, said saccharide backbone being chosen from the group consisting of trehalose and sucrose.

In one embodiment, the substituted anionic compound is chosen from anionic compounds consisting of a saccharide backbone formed from a discrete number u=2 of identical or different saccharide units chosen from hexoses linked via a glycoside bond of (1,2) type.

In one embodiment, the substituted anionic compound is chosen from anionic compounds consisting of a saccharide backbone formed from a discrete number u=2 of identical or different saccharide units chosen from hexoses linked via a glycoside bond of (1,2) type, said saccharide backbone being kojibiose.

In one embodiment, the substituted anionic compound is chosen from anionic compounds consisting of a saccharide backbone formed from a discrete number u=2 of identical or different saccharide units chosen from hexoses linked via a glycoside bond of (1,3) type.

In one embodiment, the substituted anionic compound is chosen from anionic compounds consisting of a saccharide backbone formed from a discrete number u=2 of identical or different saccharide units chosen from hexoses linked via a glycoside bond of (1,3) type, said saccharide backbone being chosen from the group consisting of nigeriose and laminaribiose.

In one embodiment, the substituted anionic compound is chosen from anionic compounds consisting of a saccharide backbone formed from a discrete number u=2 of identical or different saccharide units chosen from hexoses linked via a glycoside bond of (1,4) type.

In one embodiment, the substituted anionic compound is chosen from anionic compounds consisting of a saccharide backbone formed from a discrete number u=2 of identical or different saccharide units chosen from hexoses linked via a glycoside bond of (1,4) type, said saccharide backbone being chosen from the group consisting of maltose, lactose and cellobiose.

In one embodiment, the substituted anionic compound is chosen from anionic compounds consisting of a saccharide backbone formed from a discrete number u=2 of identical or different saccharide units chosen from hexoses linked via a glycoside bond of (1,6) type.

In one embodiment, the substituted anionic compound is chosen from anionic compounds consisting of a saccharide backbone formed from a discrete number u=2 of identical or different saccharide units chosen from hexoses linked via a glycoside bond of (1,6) type, said saccharide backbone being chosen from the group consisting of isomaltose, melibiose and gentiobiose.

In one embodiment, the substituted anionic compound is chosen from anionic compounds consisting of a saccharide backbone formed from a discrete number u=2 of identical or different saccharide units chosen from hexoses linked via a glycoside bond of (1,6) type, said saccharide backbone being isomaltose.

In one embodiment, the substituted anionic compound is chosen from anionic compounds consisting of a saccharide backbone formed from a discrete number u=2 of saccharide units, one of which is in cyclic form and the other in open reduced form.

In one embodiment, the substituted anionic compound is chosen from anionic compounds consisting of a saccharide backbone formed from a discrete number u=2 of saccharide units, one of which is in cyclic form and the other in open reduced form, said saccharide backbone being chosen from the group consisting of maltitol and isomaltitol.

In one embodiment, the substituted anionic compound according to the invention is characterized in that the saccharide backbone is formed from a discrete number $3 \leq u \leq 8$ of identical or different saccharide units.

In one embodiment, the substituted anionic compound according to the invention is characterized in that at least one of the identical or different saccharide units, of which the saccharide backbone formed from a discrete number $3 \leq u \leq 8$ of saccharide units is composed, is chosen from the group consisting of hexose units linked via identical or different glycoside bonds.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,2) type.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,3) type.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,4) type.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,6) type.

In one embodiment, the substituted anionic compound according to the invention is characterized in that the saccharide backbone is formed from a discrete number u=3 of identical or different saccharide units.

In one embodiment, the substituted anionic compound according to the invention is characterized in that it comprises at least one saccharide unit chosen from the group consisting of hexoses in cyclic form and at least one saccharide unit chosen from the group consisting of hexoses in open form.

In one embodiment, the substituted anionic compound according to the invention is characterized in that the three saccharide units are identical.

In one embodiment, the substituted anionic compound according to the invention is characterized in that two of the three saccharide units are identical.

In one embodiment, the substituted anionic compound according to the invention is characterized in that the identical saccharide units are chosen from hexoses, two of which are in cyclic form and one is in open reduced form, and linked via glycoside bonds of (1,4) type.

In one embodiment, the substituted anionic compound according to the invention is characterized in that the identical saccharide units are chosen from hexoses, two of which are in cyclic form and one is in open reduced form, and linked via glycoside bonds of (1,6) type.

In one embodiment, the substituted anionic compound according to the invention is characterized in that the identical or different saccharide units are chosen from hexoses and in that the central hexose is linked via a glycoside bond of (1,2) type and via a glycoside bond of (1,4) type.

In one embodiment, the substituted anionic compound according to the invention is characterized in that the identical or different saccharide units are chosen from hexoses and in that the central hexose is linked via a glycoside bond of (1,3) type and via a glycoside bond of (1,4) type.

In one embodiment, the substituted anionic compound according to the invention is characterized in that the identical or different saccharide units are chosen from hexoses and in that the central hexose is linked via a glycoside bond of (1,2) type and via a glycoside bond of (1,6) type.

In one embodiment, the substituted anionic compound according to the invention is characterized in that the identical or different saccharide units are chosen from hexoses and in that the central hexose is linked via a glycoside bond of (1,2) type and via a glycoside bond of (1,3) type.

In one embodiment, the substituted anionic compound according to the invention is characterized in that the identical or different saccharide units are chosen from hexoses and in that the central hexose is linked via a glycoside bond of (1,4) type and via a glycoside bond of (1,6) type.

In one embodiment, the substituted anionic compound according to the invention is characterized in that the saccharide backbone is erlose.

In one embodiment, the substituted anionic compound according to the invention is characterized in that the three identical or different saccharide units are hexose units chosen from the group consisting of mannose and glucose.

In one embodiment, the substituted anionic compound according to the invention is characterized in that the saccharide backbone is maltotriose.

In one embodiment, the substituted anionic compound according to the invention is characterized in that the saccharide backbone is isomaltotriose.

In one embodiment, the substituted anionic compound according to the invention is characterized in that the saccharide backbone is formed from a discrete number $u=4$ of identical or different saccharide units.

In one embodiment, the substituted anionic compound according to the invention is characterized in that the four saccharide units are identical.

In one embodiment, the substituted anionic compound according to the invention is characterized in that three of the four saccharide units are identical.

In one embodiment, the substituted anionic compound according to the invention is characterized in that the four saccharide units are hexose units chosen from the group consisting of mannose and glucose.

In one embodiment, the substituted anionic compound according to the invention is characterized in that the saccharide backbone is maltotetraose.

In one embodiment, the substituted anionic compound according to the invention is characterized in that the identical or different saccharide units are chosen from hexoses and in that a terminal hexose is linked via a glycoside bond of (1,2) type and in that the others are linked together via a glycoside bond of (1,6) type.

In one embodiment, the substituted anionic compound according to the invention is characterized in that the identical or different saccharide units are chosen from hexoses and linked via a glycoside bond of (1,6) type.

In one embodiment, the substituted anionic compound according to the invention is characterized in that the saccharide backbone is formed from a discrete number $u=5$ of identical or different saccharide units.

In one embodiment, the substituted anionic compound according to the invention is characterized in that the five saccharide units are identical.

In one embodiment, the substituted anionic compound according to the invention is characterized in that the five saccharide units are hexose units chosen from the group consisting of mannose and glucose.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the saccharide backbone is maltopentaose.

In one embodiment, the substituted anionic compound according to the invention is characterized in that the saccharide backbone is formed from a discrete number $u=6$ of identical or different saccharide units.

In one embodiment, the substituted anionic compound according to the invention is characterized in that the six saccharide units are identical.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the six identical or different saccharide units are hexose units chosen from the group consisting of mannose and glucose.

In one embodiment, the substituted anionic compound according to the invention is characterized in that the saccharide backbone is maltohexaose.

In one embodiment, the substituted anionic compound according to the invention is characterized in that the saccharide backbone is formed from a discrete number $u=7$ of identical or different saccharide units.

In one embodiment, the substituted anionic compound according to the invention is characterized in that the seven saccharide units are identical.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the seven saccharide units are hexose units chosen from the group consisting of mannose and glucose.

In one embodiment, the substituted anionic compound according to the invention is characterized in that the saccharide backbone is maltoheptaose.

In one embodiment, the substituted anionic compound according to the invention is characterized in that the saccharide backbone is formed from a discrete number $u=8$ of identical or different saccharide units.

In one embodiment, the substituted anionic compound according to the invention is characterized in that the eight saccharide units are identical.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the eight saccharide units are hexose units chosen from the group consisting of mannose and glucose.

In one embodiment, the substituted anionic compound according to the invention is characterized in that the saccharide backbone is maltooctaose.

In one embodiment, the substituted anionic compound comprising a discrete number of saccharide units is a natural compound.

In one embodiment, the substituted anionic compound comprising a discrete number of saccharide units is a synthetic compound.

In one embodiment, the substituted anionic compound according to the invention is characterized in that it is obtained by enzymatic degradation of a polysaccharide followed by purification.

In one embodiment, the substituted anionic compound according to the invention is characterized in that it is obtained by chemical degradation of a polysaccharide followed by purification.

In one embodiment, the substituted anionic compound according to the invention is characterized in that it is obtained chemically, by covalent coupling of precursors of lower molecular weight.

In one embodiment, the substituted anionic compound according to the invention is characterized in that the saccharide backbone is sophorose.

In one embodiment, the substituted anionic compound according to the invention is characterized in that the saccharide backbone is sucrose.

In one embodiment, the substituted anionic compound according to the invention is characterized in that the saccharide backbone is lactulose.

In one embodiment, the substituted anionic compound according to the invention is characterized in that the saccharide backbone is maltulose.

In one embodiment, the substituted anionic compound according to the invention is characterized in that the saccharide backbone is leucrose.

In one embodiment, the substituted anionic compound according to the invention is characterized in that the saccharide backbone is rutinose.

In one embodiment, the substituted anionic compound according to the invention is characterized in that the saccharide backbone is isomaltulose.

In one embodiment, the substituted anionic compound according to the invention is characterized in that the saccharide backbone is fucosyllactose.

In one embodiment, the substituted anionic compound according to the invention is characterized in that the saccharide backbone is gentianose.

In one embodiment, the substituted anionic compound according to the invention is characterized in that the saccharide backbone is raffinose.

In one embodiment, the substituted anionic compound according to the invention is characterized in that the saccharide backbone is melezitose.

In one embodiment, the substituted anionic compound according to the invention is characterized in that the saccharide backbone is panose.

In one embodiment, the substituted anionic compound according to the invention is characterized in that the saccharide backbone is kestose.

In one embodiment, the substituted anionic compound according to the invention is characterized in that the saccharide backbone is stachyose.

In one embodiment, the polyanionic compound is a non-polymeric polyanionic (NPP) compound whose affinity for zinc is less than the affinity of insulin for zinc and whose dissociation constant $Kd_{Ca} = [\text{NPP compound}]^r [Ca^{2+}]^s / [(\text{NPP compound})^r - (Ca^{2+})^s]$ is less than or equal to $10^{-1.5}$.

The dissociation constants (Kd) of the various polyanionic compounds with respect to calcium ions are determined by external calibration using an electrode specific for calcium ions (Mettler-Toledo) and a reference electrode. All the measurements are performed in 150 mM NaCl at pH 7. Only the concentrations of free calcium ions are determined; the calcium ions bound to the polyanionic compound do not induce any electrode potential.

In one embodiment, the polyanionic compound is chosen from the group consisting of polycarboxylic acids and the $Na^+$, $K^+$, $Ca^{2+}$ or $Mg^{2+}$ salts thereof.

In one embodiment, the polycarboxylic acid is chosen from the group consisting of citric acid and tartaric acid, and the $Na^+$, $K^+$, $Ca^{2+}$ or $Mg^{2+}$ salts thereof.

In one embodiment, the polyanionic compound is chosen from the group consisting of polyphosphoric acids and the $Na^+$, $K^+$, $Ca^{2+}$ or $Mg^{2+}$ salts thereof.

In one embodiment, the polyphosphoric acid is triphosphate and the $Na^+$, $K^+$, $Ca^{2+}$ or $Mg^{2+}$ salts thereof.

In one embodiment, the polyanionic compound is citric acid and the $Na^+$, $K^+$, $Ca^{2+}$ or $Mg^{2+}$ salts thereof.

In one embodiment, the polyanionic compound is tartaric acid and the $Na^+$, $K^+$, $Ca^{2+}$ or $Mg^{2+}$ salts thereof.

In one embodiment, the polyanionic compound is triphosphoric acid and the $Na^+$, $K^+$, $Ca^{2+}$ or $Mg^{2+}$ salts thereof.

In one embodiment, the polyanionic compound is a compound consisting of a saccharide backbone formed from a discrete number of saccharide units obtained from a disaccharide compound chosen from the group consisting of trehalose, maltose, lactose, sucrose, cellobiose, isomaltose, maltitol and isomaltitol.

In one embodiment, the polyanionic compound consisting of a saccharide backbone formed from a discrete number of saccharide units is obtained from a compound consisting of a backbone formed from a discrete number of saccharide units chosen from the group consisting of maltotriose, maltotetraose, maltopentaose, maltohexaose, maltoheptaose, maltooctaose and isomaltotriose.

In one embodiment, the polyanionic compound consisting of a saccharide backbone formed from a discrete number of saccharide units is chosen from the group consisting of carboxymethylmaltotriose, carboxymethylmaltotetraose, carboxymethylmaltopentaose, carboxymethylmaltohexaose, carboxymethylmaltoheptaose, carboxymethylmaltooctaose and carboxymethylisomaltotriose.

In one embodiment, the ratio (number of moles of acid functions borne by the polyanionic compound/number of moles of anionic compound) is greater than or equal to 3.

In one embodiment, the ratio (number of moles of acid functions borne by the polyanionic compound/number of moles of anionic compound) is greater than or equal to 4.

In one embodiment, the ratio (number of moles of acid functions borne by the polyanionic compound consisting of a saccharide backbone/number of moles of anionic compound) is greater than or equal to 5.

In one embodiment, the ratio (number of moles of acid functions borne by the polyanionic compound consisting of a saccharide backbone/number of moles of anionic compound) is greater than or equal to 8.

In one embodiment, the substituted anionic compound/insulin mole ratios are between 0.6 and 75.

In one embodiment, the mole ratios are between 0.7 and 50.

In one embodiment, the mole ratios are between 1.4 and 35.

In one embodiment, the mole ratios are between 1.9 and 30.

In one embodiment, the mole ratios are between 2.3 and 30.

In one embodiment, the substituted anionic compound/insulin mole ratio is equal to 8.

In one embodiment, the substituted anionic compound/insulin mole ratio is equal to 12.

In one embodiment, the substituted anionic compound/insulin mole ratio is equal to 16.

In one embodiment, the substituted anionic compound/insulin mass ratios are between 0.5 and 10.

In one embodiment, the mass ratios are between 0.6 and 7.

In one embodiment, the mass ratios are between 1.2 and 5.

In one embodiment, the mass ratios are between 1.6 and 4.

In one embodiment, the mass ratios are between 2 and 4.

In one embodiment, the substituted anionic compound/insulin mass ratio is 2.

In one embodiment, the substituted anionic compound/insulin mass ratio is 3.

In one embodiment, the substituted anionic compound/insulin mass ratio is 4.

In one embodiment, the substituted anionic compound/insulin mass ratio is 6.

In one embodiment, the concentration of substituted anionic compound is between 1.8 and 36 mg/mL.

In one embodiment, the concentration of substituted anionic compound is between 1.8 and 36.5 mg/mL.

In one embodiment, the concentration of substituted anionic compound is between 2.1 and 25 mg/mL.

In one embodiment, the concentration of substituted anionic compound is between 4.2 and 18 mg/mL.

In one embodiment, the concentration of substituted anionic compound is between 5.6 and 15 mg/mL.

In one embodiment, the concentration of substituted anionic compound is between 7 and 15 mg/mL.

In one embodiment, the concentration of substituted anionic compound is 7.3 mg/mL.

In one embodiment, the concentration of substituted anionic compound is 10.5 mg/mL.

In one embodiment, the concentration of substituted anionic compound is 14.6 mg/mL.

In one embodiment, the concentration of substituted anionic compound is 21.9 mg/mL.

In one embodiment, the concentration of polyanionic compound is between 2 and 150 mM.

In one embodiment, the concentration of polyanionic compound is between 2 and 100 mM.

In one embodiment, the concentration of polyanionic compound is between 2 and 75 mM.

In one embodiment, the concentration of polyanionic compound is between 2 and 50 mM.

In one embodiment, the concentration of polyanionic compound is between 2 and 30 mM.

In one embodiment, the concentration of polyanionic compound is between 2 and 20 mM.

In one embodiment, the concentration of polyanionic compound is between 2 and 10 mM.

In one embodiment, the concentration of polyanionic compound is between 5 and 150 mM.

In one embodiment, the concentration of polyanionic compound is between 5 and 100 mM.

In one embodiment, the concentration of polyanionic compound is between 5 and 75 mM.

In one embodiment, the concentration of polyanionic compound is between 5 and 50 mM.

In one embodiment, the concentration of polyanionic compound is between 5 and 30 mM.

In one embodiment, the concentration of polyanionic compound is between 5 and 20 mM.

In one embodiment, the concentration of polyanionic compound is between 5 and 10 mM.

In one embodiment, the concentration of polyanionic compound is between 0.5 and 30 mg/mL.

In one embodiment, the concentration of polyanionic compound is between 0.5 and 25 mg/mL.

In one embodiment, the concentration of polyanionic compound is between 0.5 and 10 mg/mL.

In one embodiment, the concentration of polyanionic compound is between 0.5 and 8 mg/mL.

In one embodiment, the concentration of polyanionic compound is between 1 and 30 mg/mL.

In one embodiment, the concentration of polyanionic compound is between 1.5 and 25 mg/mL.

In one embodiment, the concentration of polyanionic compound is between 2 and 25 mg/mL.

In one embodiment, the concentration of polyanionic compound is between 2 and 10 mg/mL.

In one embodiment, the concentration of polyanionic compound is between 2 and 8 mg/mL.

In one embodiment, the substituted anionic compound is sodium maltotriosemethylcarboxylate modified with sodium phenylalaninate, u=3, i=0.65, j=1.0.

In one embodiment, the substituted anionic compound is sodium maltotriosemethylcarboxylate modified with sodium phenylalaninate, u=3, i=1.0, j=0.65.

In one embodiment, the substituted anionic compound is sodium maltotriosemethylcarboxylate modified with sodium phenylalaninate, u=3, i=0.46, j=1.2.

In one embodiment, the substituted anionic compound is sodium maltotriosemethylcarboxylate modified with sodium phenylalaninate, u=3, i=0.35, j=0.65.

In one embodiment, the polyanionic compound is sodium maltotriosemethylcarboxylate.

In one embodiment, the polyanionic compound is sodium citrate.

In one embodiment, the polyanionic compound is triphosphate in acidic form or in basic form in the form of the sodium salt or the potassium salt.

In one embodiment, the polyanionic compound is tartrate in acidic form or in basic form in the form of the sodium salt or the potassium salt.

The invention also relates to an insulin pharmaceutical formulation comprising a composition according to the invention, in which the insulin is in hexameric form.

In one embodiment, it relates to a pharmaceutical formulation characterized in that the insulin concentration is between 240 and 3000 µM (40 to 500 IU/mL).

In one embodiment, it relates to a pharmaceutical formulation characterized in that the insulin concentration is between 600 and 3000 µM (100 to 500 IU/mL).

In one embodiment, it relates to a pharmaceutical formulation characterized in that the insulin concentration is between 600 and 2400 µM (100 to 400 IU/mL).

In one embodiment, it relates to a pharmaceutical formulation characterized in that the insulin concentration is between 600 and 1800 µM (100 to 300 IU/mL).

In one embodiment, it relates to a pharmaceutical formulation characterized in that the insulin concentration is between 600 and 1200 μM (100 to 200 IU/mL).

In one embodiment, it relates to a pharmaceutical formulation characterized in that the insulin concentration is 600 μM (100 IU/mL).

In one embodiment, it relates to a pharmaceutical formulation characterized in that the insulin concentration is 1200 μM (200 IU/mL).

In one embodiment, it relates to a pharmaceutical formulation characterized in that the insulin concentration is 1800 μM (300 IU/mL).

In one embodiment, it relates to a pharmaceutical formulation characterized in that the insulin concentration is 2400 μM (400 IU/mL).

In one embodiment, it relates to a pharmaceutical formulation characterized in that the insulin concentration is 3000 μM (500 IU/mL).

The invention relates to the use of at least one substituted anionic compound, said compound consisting of a saccharide backbone formed from a discrete number u of between 1 and 8 (1≤u≤8) of identical or different saccharide units, linked via identical or different glycoside bonds, said saccharide units being chosen from the group consisting of hexoses, in cyclic form or in open reduced form, said compound comprising partially substituted carboxyl functional groups, the unsubstituted carboxyl functional groups being salifiable to prepare a pharmaceutical formulation of human insulin, in combination with a polyanionic compound, making it possible, after administration, to accelerate the passage of the insulin into the blood and to reduce glycemia more rapidly when compared with a formulation free of substituted anionic compound, and optionally of anionic compounds.

In one embodiment, the invention relates to the use of at least one substituted anionic compound, said compound comprising partially substituted carboxyl functional groups, the unsubstituted carboxyl functional groups being salifiable, to prepare a pharmaceutical formulation of human insulin, in combination with a polyanionic compound, making it possible, after administration, to accelerate the passage of the human insulin into the blood and to reduce glycemia more rapidly when compared with a formulation free of substituted anionic compound, and optionally of anionic compounds.

In one embodiment, the invention relates to the use of at least one substituted anionic compound, said compound comprising partially substituted carboxyl functional groups, the unsubstituted carboxyl functional groups being salifiable, to prepare an insulin analog formulation, in combination with a polyanionic compound, making it possible, after administration, to accelerate the passage of the insulin analog into the blood and to reduce glycemia more rapidly when compared with a formulation free of substituted anionic compound, and optionally of anionic compounds.

In one embodiment, the insulin is human insulin.

The term "human insulin" means an insulin obtained by synthesis or recombination, whose peptide sequence is the sequence of human insulin, including the allelic variations and homologs.

In one embodiment, the insulin is a recombinant human insulin as described in the European Pharmacopea and the American Pharmacopea.

In one embodiment, the insulin is an insulin analog.

The term "insulin analog" means a recombinant insulin whose primary sequence contains at least one modification relative to the primary sequence of human insulin.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the use is characterized in that the substituted anionic compound is chosen from substituted anionic compounds, in isolated form or as a mixture, consisting of a saccharide backbone formed from a discrete number u of between 1 and 8 (1≤u≤8) of identical or different saccharide units, linked via identical or different glycoside bonds, said saccharide units being chosen from hexoses, in cyclic form or in open reduced form, characterized in that they are substituted with:

a) at least one substituent of general formula I:

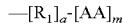

Formula I the substituents being identical or different when there are at least two substituents, in which:

the radical -[AA] denotes an amino acid residue, the radical —R$_1$— being:

either a bond and then a =0 and the amino acid residue -[AA]- is directly linked to the backbone via a function G, or a C2 to C15 carbon-based chain, and then a=1, optionally substituted and/or comprising at least one heteroatom chosen from O, N and S and at least one acid function before the reaction with the amino acid, said chain forming with the amino acid residue -[AA]- an amide function, and is attached to the backbone by means of a function F resulting from a reaction between a hydroxyl function borne by the backbone and a function or substituent borne by the precursor of the radical —R$_1$—, F is a function chosen from ether, ester and carbamate functions, G is a carbamate function, m is equal to 1 or 2, the degree of substitution of the saccharide units, j, in —[R$_1$]$_a$-[AA]$_m$ being strictly greater than 0 and less than or equal to 6, 0<j≤6 b) and, optionally, one or more substituents —R'$_1$, the substituent —R'$_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —R'$_1$, F' is an ether, ester or carbamate function, the degree of substitution of the saccharide units, i, in —R'$_1$, being between 0 and 6-j, 0≤i≤6-j, and F and F' are identical or different, F and G are identical or different, i+j≤6, —R'$_1$ is identical to or different from —R$_1$—, the free salifiable acid functions borne by the substituent —R'$_1$ are in the form of alkali metal cation salts, said glycoside bonds, which may be identical or different, being chosen from the group consisting of glycoside bonds of (1,1), (1,2), (1,3), (1,4) or (1,6) type, in an alpha or beta geometry.

In one embodiment, the use is characterized in that the substituted anionic compound, in isolated form or as a mixture, is chosen from substituted anionic compounds consisting of a saccharide backbone formed from a discrete number u of between 1 and 8 (1≤u≤8) of identical or different saccharide units, linked via identical or different glycoside bonds, said saccharide units being chosen from hexoses, in cyclic form or in open reduced form, characterized a) in that they are randomly substituted with:
at least one substituent of general formula I:

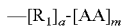  Formula I the substituents being identical or different when there are at least two substituents, in which:
the radical -[AA]- denotes an amino acid residue, said amino acid being chosen from the group consisting of phenylalanine, alpha-methylphenylalanine, 3,4-dihydroxyphenylalanine, tyrosine, alpha-methyltyrosine, O-methyltyrosine, alpha-phenylglycine, 4-hydroxyphenylglycine and 3,5-dihydroxyphenylglycine, and the alkali metal cation salts thereof, said derivatives being in L or D absolute configuration, -[AA]- is attached to the backbone of the molecule via a linker arm —$R_1$— or directly attached to the backbone via a function G,
—$R_1$— being:
either a bond G, and then a=0,
or a C2 to C15 carbon-based chain, and then a=1, optionally substituted and/or comprising at least one heteroatom chosen from O, N and S and bearing at least one acid function before the reaction with the amino acid, said chain forming with the amino acid residue -[AA]- an amide bond, and is attached to the saccharide backbone by means of a function F resulting from a reaction between a hydroxyl function borne by the backbone and a function borne by the precursor of $R_1$,
F is an ether, ester or carbamate function,
G is a carbamate function,
m is equal to 1 or 2,
the degree of substitution, j, in —$[R_1]_a$-$[AA]_m$ being strictly greater than 0 and less than or equal to 6, $0<j\leq6$,
and, optionally,
one or more substituents —$R'_1$
—$R'_1$ being a C2 to C15 carbon-based chain, which is optionally substituted and/or comprising at least one heteroatom (such as O, N and S) and bearing at least one acid function in the form of an alkali metal cation salt, said chain being attached to the saccharide backbone via a function F' resulting from a reaction between a hydroxyl function borne by the backbone and a function borne by the precursor of —$R'_1$,
F' is an ether, ester or carbamate function,
the degree of substitution, i, in —$R'_1$, being between 0 and 6−j, $0\leq i\leq 6-j$, and
—$R'_1$— is identical to or different from —$R_1$,
F and F' are identical or different,
F' and G are identical or different,
the free salifiable acid functions are in the form of alkali metal cation salts, b) said glycoside bonds, which may be identical or different, being chosen from the group consisting of glycoside bonds of (1,1), (1,2), (1,3), (1,4) or (1,6) type, in an alpha or beta geometry, c) i+j≤6.

In one embodiment, m is equal to 1.
In one embodiment, —R1 and —R'1, which may be identical or different, are a C1 to C8 carbon-based chain.
In one embodiment, —R1 and —R'1, which may be identical or different, are a C1 to C4 carbon-based chain.
In one embodiment, —R1 and —R'1, which may be identical or different, are a C1 to C2 carbon-based chain.

It is known to those skilled in the art that the delay of action of insulins is dependent on the insulin concentration. Only the delay of action values for formulations at 100 IU/mL are documented.

"Regular" human insulin formulations on the market at a concentration of 600 μM (100 IU/mL) have a delay of action of between 50 and 90 minutes and an end of action of about 360 to 420 minutes in man. The time to achieve the maximum insulin concentration in the blood is between 90 and 180 minutes in man.

Rapid insulin analog formulations on the market at a concentration of 600 μM (100 IU/mL) have a delay of action of between 30 and 60 minutes and an end of action of about 240-300 minutes in man. The time to achieve the maximum insulin concentration in the blood is between 50 and 90 minutes in man.

The invention also relates to a method for preparing a human insulin formulation having an insulin concentration of between 240 and 3000 μM (40 and 500 IU/mL), whose delay of action in man is less than that of the reference formulation at the same insulin concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of between 600 and 1200 μM (100 and 200 IU/mL), whose delay of action in man is less than that of the reference formulation at the same insulin concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 600 μM (100 IU/mL), whose delay of action in man is less than 60 minutes, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 1200 μM (200 IU/mL), whose delay of action in man is at least 10% less than that of the human insulin formulation at the same concentration (200 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 1800 µM (300 IU/mL), whose delay of action in man is at least 10% less than that of the human insulin formulation at the same concentration (300 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 2400 µM (400 IU/mL), whose delay of action in man is at least 10% less than that of the human insulin formulation at the same concentration (400 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 3000 µM (500 IU/mL), whose delay of action in man is at least 10% less than that of the human insulin formulation at the same concentration (500 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention consists in preparing a rapid human insulin formulation, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation at a concentration of 600 µM (100 IU/mL), whose delay of action in man is less than 60 minutes, preferably less than 45 minutes and more preferably less than 30 minutes, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of between 240 and 3000 µM (40 and 500 IU/mL), whose delay of action in man is less than that of the reference formulation at the same insulin concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of between 600 and 1200 µM (100 and 200 IU/mL), whose delay of action in man is less than that of the reference formulation at the same insulin analog concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 600 µmol/L (100 IU/mL), whose delay of action in man is less than 30 minutes, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 1200 µM (200 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 1800 µM (300 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 2400 µM (400 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 3000 µM (500 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention consists in preparing a very rapid insulin analog formulation, characterized in that it comprises a step of adding to said formulation at least one substituted anionic compound, said compound comprising partially substituted carboxyl functional groups, the unsubstituted carboxyl functional groups being salifiable.

In one embodiment, the preparation also comprises a step of adding to said formulation at least one polyanionic compound.

In one embodiment, the insulin is in hexameric form.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the insulin is a recombinant human insulin as described in the European Pharmacopea and the American Pharmacopea.

In one embodiment, the insulin is an insulin analog chosen from the group consisting of the insulin lispro (Humalog®), the insulin aspart (Novolog®, Novorapid®) and the insulin glulisine (Apidra®).

The composition may furthermore be prepared by simple mixing of an aqueous solution of human insulin or of insulin analog and an aqueous solution of substituted anionic compound as a mixture with a polyanionic compound.

In one embodiment, the composition may be prepared by simple mixing of an aqueous solution of human insulin or of insulin analog, an aqueous solution of substituted anionic compound and a polyanionic compound in solution or in lyophilizate form.

In one embodiment, the composition may be prepared by simple mixing of an aqueous solution of human insulin or of insulin analog, a substituted anionic compound in lyophilizate form and a polyanionic compound in solution or in lyophilizate form.

Preferably, this composition is in the form of an injectable solution.

In one embodiment, the concentration of human insulin or insulin analog is between 240 and 3000 µM (40 to 500 IU/mL).

In one embodiment, the concentration of human insulin or insulin analog is between 600 and 3000 µM (100 to 500 IU/mL).

In one embodiment, the concentration of human insulin or insulin analog is between 600 and 2400 µM (100 to 400 IU/mL).

In one embodiment, the concentration of human insulin or insulin analog is between 600 and 1800 µM (100 to 300 IU/mL).

In one embodiment, the concentration of human insulin or insulin analog is between 600 and 1200 µM (100 to 200 IU/mL).

In one embodiment, the concentration of human insulin or insulin analog is 600 µM (100 IU/mL).

In one embodiment, the concentration of human insulin or insulin analog is 1200 µM (200 IU/mL).

In one embodiment, the concentration of human insulin or insulin analog of 600 µM (100 IU/mL) may be reduced by simple dilution, in particular for pediatric applications.

In one embodiment, the concentration of human insulin or insulin analog is 1800 µM (300 IU/mL).

In one embodiment, the concentration of human insulin or insulin analog is 2400 µM (400 IU/mL).

In one embodiment, the concentration of human insulin or insulin analog is 3000 µM (500 IU/mL).

The invention also relates to a pharmaceutical formulation according to the invention, characterized in that it is obtained by drying and/or lyophilization.

In one embodiment, the compositions according to the invention also comprise the addition of zinc salts to a concentration of between 0 and 500 µM.

In one embodiment, the compositions according to the invention also comprise the addition of zinc salts to a concentration of between 0 and 300 µM.

In one embodiment, the compositions according to the invention also comprise the addition of zinc salts to a concentration of between 0 and 200 µM.

In one embodiment, the compositions according to the invention comprise buffers at concentrations of between 0 and 100 mM, preferably between 0 and 50 mM or between 15 and 50 mM.

In one embodiment, the buffer is Tris.

In one embodiment, the compositions according to the invention also comprise preservatives.

In one embodiment, the preservatives are chosen from the group consisting of m-cresol and phenol, alone or as a mixture.

In one embodiment, the concentration of preservatives is between 10 and 50 mM.

In one embodiment, the concentration of preservatives is between 10 and 40 mM.

The compositions according to the invention may also comprise additives such as tonicity agents, for instance glycerol, sodium chloride (NaCl), mannitol and glycine.

The compositions according to the invention may also comprise additives in accordance with the pharmacopeas, for instance surfactants, for example polysorbate.

The compositions according to the invention may also comprise any excipient in accordance with the pharmacopeas which are compatible with the insulins used at the working concentrations.

In the case of local and systemic release, the envisaged modes of administration are intravenous, subcutaneous, intradermal or intramuscular.

Transdermal, oral, nasal, vaginal, ocular, oral and pulmonary administration routes are also envisaged.

The invention also relates to the use of a composition according to the invention for the formulation of a solution of human insulin or insulin analog in a concentration of 100 IU/mL intended for implantable or transportable insulin pumps.

The invention also relates to the use of a composition according to the invention for the formulation of a solution of human insulin or insulin analog in a concentration of 200 IU/mL intended for implantable or transportable insulin pumps.

The invention also relates to substituted anionic compound, in isolated form or as a mixture, chosen from substituted anionic compounds consisting of a saccharide backbone formed from a discrete number u of between 1 and 8 ($1 \leq u \leq 8$) of identical or different saccharide units, linked via identical or different glycoside bonds, said saccharide units being chosen from hexoses, in cyclic form or in open reduced form, characterized in that they are substituted with:

a) at least one substituent of general formula I:

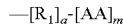   Formula I the substituents being identical or different when there are at least two substituents, in which:
the radical -[AA] denotes an amino acid residue,
the radical —$R_1$— being:
  either a bond and then a $=0$ and the amino acid residue -[AA]- is directly linked to the backbone via a function G,
  or a C2 to C15 carbon-based chain, and then a=1, optionally substituted and/or comprising at least one heteroatom chosen from O, N and S and at least one acid function before the reaction with the amino acid, said chain forming with the amino acid residue -[AA]- an amide function, and is attached to the backbone by means of a function F resulting from a reaction between a hydroxyl function borne by the backbone and a function or substituent borne by the precursor of the radical —$R_1$—,
F is a function chosen from ether, ester and carbamate functions,
G is a carbamate function,
m is equal to 1 or 2,
the degree of substitution of the saccharide units, j, in —[$R_1$]$_a$-[AA]$_m$ being strictly greater than 0 and less than or equal to 6, $0 < j \leq 6$ b) and, optionally, one or more substituents —$R'_1$,
the substituent —$R'_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —$R'_1$,
F' is an ether, ester or carbamate function,
the degree of substitution of the saccharide units, i, in —$R'_1$, being between 0 and 6-j, $0 \leq i \leq 6-j$, and
F and F' are identical or different,
F and G are identical or different,
$i+j \leq 6$,
—$R'_1$ is identical to or different from —$R_1$—,
the free salifiable acid functions borne by the substituent —$R'_1$ are in the form of alkali metal cation salts,
said glycoside bonds, which may be identical or different, being chosen from the group consisting of glycoside bonds of (1,1), (1,2), (1,3), (1,4) or (1,6) type, in an alpha or beta geometry.

In the above formula, the different variables have the values mentioned above.

The substituted anionic compounds according to the invention may be obtained by random grafting of substituents onto the saccharide backbone.

In one embodiment, the substituted anionic compounds chosen from anionic compounds substituted with substituents of formula I or II are characterized in that they may be obtained by grafting substituents in precise positions onto the saccharide units via a process involving steps of protection/deprotection of the alcohol or carboxylic acid groups naturally borne by the backbone. This strategy leads to selective grafting, especially regioselective grafting, of the substituents onto the backbone. The protecting groups include, without limitation, those described in the publication (Wuts, P. G. M. et al., Greene's Protective Groups in Organic Synthesis 2007).

The saccharide backbone may be obtained by degradation of a high molecular weight polysaccharide. The degradation routes include, without limitation, chemical degradation and/or enzymatic degradation.

The saccharide backbone may also be obtained by formation of glycoside bonds between monosaccharide or oligosaccharide molecules using a chemical or enzymatic coupling strategy. The coupling strategies include those described in the publication (Smoot, J. T. et al., Advances in Carbohydrate Chemistry and Biochemistry 2009, 62, 162-250) and in the publication (Lindhorst, T. K., Essentials of Carbohydrate Chemistry and Biochemistry 2007, 157-208). The coupling reactions may be performed in solution or on a solid support. The saccharide molecules before coupling may bear substituents of interest and/or may be functionalized once coupled together, randomly or regioselectively.

Thus, by way of example, the compounds according to the invention may be obtained according to one of the following processes:
  the random grafting of substituents onto a saccharide backbone
  one or more steps of glycosylation between monosaccharide or oligosaccharide molecules bearing substituents
  one or more steps of glycosylation between one or more monosaccharide or oligosaccharide molecules bearing substituents and one or more monosaccharide or oligosaccharide molecules
  one or more steps of introduction of protecting groups onto alcohols or acids naturally borne by the saccharide backbone, followed by one or more substituent grafting reactions and finally a step of removal of the protecting groups
  one or more steps of glycosylation between one or more monosaccharide or oligosaccharide molecules bearing protecting groups on alcohols or acids naturally borne by the saccharide backbone, one or more steps of grafting substituents onto the backbone obtained, and then a step of removal of the protecting groups
  one or more steps of glycosylation between one or more monosaccharide or oligosaccharide molecules bearing protecting groups on alcohols or acids naturally borne by the saccharide backbone, and one or more monosaccharide or oligosaccharide molecules, one or more substituent grafting steps and then a step of removal of the protecting groups.

The compounds according to the invention, isolated or as a mixture, may be separated and/or purified in various ways, especially after having been obtained via the processes described above.

Mention may be made in particular of chromatographic methods, especially "preparative" methods such as:
- flash chromatography, especially on silica, and
- chromatography such as HPLC (high-performance liquid chromatography), in particular RP-HPLC (reverse-phase HPLC).

Selective precipitation methods may also be used.

The invention is illustrated by the examples that follow.

Examples

The structures of the substituted anionic compounds according to the invention are presented in Table 1. The structures of the polysaccharide counterexamples are presented in Table 2.

AA Substituted Anionic Compounds $R=H, R'_1, -[R_1]_a\text{-}[AA]_m$

TABLE 1

| Compound | i | j | Saccharide chain | Substituent —R'$_1$ | Substituent —[R$_1$]$_a$—[AA]$_m$ |
|---|---|---|---|---|---|
| 1 | 0.65 | 1.0 | | CH$_2$COONa | CH$_2$CONH-CH(CH$_2$Ph)-COONa |
| 2 | 1.0 | 0.65 | | CH$_2$COONa | CH$_2$CONH-CH(CH$_2$Ph)-COONa |
| 3 | 0.46 | 1.2 | | CH$_2$COONa | CH$_2$CONH-CH(CH$_2$Ph)-COONa |
| 4 | 0.35 | 0.65 | | CH$_2$COONa | CH$_2$CONH-CH(CH$_2$Ph)-COONa |
| 5 | 1.25 | 0.4 | | CH$_2$COONa | CH$_2$CONH-CH(CH$_2$Ph)-COONa |
| 6 | 0.8 | 0.65 | | CH$_2$COONa | CH$_2$CONH-CH(CH$_2$Ph)-COONa |
| 7 | 2.65 | 0.65 | | CH$_2$COONa | CH$_2$CONH-CH(CH$_2$Ph)-COONa |

TABLE 1-continued

| Compound | i | j | Saccharide chain | Substituent —R'₁ | Substituent —[R₁]ₐ—[AA]ₘ |
|---|---|---|---|---|---|
| 8 | 1.0 | 0.75 | (saccharide structure with subscript 3) | –CH₂–C(=O)–ONa | –CH₂–C(=O)–NH–CH(CH₂–C₆H₅)–C(=O)–ONa |
| 9 | 1.0 | 0.65 | (saccharide structure with subscript 6) | –CH₂–C(=O)–ONa | –CH₂–C(=O)–NH–CH(CH₂–C₆H₅)–C(=O)–ONa |
| 10 | 0.83 | 0.81 | (saccharide structure) | –CH₂–C(=O)–ONa | –CH₂–C(=O)–NH–CH(CH₂–C₆H₄–OH)–C(=O)–ONa |
| 11 | 1.12 | 0.52 | (saccharide structure) | –CH₂–C(=O)–ONa | –CH₂–C(=O)–NH–CH(C₆H₅)–C(=O)–ONa |

AB Polysaccharide Counterexamples

TABLE 2

| Polysaccharide counterexamples | i | j | Saccharide chain | Weight-average molar mass (kg/mol) | Substituent —R'₁ | Substituent —[R₁]ₐ—[AA]ₘ |
|---|---|---|---|---|---|---|
| AB1 | 0.6 | 0.46 | (saccharide structure) | 10 | –CH₂–C(=O)–ONa | –CH₂–C(=O)–NH–CH(CH₂–C₆H₅)–C(=O)–ONa |
| AB2 | 1.01 | 0.64 | (saccharide structure) | 5 | –CH₂–C(=O)–ONa | –CH₂–C(=O)–NH–CH(CH₂–C₆H₅)–C(=O)–ONa |
| AB3 | 0.65 | 0.45 | (saccharide structure) | 5 | –CH₂–C(=O)–ONa | –CH₂–C(=O)–NH–CH(CH₂–C₆H₅)–C(=O)–ONa |

TABLE 2-continued

| Polysaccharide counterexamples | i | j | Saccharide chain | Weight-average molar mass (kg/mol) | Substituent —R'$_1$ | Substituent —[R$_1$]$_a$—[AA]$_m$ |
|---|---|---|---|---|---|---|
| AB4 | 1.01 | 0.64 |  | 10 | 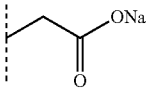 | 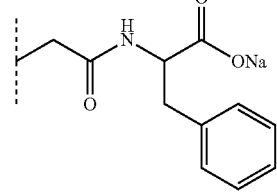 |
| AB5 | 0.45 | 0.65 |  | 5 | 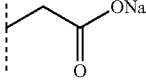 | 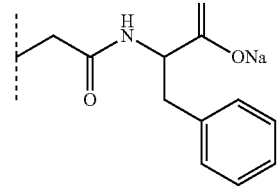 |

Polysaccharide counterexamples AB1, AB2, AB3, AB4 and AB5: R = H, R'$_1$, —[R$_1$]$_a$—[AA]$_m$ AA1. Compound 1: Sodium Maltotriosemethylcarboxylate Functionalized with Sodium L-Phenylalaninate To 8 g (143 mmol of hydroxyl functions) of maltotriose (CarboSynth) dissolved in water at 65° C. is added 0.6 g (16 mmol) of sodium borohydride. After stirring for 30 minutes, 28 g (238 mmol) of sodium chloroacetate are added. To this solution are then added dropwise 24 mL of 10 N NaOH (24 mmol), and the mixture is then heated at 65° C. for 90 minutes. 16.6 g (143 mmol) of sodium chloroacetate are then added to the reaction medium, along with dropwise addition of 14 mL of 10 N NaOH (14 mmol). After heating for 1 hour, the mixture is diluted with water, neutralized with acetic acid and then purified by ultrafiltration on a 1 kDa PES membrane against water. The molecule concentration of the final solution is determined on the dry extract, and an acid/base assay in a 50/50 (V/V) water/acetone mixture is then performed to determine the degree of substitution with methylcarboxylate.

According to the dry extract: [compound]=32.9 mg/g

According to the acid/base assay, the degree of substitution with methylcarboxylate is 1.65 per saccharide unit.

The sodium maltotriosemethylcarboxylate solution is acidified on a Purolite resin (anionic) to obtain maltotriosemethylcarboxylic acid, which is then lyophilized for 18 hours.

10 g of maltotriosemethylcarboxylic acid (63 mmol of methylcarboxylic acid functions) are dissolved in DMF and then cooled to 0° C. A mixture of ethyl phenylalaninate, hydrochloride salt (8.7 g, 38 mmol) in DMF is prepared. 3.8 g of triethylamine (38 mmol) are added to this mixture. A solution of NMM (6.3 g, 63 mmol) and of EtOCOCl (6.8 g, 63 mmol) is then added to the mixture at 0° C. The ethyl phenylalaninate solution is then added and the mixture is stirred at 10° C. An aqueous imidazole solution is added and the mixture is then heated to 30° C. The medium is diluted with water and the solution obtained is then purified by ultrafiltration on a 1 kDa PES membrane against 0.1 N NaOH, 0.9% NaCl and water. The molecule concentration of the final solution is determined on the dry extract. A sample of solution is lyophilized and analyzed by $^1$H NMR in D$_2$O to determine the degree of substitution with methylcarboxylates functionalized with sodium L-phenylalaninate.

According to the dry extract: [compound 1]=29.4 mg/g

According to the acid/base assay, the degree of substitution with sodium methylcarboxylates is 0.65 per saccharide unit.

According to the $^1$H NMR: the degree of substitution with methylcarboxylates functionalized with sodium L-phenylalaninate is 1.0 per saccharide unit.

AA2. Compound 2: Sodium Maltotriosemethylcarboxylate Functionalized with Sodium L-Phenylalaninate Via a process similar to that used for the preparation of compound 1, a sodium maltotriosecarboxylate functionalized with sodium L-phenylalaninate is obtained. According to the acid/base assay, the degree of substitution with sodium methylcarboxylates is 1.0 per saccharide unit.

According to the dry extract: [compound 2]=20.2 mg/g

According to the $^1$H NMR: the degree of substitution with methylcarboxylates functionalized with sodium L-phenylalaninate is 0.65 per saccharide unit.

AA3. Compound 3: Sodium Maltotriosemethylcarboxylate Functionalized with Sodium L-Phenylalaninate Via a process similar to that used for the preparation of compound 1, a sodium maltotriosecarboxylate functionalized with sodium L-phenylalaninate is obtained. According to the acid/base assay, the degree of substitution with sodium methylcarboxylates is 0.46 per saccharide unit.

According to the dry extract: [compound 3]=7.2 mg/g

According to the $^1$H NMR: the degree of substitution with methylcarboxylates functionalized with sodium L-phenylalaninate is 1.2 per saccharide unit.

AA4. Compound 4: Sodium Maltotriosemethylcarboxylate Functionalized with Sodium L-Phenylalaninate Via a process similar to that used for the preparation of compound 1, a sodium maltotriosecarboxylate functionalized with sodium L-phenylalaninate is obtained. According to the acid/base assay, the degree of substitution with sodium methylcarboxylates is 0.35 per saccharide unit.

According to the dry extract: [compound 4]=3.1 mg/g

According to the $^1$H NMR: the degree of substitution with methylcarboxylates functionalized with sodium L-phenylalaninate is 0.65 per saccharide unit.

AA5. Compound 5: Sodium Maltotriosemethylcarboxylate Functionalized with Sodium L-Phenylalaninate Via a process similar to that used for the preparation of compound 1, a sodium maltotriosemethylcarboxylate functionalized with sodium L-phenylalaninate is obtained.

According to the dry extract: [compound 5]=10.9 mg/g

According to the $^1$H NMR: the degree of substitution with methylcarboxylates functionalized with sodium L-phenylalaninate is 0.40 per saccharide unit.

The degree of substitution with sodium methylcarboxylates is 1.25 per saccharide unit.

AA6. Compound 6: Sodium Maltotriosemethylcarboxylate Functionalized with Sodium L-Phenylalaninate To 8 g (143 mmol of hydroxyl functions) of maltotriose (CarboSynth) dissolved in water at 65° C. is added 0.6 g (16 mmol) of sodium borohydride. After stirring for 30 minutes, 28 g (237 mmol) of sodium chloroacetate are added. To this solution are then added dropwise 24 mL of 10 N NaOH (240 mmol). After heating at 65° C. for 90 minutes, the mixture is diluted with water, neutralized by adding acetic acid and then purified by ultrafiltration on a 1 kDa PES membrane against water. The compound concentration of the final solution is determined on the dry extract, and an acid/base assay in a 50/50 (V/V) water/acetone mixture is then performed to determine the degree of substitution with sodium methylcarboxylate.

According to the dry extract: [compound]=14.5 mg/g

According to the acid/base assay, the degree of substitution with sodium methylcarboxylates is 1.45 per saccharide unit.

The sodium maltotriosemethylcarboxylate solution is acidified on a Purolite resin (anionic) to obtain maltotriosemethylcarboxylic acid, which is then lyophilized for 18 hours.

Via a process similar to that used for the preparation of compound 1, a sodium maltotriosemethylcarboxylate functionalized with sodium L-phenylalaninate is obtained.

According to the dry extract: [compound 6]=10.8 mg/g

According to the $^1$H NMR, the degree of substitution with methylcarboxylates functionalized with sodium L-phenylalaninate is 0.65 per saccharide unit.

The degree of substitution with sodium methylcarboxylates is 0.8 per saccharide unit.

AA7. Compound 7: Sodium Maltotriosemethylcarboxylate Functionalized with Sodium L-Phenylalaninate Via a process similar to that described in the preparation of compound 1, 8 g of sodium maltotriosemethylcarboxylate characterized by a degree of substitution with sodium methylcarboxylate of 1.76 are synthesized and lyophilized.

8 g (58 mmol of hydroxyl functions) of the lyophilizate and 15 g (129 mmol) of sodium chloroacetate are dissolved in water at 65° C. To this solution are added dropwise 13 mL of 10 N NaOH (130 mmol) and the mixture is then heated at 65° C. for 90 minutes. 9 g (78 mmol) of sodium chloroacetate are then added to the reaction medium, along with dropwise addition of 8 mL of 10 N NaOH (80 mmol). After heating for 1 hour, the mixture is diluted with water, neutralized with acetic acid and then purified by ultrafiltration on a 1 kDa PES membrane against water. The compound concentration of the final solution is determined on the dry extract, and an acid/base assay in a 50/50 (V/V) water/acetone mixture is then performed to determine the degree of substitution with sodium methylcarboxylates.

According to the dry extract: [compound]=11.7 mg/g

According to the acid/base assay, the degree of substitution with sodium methylcarboxylates is 3.30 per saccharide unit.

The sodium maltotriosemethylcarboxylate solution is acidified on a Purolite resin (anionic) to obtain maltotriosemethylcarboxylic acid, which is then lyophilized for 18 hours.

Via a process similar to that used for the preparation of compound 1, a sodium maltotriosemethylcarboxylate functionalized with sodium L-phenylalaninate is obtained.

According to the dry extract: [compound 7]=14.9 mg/g

According to the $^1$H NMR: the degree of substitution with methylcarboxylates functionalized with sodium L-phenylalaninate is 0.65 per saccharide unit.

The degree of substitution with sodium methylcarboxylates is 2.65 per saccharide unit.

AA8. Compound 8: Sodium Maltopentaosemethylcarboxylate Functionalized with Sodium L-Phenylalaninate Via a process similar to that described for the preparation of compound 1, but performed with maltopentaose (CarboSynth), 10 g of maltopentaosemethylcarboxylic acid with a degree of substitution with methylcarboxylic acid of 1.75 per saccharide unit are obtained and then lyophilized.

Via a process similar to that used for the preparation of compound 1, a sodium maltopentaosemethylcarboxylate functionalized with sodium L-phenylalaninate is obtained.

According to the dry extract: [compound 8]=7.1 mg/g

According to the $^1$H NMR: the degree of substitution with methylcarboxylates functionalized with sodium L-phenylalaninate is 0.75 per saccharide unit.

The degree of substitution with sodium methylcarboxylates is 1.0 per saccharide unit.

AA9. Compound 9: Sodium Maltooctaosemethylcarboxylate Functionalized with Sodium L-Phenylalaninate Via a process similar to that described for the preparation of compound 1, but performed with maltooctaose (CarboSynth), 10 g of maltooctaosemethylcarboxylic acid with a degree of substitution with methylcarboxylic acid of 1.65 per saccharide unit are obtained and then lyophilized.

Via a process similar to that used for the preparation of compound 1, a sodium maltooctaosemethylcarboxylate functionalized with sodium L-phenylalaninate is obtained.

According to the dry extract: [compound 9]=26.3 mg/g

According to the $^1$H NMR: the degree of substitution with methylcarboxylates functionalized with sodium L-phenylalaninate is 0.65 per saccharide unit.

The degree of substitution with sodium methylcarboxylates is 1.0 per saccharide unit.

AA10. Compound 10: Sodium Maltotriosemethylcarboxylate Functionalized with Sodium L-Tyrosinate Via a process similar to that described for the preparation of compound 1, but performed with methyl L-tyrosinate, hydrochloride salt (Bachem), a sodium maltotriosemethylcarboxylate, characterized by a degree of substitution with sodium methylcarboxylate per saccharide unit of 1.64, is functionalized with sodium L-tyrosinate.

According to the dry extract: [compound 10]=9.1 mg/g

According to the $^1$H NMR: the degree of substitution with methylcarboxylates functionalized with sodium L-tyrosinate is 0.81 per saccharide unit.

The degree of substitution with sodium methylcarboxylates is 0.83 per saccharide unit.

AA11. Compound 11: Sodium Maltotriosemethylcarboxylate Functionalized with Sodium Alpha-Phenylglycinate Via a process similar to that described for the preparation of compound 1, 10 g of maltotriosemethylcarboxylic acid with a degree of substitution with methylcarboxylic acid of 1.64 per saccharide unit are obtained and then lyophilized.

8 g of maltotriosemethylcarboxylic acid (50 mmol of methylcarboxylic acid functions) are dissolved in DMF and then cooled to 0° C. A mixture of sodium alpha-phenylglycinate (Bachem, 5 g; 33 mmol) and triethylamine (33 mmol) is prepared in water. A solution of NMM (4.9 g; 49 mmol) and of EtOCOCl (5.3 g, 49 mmol) is then added to the solution of maltotriosemethylcarboxylic acid at 0° C. The solution of sodium alpha-phenylglycinate and triethylamine is then added and the mixture is stirred at 30° C. An aqueous imidazole solution (340 g/L) is added after 90 minutes. The medium is diluted with water and the solution obtained is then purified by ultrafiltration on a 1 kDa PES membrane against a 150 mM NaHCO$_3$/Na$_2$CO$_3$ pH 10.4 buffer, 0.9% NaCl and water. The compound concentration of the final solution is determined on the dry extract. A sample of solution is lyophilized and analyzed by $^1$H NMR in D$_2$O to determine the degree of substitution with methylcarboxylates functionalized with sodium alpha-phenylglycinate.

According to the dry extract: [compound 11]=9.1 mg/g

According to the $^1$H NMR: the degree of substitution with methylcarboxylates functionalized with sodium alpha-phenylglycinate is 0.52 per saccharide unit.

The degree of substitution with sodium methylcarboxylates is 1.12 per saccharide unit.

AB Polysaccharide Counterexamples

AB1. Polysaccharide 1: Sodium Dextranmethylcarboxylate Functionalized with Sodium L-Phenylalaninate Polysaccharide 1 is a sodium dextranmethylcarboxylate functionalized with sodium L-phenylalaninate obtained from a dextran with a weight-average molar mass of 10 kg/mol (DP=39, Pharmacosmos) according to the process described in patent application FR 07/02316 published under the number FR 2 914 305. According to the acid/base assay, the degree of substitution with sodium methylcarboxylates is 0.6 per saccharide unit.

According to the $^1$H NMR: the degree of substitution with methylcarboxylates functionalized with sodium L-phenylalaninate is 0.46 per saccharide unit.

This polysaccharide corresponds to polysaccharide 1 of patent application FR 09/01478.

AB2. Polysaccharide 2: Sodium Dextranmethylcarboxylate Functionalized with Sodium L-Phenylalaninate Polysaccharide 2 is a sodium dextranmethylcarboxylate functionalized with sodium L-phenylalaninate obtained from a dextran with a weight-average molar mass of 5 kg/mol (DP=19, Pharmacosmos) according to the process described in patent application FR 07/02316 published under the number FR 2 914 305. According to the acid/base assay, the degree of substitution with sodium methylcarboxylates is 1.01 per saccharide unit.

According to the $^1$H NMR: the degree of substitution with methylcarboxylates functionalized with sodium L-phenylalaninate is 0.64 per saccharide unit.

AB3. Polysaccharide 3: Sodium Dextranmethylcarboxylate Functionalized with Sodium L-Phenylalaninate Polysaccharide 3 is a sodium dextranmethylcarboxylate functionalized with sodium L-phenylalaninate obtained from a dextran with a weight-average molar mass of kg/mol (DP=19, Pharmacosmos) according to the process described in patent application FR 07/02316 published under the number FR 2 914 305. According to the acid/base assay, the degree of substitution with sodium methylcarboxylates is 0.65 per saccharide unit.

According to the $^1$H NMR: the degree of substitution with methylcarboxylates functionalized with sodium L-phenylalaninate is 0.45 per saccharide unit.

AB4. Polysaccharide 4: Sodium Dextranmethylcarboxylate Functionalized with Sodium L-Phenylalaninate Polysaccharide 4 is a sodium dextranmethylcarboxylate functionalized with sodium L-phenylalaninate obtained from a dextran with a weight-average molar mass of 10 kg/mol (DP=39, Pharmacosmos) according to the process described in patent application FR 07/02316 published under the number FR 2 914 305. According to the acid/base assay, the degree of substitution with sodium methylcarboxylates is 1.01 per saccharide unit.

According to the $^1$H NMR: the degree of substitution with methylcarboxylates functionalized with sodium L-phenylalaninate is 0.64 per saccharide unit.

AB5. Polysaccharide 5: Sodium Dextranmethylcarboxylate Functionalized with Sodium L-Phenylalaninate Polysaccharide 5 is a sodium dextranmethylcarboxylate functionalized with sodium L-phenylalaninate obtained from a dextran with a weight-average molar mass of 5 kg/mol (DP=19, Pharmacosmos) according to the process described in patent application FR 07/02316 published under the number FR 2 914 305. According to the acid/base assay, the degree of substitution with sodium methylcarboxylates is 0.45 per saccharide unit.

According to the $^1$H NMR: the degree of substitution with methylcarboxylates functionalized with sodium L-phenylalaninate is 0.65 per saccharide unit.

AC Polyanionic Compound

Polyanionic Compound 1: Sodium Maltotriosemethylcarboxylate

To 8 g (143 mmol of hydroxyl functions) of maltotriose (CarboSynth) dissolved in water at 65° C. is added 0.6 g (16 mmol) of sodium borohydride. After stirring for 30 minutes, 28 g (238 mmol) of sodium chloroacetate are added. To this solution are then added dropwise 24 mL of 10 N NaOH (240 mmol), and the mixture is then heated at 65° C. for 90 minutes. 16.6 g (143 mmol) of sodium chloroacetate are then added to the reaction medium, along with dropwise addition of 14 mL of 10 N NaOH (140 mmol). After heating for 1 hour, the mixture is diluted with water, neutralized with acetic acid and then purified by ultrafiltration on a 1 kDa PES membrane against water. The compound concentration of the final solution is determined on the dry extract, and an acid/base assay in a 50/50 (V/V) water/acetone mixture is then performed to determine the degree of substitution with sodium methylcarboxylate.

According to the dry extract: [polyanionic compound 1]=32.9 mg/g

According to the acid/base assay: the degree of substitution with sodium methylcarboxylates is 1.65 per saccharide unit.

B Preparation of the Solutions

B1. Solution of Rapid Insulin Analog Novolog® at 100 IU/mL

This solution is a commercial solution of aspart insulin from Novo Nordisk sold under the name Novolog®. This product is an aspart rapid insulin analog.

B2. Solution of Rapid Insulin Analog Humalog® at 100 IU/mL

This solution is a commercial solution of lispro insulin from Eli Lilly sold under the name Humalog®. This product is a rapid insulin analog.

B3. Solution of Regular Human Insulin Actrapid® at 100 IU/mL

This solution is a commercial solution of human insulin from Novo Nordisk sold under the name Actrapid®. This product is a regular human insulin.

B4. Solution of Regular Human Insulin Humulin® R at 100 IU/mL

This solution is a commercial solution of human insulin from Eli Lilly sold under the name Humulin® R. This product is a regular human insulin.

B5. Preparation of the Excipient Solutions

The non-polymeric polyanionic compounds are selected by measuring their dissociation constant with respect to calcium ions and with respect to their capacity for not destabilizing the hexameric form of insulin.

As regards the dissociation constant with respect to calcium ions, it is determined as follows.

Solutions containing 2.5 mM of $CaCl_2$, 150 mM of NaCl and increasing concentrations of polyanionic compound (between 0 and 20 mM) are prepared. The potential of all these formulations is measured and the concentrations of free calcium ions in the formulations are determined. After linearization by the Scatchard method, the dissociation constants are established. These data make it possible to compare the affinity of the carboxylates and phosphates of the various polyanionic compounds for Ca.

As regards their capacity for not destabilizing the hexameric form of insulin, this property is measured by circular dichroism in comparison with insulin alone (without anionic compound or polyanionic compound), see the experimental protocols in experimental section D.

Preparation of a Sodium Citrate Solution at 1.188 M

A sodium citrate solution is obtained by dissolving 9.0811 g of sodium citrate (30.9 mmol) in 25 mL of water in a graduated flask. The pH is adjusted to exactly 7.4 by adding 1 mL of 1 M HCl. The solution is filtered through a 0.22 μm filter.

Preparation of a 130 mM m-Cresol Solution

An m-cresol solution is obtained by dissolving 14.114 g of m-cresol (130 mmol) in 986.4 mL of water in a 1 L graduated flask.

Preparation of a Solution of m-Cresol and Glycerol (96.6 mM m-Cresol and 566 mM Glycerol)

73.3 g of the 130 mM m-cresol solution are added to 5.26 g of glycerol and then diluted by addition of 22.25 g of water. The m-cresol and glycerol solution obtained is homogenized for 30 minutes and then filtered through a 0.22 μm membrane.

Preparation of a 32.7 mM Tween 20 Solution

A Tween 20 solution is obtained by dissolving 2.0079 g of Tween 20 (1.636 mmol) in 50 mL of water in a graduated flask. The solution is filtered through a 0.22 μm membrane.

B6. Preparation of a 500 IU/mL Human Insulin Solution 15 g of water are added to 563.6 mg of human insulin and the pH is then lowered to acidic pH by adding 5.98 g of 0.1 N HCl. After total dissolution of the insulin at acidic pH, the solution is neutralized to pH 7.2 by adding 8.3 mL of 0.1 N NaOH. The concentration is then adjusted to 500 IU/mL by adding 0.76 g of water. The solution is finally filtered through a 0.22 μm membrane.

B7. Preparation of a 100 IU/mL Lispro Insulin Solution in the Presence of Compound 1

For a final volume of 100 mL of formulation, with a [compound 1]/[lispro insulin] mass ratio of 2.0, the various reagents are added in the amounts specified below and in the following order:

| Lyophilized compound 1 | 730 mg |
| 100 IU/mL Humalog ® commercial solution | 100 mL |

The final pH is adjusted to 7.4±0.4.

The clear solution is filtered through a 0.22 μm membrane and stored at 4° C.

B8. Preparation of a 100 IU/mL Lispro Insulin Solution in the Presence of Compound 1 and Citrate For a final volume of 100 mL of formulation, with a [compound 1]/[lispro insulin] mass ratio of 2.0 and a citrate concentration of 9.3 mM, the various reagents are added in the amounts specified below and in the following order:

| Lyophilized compound 1 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B9. Preparation of a 100 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2.0/2.0/1, the various reagents are added in the amounts specified below and in the following order:

| Lyophilized compound 1 | 730 mg |
| Lyophilized polyanionic compound 1 | 730 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B10. Preparation of a 100 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2.0/5.5/1, the various reagents are added in the amounts specified below and in the following order:

| Lyophilized compound 1 | 730 mg |
| Lyophilized polyanionic compound 1 | 2000 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B11. Preparation of a 100 IU/mL Lispro Insulin Solution in the Presence of Compound 2 and Citrate For a final volume of 100 mL of formulation, with a [compound 2]/[lispro insulin] mass ratio of 2.0 and a citrate concentration of 9.3 mM, the various reagents are added in the amounts specified below and in the following order:

| | |
|---|---|
| Lyophilized compound 2 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B12. Preparation of a 100 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2.0/2.0/1, the various reagents are added in the amounts specified below and in the following order:

| | |
|---|---|
| Lyophilized compound 2 | 730 mg |
| Lyophilized polyanionic compound 1 | 730 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B13. Preparation of a 100 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2.0/5.5/1, the various reagents are added in the amounts specified below and in the following order:

| | |
|---|---|
| Lyophilized compound 2 | 730 mg |
| Lyophilized polyanionic compound 1 | 2000 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B14. Preparation of a 100 IU/mL Lispro Insulin Solution in the Presence of Compound 1

For a final volume of 100 mL of formulation, with a [compound 1]/[lispro insulin] mass ratio of 4, the various reagents are added in the amounts specified below:

| | |
|---|---|
| Compound 1 in lyophilized form | 1460 mg |
| 100 IU/mL Humalog ® commercial solution | 100 mL |

The final pH is adjusted to 7.4±0.4. The clear solution is filtered through a 0.22 µm membrane and stored at 4° C.

B15. Preparation of a 100 IU/mL Lispro Insulin Solution in the Presence of Compound 2

For a final volume of 100 mL of formulation, with a [compound 2]/[lispro insulin] mass ratio of 4, the various reagents are added in the amounts specified below:

| | |
|---|---|
| Compound 2 in lyophilized form | 1460 mg |
| 100 IU/mL Humalog ® commercial solution | 100 mL |

The final pH is adjusted to 7.4±0.4. The clear solution is filtered through a 0.22 µm membrane and stored at 4° C.

B16. Preparation of a 100 IU/mL Lispro Insulin Analog Solution in the Presence of compound 1 and sodium tartrate For a final volume of 100 mL of formulation, with a [compound 1]/[lispro insulin] mass ratio of 2.0 and a sodium tartrate concentration of 80 mM, the various reagents are added in the amounts specified below:

| | |
|---|---|
| Compound 1 in lyophilized form | 730 mg |
| 100 IU/mL Humalog ® commercial solution | 100 mL |
| Sodium tartrate | 1.552 g |

For the tartrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B17. Preparation of a 100 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2/4/1, the various reagents are added in the amounts specified below:

| | |
|---|---|
| Compound 1 in lyophilized form | 730 mg |
| Polyanionic compound 1 in lyophilized form | 1460 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B18. Preparation of a 100 IU/mL Lispro Insulin Solution in the Presence of Compound 1 and Sodium Triphosphate For a final volume of 100 mL of formulation, the various reagents are added in the amounts specified below:

| | |
|---|---|
| Compound 1 in lyophilized form | 730 mg |
| Sodium triphosphate | 184 mg |
| 100 IU/mL Humalog ® commercial solution | 100 mL |

For the triphosphate, use may be made of the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B19. Preparation of a 100 IU/mL Lispro Insulin Analog Solution in the Presence of Compound 2 and Sodium Tartrate For a final volume of 100 mL of formulation, with a [compound 2]/[lispro insulin] mass ratio of 2.0 and a sodium tartrate concentration of 80 mM, the various reagents are added in the amounts specified below:

| | |
|---|---|
| Compound 2 in lyophilized form | 730 mg |
| 100 IU/mL Humalog ® commercial solution | 100 mL |
| Sodium tartrate | 1.552 g |

For the tartrate, use may be made of the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B20. Preparation of a 100 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2/4/1, the various reagents are added in the amounts specified below:

| | |
|---|---|
| Compound 2 in lyophilized form | 730 mg |
| Polyanionic compound 1 in lyophilized form | 1460 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B21. Preparation of a 100 IU/mL Lispro Insulin Solution in the Presence of Compound 2 and Sodium Triphosphate For a final volume of 100 mL of formulation, the various reagents are added in the amounts specified below:

| | |
|---|---|
| Compound 2 in lyophilized form | 730 mg |
| Sodium triphosphate | 184 mg |
| 100 IU/mL Humalog ® commercial solution | 100 mL |

For the triphosphate, use may be made of the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B22. Preparation of a 200 IU/mL Insulin Analog (Lispro Insulin) Solution

The commercial formulation of lispro insulin (Humalog®) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated lispro insulin solution was adjusted to 200 IU/mL by adding the commercial lispro insulin formulation (Humalog®). The concentrated lispro insulin formulation has the same concentrations of excipients (m-cresol, glycerol, phosphate) as the commercial formulation at 100 IU/mL.

The final pH is adjusted to 7.4±0.4. The clear solution is filtered through a 0.22 μm membrane and stored at 4° C.

B23. Preparation of a 200 IU/mL Lispro Insulin Solution in the Presence of Compound 1 and Citrate For a final volume of 100 mL of formulation, with a [compound 1]/[lispro insulin] mass ratio of 2, the various reagents are mixed in the amounts specified below:

| | |
|---|---|
| 200 IU/mL lispro insulin | 100 mL |
| Lyophilizate of compound 1 | 1460 mg |
| 1.188M sodium citrate solution | 1566 μL |

The final pH is adjusted to 7.4±0.4. The clear solution is filtered through a 0.22 μm membrane and stored at 4° C.

B24. Preparation of a 200 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2/2/1, the various reagents are mixed in the amounts specified below:

| | |
|---|---|
| 200 IU/mL lispro insulin | 100 mL |
| Lyophilizate of compound 1 | 1460 mg |
| Lyophilizate of polyanionic compound 1 | 1460 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B25. Preparation of a 200 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2/4/1, the various reagents are mixed in the amounts specified below:

| | |
|---|---|
| 200 IU/mL lispro insulin | 100 mL |
| Lyophilizate of compound 1 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B26. Preparation of a 200 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2/4/1, the various reagents are mixed in the amounts specified below:

| | |
|---|---|
| 200 IU/mL lispro insulin | 100 mL |
| Lyophilizate of compound 2 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B27. Preparation of a 100 IU/mL Human Insulin Solution in the Presence of Compound 1 and Tartrate For a final volume of 100 mL of formulation, with a [compound 1]/[human insulin] mass ratio of 2 and 80 mM of tartrate, the various reagents are mixed in the amounts specified below:

| | |
|---|---|
| 500 IU/mL human insulin | 20 mL |
| 36.01 mg/mL solution of compound 1 | 20.27 mL |
| 96.6 mM m-cresol/566 mM glycerol solution | 30 mL |
| Water | 28.95 mL |
| Sodium tartrate | 1.552 g |

For the tartrate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B28. Preparation of a 100 IU/mL Human Insulin Solution in the Presence of Compound 1 and Triphosphate For a final volume of 100 mL of formulation, the various reagents are mixed in the amounts specified below:

| | |
|---|---|
| 500 IU/mL human insulin | 20 mL |
| 36.01 mg/mL solution of compound 1 | 20.27 mL |
| 96.6 mM m-cresol/566 mM glycerol solution | 30 mL |
| Water | 28.95 mL |
| Sodium triphosphate | 184 mg |

For the triphosphate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B29. Preparation of a 100 IU/mL Human Insulin Solution in the Presence of Compound 2 and Tartrate For a final volume of 100 mL of formulation, with a [compound 2]/[human insulin] mass ratio of 2 and 80 mM of tartrate, the various reagents are mixed in the amounts specified below:

| | |
|---|---|
| 500 IU/mL human insulin | 20 mL |
| 36.01 mg/mL solution of compound 2 | 20.27 mL |
| 96.6 mM m-cresol/566 mM glycerol solution | 30 mL |
| Water | 28.95 mL |
| Sodium tartrate | 1.552 g |

For the tartrate, use may be made of the acid form or the basic form in the form of the sodium salt, the potassium salt or another salt that is compatible with an injectable formulation.

The final pH is 7.4±0.4.

This clear solution is filtered through a 0.22 μm membrane and then placed at +4° C.

B30. Preparation of a 100 IU/mL Human Insulin Solution in the Presence of Compound 2 and Triphosphate For a final volume of 100 mL of formulation, the various reagents are mixed in the amounts specified below:

| | |
|---|---|
| 500 IU/mL human insulin | 20 mL |
| 36.01 mg/mL solution of compound 2 | 20.27 mL |
| 96.6 mM m-cresol/566 mM glycerol solution | 30 mL |
| Water | 28.95 mL |
| Sodium triphosphate | 184 mg |

For the triphosphate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B31. Preparation of a 200 IU/mL Human Insulin Solution

The commercial formulation of human insulin (Humulin® R) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated human insulin solution was adjusted to 200 IU/mL by adding the commercial human insulin formulation (Humulin® R). The concentrated human insulin formulation has the same concentrations of excipients (m-cresol, glycerol) as the commercial formulation at 100 IU/mL.

The final pH is adjusted to 7.4±0.4. The clear solution is filtered through a 0.22 μm membrane and stored at 4° C.

B32. Preparation of a 200 IU/mL Human Insulin Solution in the Presence of Compound 1 and Citrate For a final volume of 100 mL of formulation, with a [compound 1]/[human insulin] mass ratio of 2, the various reagents are mixed in the amounts specified below:

| | |
|---|---|
| 200 IU/mL human insulin | 100 mL |
| Lyophilizate of compound 1 | 1460 mg |
| 1.188M sodium citrate solution | 1566 μL |

The final pH is adjusted to 7.4±0.4. The clear solution is filtered through a 0.22 μm membrane and stored at 4° C.

B33. Preparation of a 200 IU/mL Human Insulin Solution in the Presence of Compound 1 and the Polyanionic Compound 1

For a final volume of 100 mL of formulation, with a [compound 1]/[polyanionic compound 1]/[human insulin] mass ratio of 2/2/1, the various reagents are mixed in the amounts specified below:

| | |
|---|---|
| 200 IU/mL human insulin | 100 mL |
| Lyophilizate of compound 1 | 1460 mg |
| Lyophilizate of polyanionic compound 1 | 1460 mg |

The final pH is adjusted to 7.4±0.4. The clear solution is filtered through a 0.22 μm membrane and stored at 4° C.

B34. Preparation of a 200 IU/mL Human Insulin Solution in the Presence of Compound 1 and the Polyanionic Compound 1

For a final volume of 100 mL of formulation, with a [compound 1]/[polyanionic compound 1]/[human insulin] mass ratio of 2/4/1, the various reagents are mixed in the amounts specified below:

| | |
|---|---|
| 200 IU/mL human insulin | 100 mL |
| Lyophilizate of compound 1 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B35. Preparation of a 200 IU/mL Human Insulin Solution in the Presence of Compound 2 and Citrate For a final volume of 100 mL of formulation, with a [compound 2]/[human insulin] mass ratio of 2, the various reagents are mixed in the amounts specified below:

| | |
|---|---|
| 200 IU/mL human insulin | 100 mL |
| Lyophilizate of compound 2 | 1460 mg |
| 1.188M sodium citrate solution | 1566 μL |

The final pH is adjusted to 7.4±0.4. The clear solution is filtered through a 0.22 μm membrane and stored at 4° C.

B36. Preparation of a 200 IU/mL Human Insulin Solution in the Presence of Compound 2 and the Polyanionic Compound 1

For a final volume of 100 mL of formulation, with a [compound 2]/[polyanionic compound 1]/[human insulin] mass ratio of 2/2/1, the various reagents are mixed in the amounts specified below:

| | |
|---|---|
| 200 IU/mL human insulin | 100 mL |
| Lyophilizate of compound 2 | 1460 mg |
| Lyophilizate of polyanionic compound 1 | 1460 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B37. Preparation of a 200 IU/mL Human Insulin Solution in the Presence of Compound 2 and the Polyanionic Compound 1

For a final volume of 100 mL of formulation, with a [compound 2]/[polyanionic compound 1]/[human insulin] mass ratio of 2/4/1, the various reagents are mixed in the amounts specified below:

| | |
|---|---|
| 200 IU/mL human insulin | 100 mL |
| Lyophilizate of compound 2 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B38. Preparation of a 100 IU/mL Human Insulin Solution in the Presence of Compound 2 and Citrate For a final volume of 100 mL of formulation, with a [compound 2]/[human insulin] mass ratio of 2 and 9.3 mM of citrate, the various reagents are mixed in the amounts specified below:

| | |
|---|---|
| 500 IU/mL human insulin | 20 mL |
| 36.01 mg/mL solution of compound 2 | 20.27 mL |
| 96.6 mM m-cresol/566 mM glycerol solution | 30 mL |
| Water | 28.95 mL |
| 1.188M sodium citrate solution | 783 μL |

For the citrate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B39. Preparation of a 100 IU/mL Human Insulin Solution in the Presence of Compound 1 and Citrate For a final volume of 100 mL of formulation, with a [compound 1]/[human insulin] mass ratio of 2 and 9.3 mM of citrate, the various reagents are mixed in the amounts specified below:

| | |
|---|---|
| 500 IU/mL human insulin | 20 mL |
| 36.01 mg/mL solution of compound 1 | 27 mL |
| 96.6 mM m-cresol/566 mM glycerol solution | 30 mL |
| Water | 28.95 mL |
| 1.188M sodium citrate solution | 783 μL |

For the citrate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B40. Preparation of a 100 IU/mL Aspart Insulin Solution in the Presence of Compound 1 and Citrate For a final volume of 100 mL of formulation, with a [compound 1]/[aspart insulin] mass ratio of 2.0 and a citrate concentration of 9.3 mM, the various reagents are added in the amounts specified below and in the following order:

| | |
|---|---|
| Lyophilized compound 1 | 730 mg |
| 100 IU/mL Novolog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B41. 100 IU/mL Solution of Rapid Insulin Analog Apidra®

This solution is a commercial solution of glulisine insulin from Sanofi-Aventis sold under the name Apidra®. This product is a rapid insulin analog.

B42. Preparation of a 100 IU/mL Glulisine Insulin Solution in the Presence of Compound 1 and Citrate For a final volume of 100 mL of formulation, with a [compound 1]/[glulisine insulin] mass ratio of 2.0 and a citrate concentration of 9.3 mM, the various reagents are added in the amounts specified below and in the following order:

| | |
|---|---|
| Lyophilized compound 1 | 730 mg |
| 100 IU/mL Apidra ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B43. Preparation of a 100 IU/mL Aspart Insulin Solution in the Presence of Compound 2 and Citrate For a final volume of 100 mL of formulation, with a [compound 2]/[aspart insulin] mass ratio of 2.0 and a citrate concentration of 9.3 mM, the various reagents are added in the amounts specified below and in the following order:

| | |
|---|---|
| Lyophilized compound 2 | 730 mg |
| 100 IU/mL Novolog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B44. Preparation of a 100 IU/mL Glulisine Insulin Solution in the Presence of Compound 2 and Citrate For a final volume of 100 mL of formulation, with a [compound 2]/[glulisine insulin] mass ratio of 2.0 and a citrate concentration of 9.3 mM, the various reagents are added in the amounts specified below and in the following order:

| | |
|---|---|
| Lyophilized compound 2 | 730 mg |
| 100 IU/mL Apidra ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B45. Preparation of a 100 IU/mL Lispro Insulin Solution in the Presence of Compound 5 and Citrate For a final volume of 100 mL of formulation, with a [compound 5]/[lispro insulin] mass ratio of 2.0 and a citrate concentration of 9.3 mM, the various reagents are added in the amounts specified below and in the following order:

| | |
|---|---|
| Lyophilized compound 5 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B46. Preparation of a 100 IU/mL Lispro Insulin Solution in the Presence of Compound 6 and Citrate For a final volume of 100 mL of formulation, with a [compound 6]/[lispro insulin] mass ratio of 2.0 and a citrate concentration of 9.3 mM, the various reagents are added in the amounts specified below and in the following order:

| | |
|---|---|
| Lyophilized compound 6 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B47. Preparation of a 100 IU/mL Lispro Insulin Solution in the Presence of Compound 7 and Citrate For a final volume of 100 mL of formulation, with a [compound 7]/[lispro insulin] mass ratio of 2.0 and a citrate concentration of 9.3 mM, the various reagents are added in the amounts specified below and in the following order:

| | |
|---|---|
| Lyophilized compound 7 | 730 mg |
| 100 IU/mL Humalog commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B48. Preparation of a 100 IU/mL Lispro Insulin Solution in the Presence of Compound 8 and Citrate For a final volume of 100 mL of formulation, with a [compound 8]/[lispro insulin] mass ratio of 2.0 and a citrate concentration of 9.3 mM, the various reagents are added in the amounts specified below and in the following order:

| | |
|---|---|
| Lyophilized compound 8 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B49. Preparation of a 100 IU/mL Lispro Insulin Solution in the Presence of Compound 9 and Citrate For a final volume of 100 mL of formulation, with a [compound 9]/[lispro insulin] mass ratio of 2.0 and a citrate concentration of 9.3 mM, the various reagents are added in the amounts specified below and in the following order:

| | |
|---|---|
| Lyophilized compound 9 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

B50. Preparation of a 100 IU/mL Human Insulin Solution in the Presence of Compound 5 and Citrate For a final volume of 100 mL of formulation, with a [compound 5]/[human insulin] mass ratio of 2.0 and a citrate concentration of 9.3 mM, the various reagents are added in the amounts specified below and in the following order:

| | |
|---|---|
| Lyophilized compound 5 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B51. Preparation of a 100 IU/mL Human Insulin Solution in the Presence of Compound 6 and Citrate For a final volume of 100 mL of formulation, with a [compound 6]/[human insulin] mass ratio of 2.0 and a citrate concentration of 9.3 mM, the various reagents are added in the amounts specified below and in the following order:

| | |
|---|---|
| Lyophilized compound 6 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B52. Preparation of a 100 IU/mL Human Insulin Solution in the Presence of Compound 7 and Citrate For a final volume of 100 mL of formulation, with a [compound 7]/[human insulin] mass ratio of 2.0 and a citrate concentration of 9.3 mM, the various reagents are added in the amounts specified below and in the following order:

| | |
|---|---|
| Lyophilized compound 7 | 730 mg |
| 100 IU/mL Humulin ® R commercia solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B53. Preparation of a 100 IU/mL Human Insulin Solution in the Presence of Compound 8 and Citrate For a final volume of 100 mL of formulation, with a [compound 8]/[human insulin] mass ratio of 2.0 and a citrate concentration of 9.3 mM, the various reagents are added in the amounts specified below and in the following order:

| | |
|---|---|
| Lyophilized compound 8 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B54. Preparation of a 100 IU/mL Human Insulin Solution in the Presence of Compound 9 and Citrate For a final volume of 100 mL of formulation, with a [compound 9]/[human insulin] mass ratio of 2.0 and a citrate concentration of 9.3 mM, the various reagents are added in the amounts specified below and in the following order:

| | |
|---|---|
| Lyophilized compound 9 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B55. Preparation of a 100 IU/mL Human Insulin Solution in the Presence of Compound 2

For a final volume of 100 mL of formulation, with a [compound 2]/[human insulin] mass ratio of 2.0, the various reagents are added in the amounts specified below and in the following order:

| | |
|---|---|
| Lyophilized compound 2 | 730 mg |
| 100 IU/mL Humulin ® R commercial solution | 100 mL |

The final pH is adjusted to 7.4±0.4.

The clear solution is filtered through a 0.22 μm membrane and stored at 4° C.

B56. Preparation of a 100 IU/mL Human Insulin Solution in the Presence of Compound 7

For a final volume of 100 mL of formulation, with a [compound 7]/[human insulin] mass ratio of 2.0, the various reagents are added in the amounts specified below and in the following order:

| | |
|---|---|
| Lyophilized compound 7 | 730 mg |
| 100 IU/mL Humulin ® R commercial solution | 100 mL |

The final pH is adjusted to 7.4±0.4.

The clear solution is filtered through a 0.22 μm membrane and stored at 4° C.

B57. Preparation of a 100 IU/mL Lispro Insulin Solution in the Presence of Compound 10 and Citrate For a final volume of 100 mL of formulation, with a [compound 10]/[lispro insulin] mass ratio of 2.0 and a citrate concentration of 9.3 mM, the various reagents are added in the amounts specified below and in the following order:

| | |
|---|---|
| Lyophilized compound 10 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B58. Preparation of a 100 IU/mL Lispro Insulin Solution in the Presence of Compound 11 and Citrate For a final volume of 100 mL of formulation, with a [compound 11]/[lispro insulin] mass ratio of 2.0 and a citrate concentration of 9.3 mM, the various reagents are added in the amounts specified below and in the following order:

| | |
|---|---|
| Lyophilized compound 11 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

B59. Preparation of a 100 IU/mL Human Insulin Solution in the Presence of Compound 10 and Citrate For a final volume of 100 mL of formulation, with a [compound 10]/[human insulin] mass ratio of 2.0 and a citrate concentration of 9.3 mM, the various reagents are added in the amounts specified below and in the following order:

| | |
|---|---|
| Lyophilized compound 10 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B60. Preparation of a 100 IU/mL Human Insulin Solution in the Presence of Compound 11 and Citrate For a final volume of 100 mL of formulation, with a [compound 11]/[human insulin] mass ratio of 2.0 and a citrate concentration of 9.3 mM, the various reagents are added in the amounts specified below and in the following order:

| | |
|---|---|
| Lyophilized compound 11 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B61. Preparation of a 200 IU/mL Aspart Insulin Solution

The commercial formulation of aspart insulin (Novolog®) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated aspart insulin solution was adjusted to 200 IU/mL by adding the commercial aspart insulin formulation (Novolog®). The concentrated aspart insulin formulation has the same concentrations of excipients (m-cresol, glycerol) as the commercial formulation at 100 IU/mL.

By modifying the centrifugation time and the final dilution with the commercial formulation, it is possible to prepare in the same manner aspart insulin formulations at 300, 400 or 500 IU/mL.

The final pH is adjusted to 7.4±0.4. The clear solution is filtered through a 0.22 μm membrane and stored at 4° C.

B62. Preparation of a 200 IU/mL Glulisine Insulin Solution

The commercial formulation of glulisine insulin (Apidra®) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated glulisine insulin solution was adjusted to 200 IU/mL by adding the commercial glulisine insulin formulation (Apidra®). The concentrated glulisine insulin formulation has the same concentrations of excipients (m-cresol, NaCl, TRIS) as the commercial formulation at 100 IU/mL.

By modifying the centrifugation time and the final dilution with the commercial formulation, it is possible to prepare in the same manner glulisine insulin formulations at 300, 400 or 500 IU/mL.

The final pH is adjusted to 7.4±0.4. The clear solution is filtered through a 0.22 μm membrane and stored at 4° C.

B63. Preparation of a 200 IU/mL Aspart Insulin Solution in the Presence of Compound 1 at 14.6 mg/mL and 18.6 mM Citrate For a final volume of 100 mL of formulation, with a [compound 1]/[aspart insulin] mass ratio of 2.0, the various reagents are mixed in the amounts specified below and in the following order:

| | |
|---|---|
| Lyophilizate of compound 1 | 1460 mg |
| 200 IU/mL aspart insulin | 100 mL |
| 1.188M sodium citrate solution | 1566 μL |

The final pH is adjusted to 7.4±0.4. The clear solution is filtered through a 0.22 μm membrane and stored at 4° C.

B64. Preparation of a Human Insulin, Lispro Insulin, Aspart Insulin or Glulisine Insulin Solution at 300, 400 and 500 IU/mL Concentrated formulations of human insulin, lispro insulin, aspart insulin or glulisine insulin at 300 IU/mL, 400 IU/mL or 500 IU/mL (and also at all intermediate concentrations) are prepared on the basis of the protocol of example B62 relating to the preparation of a 200 IU/mL glulisine insulin solution. The commercial insulin formulation is concentrated using Amicon Ultra-15 centrifugation tubes with a 3 kDa cut-off threshold. The Amicon tubes are first rinsed with 12 mL of deionized water. 12 mL of the commercial formulation are centrifuged at 4000 g at 20° C. By modifying the centrifugation time, it is possible to adjust the final concentration of insulin in the formulation. The volume of the retentate is measured and the concentration is thus estimated. All the retentates are pooled and the overall concentration is estimated (>300, 400 or 500 IU/mL).

The concentration of this concentrated insulin solution is adjusted to the desired concentration (e.g. 300 IU/mL, 400 IU/mL or 500 IU/mL) by addition of the insulin formulation (Humulin® R, Novolog®, Humalog® or Apidra®). The concentrated insulin formulation has the same concentrations of excipients as the commercial formulation at 100 IU/mL.

The final pH is adjusted to 7.4±0.4. The clear solution is filtered through a 0.22 μm membrane and stored at 4° C.

B65. Preparation of a 200 IU/mL Glulisine Insulin Solution in the Presence of Compound 1 and Citrate For a final volume of 100 mL of formulation, with a [compound 1]/[glulisine insulin] mass ratio of 2, the various reagents are mixed in the amounts specified below and in the following order:

| Lyophilizate of compound 1 | 1460 mg |
| 200 IU/mL glulisine insulin | 100 mL |
| 1.188M sodium citrate solution | 1566 μL |

The final pH is adjusted to 7.4±0.4. The clear solution is filtered through a 0.22 μm membrane and stored at 4° C.

B66. Preparation of a 300 IU/mL Aspart Insulin Solution in the Presence of Compound 1 and Citrate For a final volume of 100 mL of formulation, with a [compound 1]/[aspart insulin] mass ratio of 2.0, the various reagents are mixed in the amounts specified below:

| 300 IU/mL aspart insulin | 100 mL |
| Lyophilizate of compound 1 | 2190 mg |
| Sodium citrate | 720 mg |

The final pH is adjusted to 7.4±0.4. The clear solution is filtered through a 0.22 μm membrane and stored at 4° C.

B67. Preparation of a 300 IU/mL Glulisine Insulin Solution in the Presence of Compound 1 and Citrate For a final volume of 100 mL of formulation, with a [compound 1]/[glulisine insulin] mass ratio of 2.0, the various reagents are mixed in the amounts specified below:

| 300 IU/mL glulisine insulin | 100 mL |
| Lyophilizate of compound 1 | 2190 mg |
| Sodium citrate | 720 mg |

The final pH is adjusted to 7.4±0.4. The clear solution is filtered through a 0.22 μm membrane and stored at 4° C.

B68. Preparation of a 400 IU/mL Aspart Insulin Solution in the Presence of Compound 1 and Citrate For a final volume of 100 mL of formulation, with a [compound 1]/[aspart insulin] mass ratio of 2, the various reagents are mixed in the amounts specified below:

| 400 IU/mL aspart insulin | 100 mL |
| Lyophilizate of compound 1 | 2920 mg |
| Sodium citrate | 960 mg |

The final pH is adjusted to 7.4±0.4. The clear solution is filtered through a 0.22 μm membrane and stored at 4° C.

B69. Preparation of a 400 IU/mL Glulisine Insulin Solution in the Presence of Compound 1 and Citrate For a final volume of 100 mL of formulation, with a [compound 1]/[glulisine insulin] mass ratio of 2.0, the various reagents are mixed in the amounts specified below:

| 400 IU/mL glulisine insulin | 100 mL |
| Lyophilizate of compound 1 | 2920 mg |
| Sodium citrate | 960 mg |

The final pH is adjusted to 7.4±0.4. The clear solution is filtered through a 0.22 μm membrane and stored at 4° C.

B70. Preparation of a 500 IU/mL Aspart Insulin Solution in the Presence of Compound 1 and Citrate For a final volume of 100 mL of formulation, with a [compound 1]/[aspart insulin] mass ratio of 2.0, the various reagents are mixed in the amounts specified below:

| 500 IU/mL aspart insulin | 100 mL |
| Lyophilizate of compound 1 | 3650 mg |
| Sodium citrate | 1200 mg |

The final pH is adjusted to 7.4±0.4. The clear solution is filtered through a 0.22 μm membrane and stored at 4° C.

B71. Preparation of a 500 IU/mL Glulisine Insulin Solution in the Presence of Compound 1 and Citrate For a final volume of 100 mL of formulation, with a [compound 1]/[glulisine insulin] mass ratio of 2.0, the various reagents are mixed in the amounts specified below:

| 500 IU/mL glulisine insulin | 100 mL |
| Lyophilizate of compound 1 | 3650 mg |
| Sodium citrate | 1200 mg |

The final pH is adjusted to 7.4±0.4. The clear solution is filtered through a 0.22 μm membrane and stored at 4° C.

B72. Preparation of a 300 IU/mL Human Insulin Solution in the Presence of Compound 1 and Citrate For a final volume of 100 mL of formulation, with a [compound 1]/[human insulin] mass ratio of 2.0, the various reagents are mixed in the amounts specified below:

| 300 IU/mL human insulin | 100 mL |
| Lyophilizate of compound 1 | 2190 mg |
| Sodium citrate | 720 mg |

The final pH is adjusted to 7.4±0.4. The clear solution is filtered through a 0.22 μm membrane and stored at 4° C.

B73. Preparation of a 300 IU/mL Lispro Insulin Solution in the Presence of Compound 1 and Citrate For a final volume of 100 mL of formulation, with a [compound 1]/[lispro insulin] mass ratio of 2.0, the various reagents are mixed in the amounts specified below:

| 300 IU/mL lispro insulin | 100 mL |
| Lyophilizate of compound 1 | 2190 mg |
| Sodium citrate | 720 mg |

The final pH is adjusted to 7.4±0.4. The clear solution is filtered through a 0.22 µm membrane and stored at 4° C.

B74. Preparation of a 400 IU/mL Human Insulin Solution in the Presence of Compound 1 and Citrate For a final volume of 100 mL of formulation, with a [compound 1]/[human insulin] mass ratio of 2.0, the various reagents are mixed in the amounts specified below:

| 400 IU/mL human insulin | 100 mL |
| Lyophilizate of compound 1 | 2920 mg |
| Sodium citrate | 960 mg |

The final pH is adjusted to 7.4±0.4. The clear solution is filtered through a 0.22 µm membrane and stored at 4° C.

B75. Preparation of a 400 IU/mL Lispro Insulin Solution in the Presence of Compound 1 and Citrate For a final volume of 100 mL of formulation, with a [compound 1]/[lispro insulin] mass ratio of 2.0, the various reagents are mixed in the amounts specified below:

| 400 IU/mL lispro insulin | 100 mL |
| Lyophilizate of compound 1 | 2920 mg |
| Sodium citrate | 960 mg |

The final pH is adjusted to 7.4±0.4. The clear solution is filtered through a 0.22 µm membrane and stored at 4° C.

B76. Preparation of a 500 IU/mL Human Insulin Solution in the Presence of Compound 1 and Citrate For a final volume of 100 mL of formulation, with a [compound 1]/[human insulin] mass ratio of 2.0, the various reagents are mixed in the amounts specified below:

| 500 IU/mL human insulin | 100 mL |
| Lyophilizate of compound 1 | 3650 mg |
| Sodium citrate | 1200 mg |

The final pH is adjusted to 7.4±0.4. The clear solution is filtered through a 0.22 µm membrane and stored at 4° C.

B77. Preparation of a 500 IU/mL Lispro Insulin Solution in the Presence of Compound 1 and Citrate For a final volume of 100 mL of formulation, with a [compound 1]/[lispro insulin] mass ratio of 2.0, the various reagents are mixed in the amounts specified below:

| 500 IU/mL lispro insulin | 100 mL |
| Lyophilizate of compound 1 | 3650 mg |
| Sodium citrate | 1200 mg |

The final pH is adjusted to 7.4±0.4. The clear solution is filtered through a 0.22 µm membrane and stored at 4° C.

B78. Preparation of a 200 IU/mL Lispro Insulin Solution in the Presence of Compound 2 and Citrate For a final volume of 100 mL of formulation, with a [compound 2]/[lispro insulin] mass ratio of 2.0, the various reagents are mixed in the amounts specified below:

| 200 IU/mL lispro insulin | 100 mL |
| Lyophilizate of compound 2 | 1460 mg |
| 1.188M sodium citrate solution | 1566 µL |

The final pH is adjusted to 7.4±0.4. The clear solution is filtered through a 0.22 µm membrane and stored at 4° C.

B79. Preparation of a 200 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| 200 IU/mL aspart insulin | 100 mL |
| Lyophilizate of compound 2 | 1460 mg |
| 1.188M sodium citrate solution | 1566 µL |

The final pH is adjusted to 7.4±0.4. The clear solution is filtered through a 0.22 µm membrane and stored at 4° C.

B80. Preparation of a 200 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| 200 IU/mL glulisine insulin | 100 mL |
| Lyophilizate of compound 2 | 1460 mg |
| 1.188M sodium citrate solution | 1566 µL |

The final pH is adjusted to 7.4±0.4. The clear solution is filtered through a 0.22 µm membrane and stored at 4° C.

B81. Preparation of a 300 IU/mL aspart insulin solution in the presence of Compound 2 and Citrate For a final volume of 100 mL of formulation, with a [compound 2]/[aspart insulin] mass ratio of 2.0, the various reagents are mixed in the amounts specified below:

| 300 IU/mL aspart insulin | 100 mL |
| Lyophilizate of compound 2 | 2190 mg |
| Sodium citrate | 720 mg |

The final pH is adjusted to 7.4±0.4. The clear solution is filtered through a 0.22 µm membrane and stored at 4° C.

B82. Preparation of a 300 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| 300 IU/mL glulisine insulin | 100 mL |
| Lyophilizate of compound 2 | 2190 mg |
| Sodium citrate | 720 mg |

The final pH is adjusted to 7.4±0.4. The clear solution is filtered through a 0.22 µm membrane and stored at 4° C.

B83. Preparation of a 400 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| 400 IU/mL aspart insulin | 100 mL |
| Lyophilizate of compound 2 | 2920 mg |
| Sodium citrate | 960 mg |

The final pH is adjusted to 7.4±0.4. The clear solution is filtered through a 0.22 μm membrane and stored at 4° C.

B84. Preparation of a 400 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| 400 IU/mL glulisine insulin | 100 mL |
| Lyophilizate of compound 2 | 2920 mg |
| Sodium citrate | 960 mg |

The final pH is adjusted to 7.4-0.4. The clear solution is filtered through a 0.22 μm membrane and stored at 4° C.

B85. Preparation of a 500 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| 500 IU/mL aspart insulin | 100 mL |
| Lyophilizate of compound 2 | 3650 mg |
| Sodium citrate | 1200 mg |

The final pH is adjusted to 7.4±0.4. The clear solution is filtered through a 0.22 μm membrane and stored at 4° C.

B86. Preparation of a 500 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| 500 IU/mL glulisine insulin | 100 mL |
| Lyophilizate of compound 2 | 3650 mg |
| Sodium citrate | 1200 mg |

The final pH is adjusted to 7.4±0.4. The clear solution is filtered through a 0.22 μm membrane and stored at 4° C.

B87. Preparation of a 300 IU/mL Human Insulin Solution in the Presence of Compound 2 and Citrate For a final volume of 100 mL of formulation, with a [compound 2]/[human insulin] mass ratio of 2, the various reagents are mixed in the amounts specified below:

| 300 IU/mL human insulin | 100 mL |
| Lyophilizate of compound 2 | 2190 mg |
| Sodium citrate | 720 mg |

The final pH is adjusted to 7.4±0.4. The clear solution is filtered through a 0.22 μm membrane and stored at 4° C.

B88. Preparation of a 300 IU/mL Lispro Insulin Solution in the Presence of Compound 2 and Citrate For a final volume of 100 mL of formulation, with a [compound 2]/[lispro insulin] mass ratio of 2.0, the various reagents are mixed in the amounts specified below:

| 300 IU/mL lispro insulin | 100 mL |
| Lyophilizate of compound 2 | 2190 mg |
| Sodium citrate | 720 mg |

The final pH is adjusted to 7.4±0.4. The clear solution is filtered through a 0.22 μm membrane and stored at 4° C.

B89. Preparation of a 400 IU/mL Human Insulin Solution in the Presence of Compound 2 and Citrate For a final volume of 100 mL of formulation, with a [compound 2]/[human insulin] mass ratio of 2.0, the various reagents are mixed in the amounts specified below:

| 400 IU/mL human insulin | 100 mL |
| Lyophilizate of compound 2 | 2920 mg |
| Sodium citrate | 960 mg |

The final pH is adjusted to 7.4±0.4. The clear solution is filtered through a 0.22 μm membrane and stored at 4° C.

B90. Preparation of a 400 IU/mL Lispro Insulin Solution in the Presence of Compound 2 and Citrate For a final volume of 100 mL of formulation, with a [compound 2]/[lispro insulin] mass ratio of 2.0, the various reagents are mixed in the amounts specified below:

| 400 IU/mL lispro insulin | 100 mL |
| Lyophilizate of compound 2 | 2920 mg |
| Sodium citrate | 960 mg |

The final pH is adjusted to 7.4-0.4. The clear solution is filtered through a 0.22 μm membrane and stored at 4° C.

B91. Preparation of a 500 IU/mL Human Insulin Solution in the Presence of Compound 2 and Citrate For a final volume of 100 mL of formulation, with a [compound 2]/[human insulin] mass ratio of 2.0, the various reagents are mixed in the amounts specified below:

| 500 IU/mL human insulin | 100 mL |
| Lyophilizate of compound 2 | 3650 mg |
| Sodium citrate | 1200 mg |

The final pH is adjusted to 7.4-0.4. The clear solution is filtered through a 0.22 μm membrane and stored at 4° C.

B92. Preparation of a 500 IU/mL Lispro Insulin Solution in the Presence of Compound 2 and Citrate For a final volume of 100 mL of formulation, with a [compound 2]/[lispro insulin] mass ratio of 2.0, the various reagents are added in the amounts specified below:

| 500 IU/mL lispro insulin | 100 mL |
| Lyophilizate of compound 2 | 3650 mg |
| Sodium citrate | 1200 mg |

The final pH is adjusted to 7.4±0.4. The clear solution is filtered through a 0.22 μm membrane and stored at 4° C.

B93. Preparation of a 100 IU/mL Lispro Insulin Solution in the Presence of Compound 3 and Citrate For a final volume of 100 mL of formulation, with a [compound 3]/[lispro insulin] mass ratio of 2.0 and a citrate concentration of 9.3 mM, the various reagents are added in the amounts specified below and in the following order:

| | |
|---|---|
| Lyophilized compound 3 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B94. Preparation of a 100 IU/mL Lispro Insulin Solution in the Presence of Compound 4 and Citrate For a final volume of 100 mL of formulation, with a [compound 4]/[lispro insulin] mass ratio of 2.0 and a citrate concentration of 9.3 mM, the various reagents are added in the amounts specified below and in the following order:

| | |
|---|---|
| Lyophilized compound 4 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B95. Preparation of a 100 IU/mL Human Insulin Solution in the Presence of Compound 3 and Citrate For a final volume of 100 mL of formulation, with a [compound 3]/[human insulin] mass ratio of 2.0 and a citrate concentration of 9.3 mM, the various reagents are added in the amounts specified below and in the following order:

| | |
|---|---|
| Lyophilized compound 3 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B96. Preparation of a 100 IU/mL Human Insulin Solution in the Presence of Compound 4 and Citrate For a final volume of 100 mL of formulation, with a [compound 4]/[human insulin] mass ratio of 2.0 and a citrate concentration of 9.3 mM, the various reagents are added in the amounts specified below and in the following order:

| | |
|---|---|
| Lyophilized compound 4 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

C Pharmacodynamics and Pharmacokinetics

C1: Protocol for Measuring the Pharmacodynamics of the Insulin Solutions

Twelve domestic pigs weighing about 50 kg, catheterized beforehand in the jugular vein, are fasted for 2.5 hours before the start of the experiment. In the hour preceding the injection of insulin, three blood samples are taken in order to determine the basal level of glucose and of insulin.

The injection of insulin at a dose of 0.09 IU/kg for lispro insulin and at a dose of 0.125 IU/kg for human insulin and aspart insulin is performed subcutaneously into the neck, under the animal's ear, using a Novopen insulin pen equipped with a 31 G needle.

Blood samples are then taken every 4 minutes for 20 minutes and then every 10 minutes up to 3 hours. After taking each sample, the catheter is rinsed with a dilute heparin solution.

A drop of blood is taken to determine the glycemia using a glucometer.

The glucose pharmacodynamic curves are then plotted and the time required to reach the minimum glucose level in the blood for each pig is determined and reported as the glucose Tmin. The mean of the glucose Tmin values is then calculated.

The remaining blood is collected in a dry tube and is centrifuged to isolate the serum. The insulin levels in the serum samples are measured via the sandwich ELISA immunoenzymatic method for each pig.

The pharmacokinetic curves are then plotted. The time required to reach the maximum insulin concentration in the serum for each pig is determined and reported as the insulin Tmax. The mean of the insulin Tmax values is then calculated.

C2: Pharmacodynamic and Pharmacokinetic Results for the Insulin Solutions of Examples B2 and B8

| Example | Insulin | Compound | Polyanionic compound | Number of pigs |
|---|---|---|---|---|
| B2 | Lispro | — | — | 11 |
| B8 | Lispro | 1 | Citrate 9.3 mM | 10 |

The pharmacodynamic results obtained with the formulations described in examples B2 and B8 are presented in FIG. 1. According to the invention, the analysis of these curves shows that the formulation of example B8 comprising compound 1 and citrate at 9.3 mM as excipient (curve plotted with the squares corresponding to example B8, glucose Tmin=35±11 min) makes it possible to obtain more rapid action than that obtained with the Humalog® commercial formulation of example B2 (curve plotted with the triangles corresponding to example B2, glucose Tmin=44±14 min).

The pharmacokinetic results obtained with the formulations described in examples B2 and B8 are presented in FIG. 2. According to the invention, the analysis of these curves shows that the formulation of example B8 comprising compound 1 and citrate at 9.3 mM as excipients (curve plotted with the squares corresponding to example B8, insulin Tmax=11±6 min) induces more rapid absorption of the lispro insulin than that of the Humalog® commercial formulation of example B2 (curve plotted with the triangles corresponding to example B2, insulin Tmax=18±8 min).

C3: Pharmacodynamic and Pharmacokinetic Results for the Insulin Solutions of Examples B2 and B10

| Example | Insulin | Compound | Polyanionic compound | Number of pigs |
|---|---|---|---|---|
| B2 | Lispro | — | — | 11 |
| B10 | Lispro | 1 | Polyanionic compound 1 | 11 |

The pharmacodynamic results obtained with the formulations described in examples B2 and B10 are presented in FIG. 3. According to the invention, the analysis of these curves shows that the formulation of example B10 comprising compound 1 and the polyanionic compound 1 as excipients at 20 mg/mL (curve plotted with the squares corresponding to example B10, glucose Tmin=33±13 min) makes it possible to obtain more rapid action than that obtained with the Humalog® commercial formulation of example B2 (curve plotted with the triangles corresponding to example B2, glucose Tmin=44±14 min).

The pharmacokinetic results obtained with the formulations described in examples B2 and B10 are presented in FIG. 4. According to the invention, the analysis of these curves shows that the formulation of example B10 comprising compound 1 and the polyanionic compound 1 as excipients at 20 mg/mL (curve plotted with the squares corresponding to example B10, insulin Tmax=15±9 min) induces more rapid absorption of the lispro insulin than that of the Humalog® commercial formulation of example B2 (curve plotted with the triangles corresponding to example B2, insulin Tmax=18±8 min).

C4: Pharmacodynamic and Pharmacokinetic Results for the Insulin Solutions of Examples B2 and B7

| Example | Insulin | Compound | Polyanionic compound | Number of pigs |
|---|---|---|---|---|
| B2 | Lispro | — | — | 12 |
| B7 | Lispro | 1 | — | 12 |

The pharmacodynamic results obtained with the formulations described in examples B2 and B7 are presented in FIG. 5. According to the invention, the analysis of these curves shows that the formulation of example B7 comprising compound 1 as excipient (curve plotted with the squares corresponding to example B7, glucose Tmin=41≅16 min) includes more rapid onset of action than that obtained with the Humalog® commercial formulation of example B2 (curve plotted with the triangles corresponding to example B2, glucose Tmin=50±14 min).

The pharmacokinetic results obtained with the formulations described in examples B2 and B7 are presented in FIG. 6. The analysis of these curves shows that the formulation comprising compound 1 as excipient (curve plotted with the squares corresponding to example B2, insulin Tmax=21±10 min) does not induce more rapid absorption of the lispro insulin than that of the Humalog® commercial formulation of example B2 (curve plotted with the triangles corresponding to example B2 (insulin Tmax=20±9 min). Compound 1 alone is therefore insufficient to induce significant acceleration of the pharmacokinetics of lispro insulin.

C5: Pharmacodynamic and Pharmacokinetic Results for the Insulin Solutions of Examples B1 and B3

| Example | Insulin | Compound | Polyanionic compound | Number of pigs |
|---|---|---|---|---|
| B1 | Aspart | — | — | 11 |
| B3 | Human | — | — | 11 |

The pharmacodynamic results obtained with the formulations described in examples 81 and B3 are presented in FIG. 7. The analysis of these curves shows that the human insulin formulation of example B3 (curve plotted with the squares corresponding to example B3, glucose Tmin=61±31 min) does indeed have slower action than that of the aspart insulin commercial formulation of example B1 (curve plotted with the triangles corresponding to example B1, glucose Tmin=44±13 min).

The pharmacokinetic results obtained with the formulations described in examples B1 and B3 are presented in FIG. 8. The analysis of these curves shows that the human insulin formulation alone of example B3 (curve plotted with the squares corresponding to example B3, insulin Tmax=36±33 min) does indeed induce slower absorption than that of the aspart insulin commercial formulation (Novolog®) of example B1 (curve plotted with the triangles corresponding to example B1, insulin Tmax=28±13 min).

These results are in accordance with the literature results, with acceleration of the lowering of glycemia and of the absorption of insulin for a rapid insulin analog relative to a human insulin.

C6: Pharmacodynamic and Pharmacokinetic Results for the Insulin Solutions of Examples B1 and B39

| Example | Insulin | Compound | Polyanionic compound | Number of pigs |
|---|---|---|---|---|
| B1 | Aspart | — | — | 14 |
| B39 | Human | 1 | Citrate 9.3 mM | 5 |

The pharmacodynamic results obtained with the formulations described in examples B1 and B39 are presented in FIG. 9. The analysis of these curves shows that the formulation based on human insulin of example B39 comprising compound 1 and citrate at 9.3 mM as excipients (curve plotted with the squares corresponding to example B39, glucose Tmin=46±9 min) makes it possible to obtain similar action to that obtained with the aspart insulin commercial formulation (Novolog®) of example B1 (curve plotted with the triangles corresponding to example B1, glucose Tmin=53±24 min).

The pharmacokinetic results obtained with the formulations described in examples B1 and B39 are presented in FIG. 10. The analysis of these curves shows that the formulation of example B39 comprising compound 1 and citrate at 9.3 mM as excipients (curve plotted with the squares corresponding to example B39, insulin Tmax=20±7 min) induces insulin absorption similar to that obtained with the aspart insulin commercial formulation (Novolog®) of example B1 (curve plotted with the triangles corresponding to example B1, insulin Tmax=22±10 min).

Since the time parameters for the aspart insulin (Novolog®) between examples C5 and C6 are similar, it may be deduced by extrapolation that the formulation of example B39 induces acceleration of the lowering of glycemia and of the absorption of human insulin relative to the commercial formulation of human insulin (example B3).

C7: Pharmacodynamic and Pharmacokinetic Results for the Insulin Solutions of Examples B2 and B11

| Example | Insulin | Compound | Polyanionic compound | Number of pigs |
|---|---|---|---|---|
| B2 | Lispro | — | — | 26 |
| B11 | Lispro | 2 | Citrate 9.3 mM | 23 |

The pharmacodynamic results obtained with the formulations described in examples B2 and B11 are presented in FIG. 13. According to the invention, the analysis of these curves shows that the formulation of example B11 comprising compound 2 and citrate at 9.3 mM as excipients (curve plotted with the squares corresponding to example B11, glucose Tmin=32±10 min) makes it possible to obtain more rapid action than that obtained with the Humalog® commercial formulation of example B2 (curve plotted with the triangles corresponding to example B2, glucose Tmin=41±21 min).

The pharmacokinetic results obtained with the formulations described in examples B2 and B11 are presented in FIG. 14. According to the invention, the analysis of these curves shows that the formulation of example B11 comprising compound 2 and citrate at 9.3 mM as excipients (curve plotted with the squares corresponding to example B11, insulin Tmax=13±5 min) induces more rapid absorption of the lispro insulin than that of the Humalog® commercial formulation of example B2 (curve plotted with the triangles corresponding to example B2, insulin Tmax=22±13 min).

C8: Pharmacodynamic and Pharmacokinetic Results for the Insulin Solutions of Examples B1 and B38

| Example | Insulin | Compound | Polyanionic compound | Number of pigs |
|---|---|---|---|---|
| B1 | Aspart | — | — | 37 |
| B38 | Human | 2 | Citrate 9.3 mM | 31 |

The pharmacodynamic results obtained with the formulations described in examples B1 and B38 are presented in FIG. 15. The analysis of these curves shows that the formulation based on human insulin of example B38 comprising compound 2 and citrate at 9.3 mM as excipients (curve plotted with the squares corresponding to example B102, glucose Tmin=47±30 min) makes it possible to obtain similar action to that obtained with the aspart insulin commercial formulation (Novolog®) of example B1 (curve plotted with the triangles corresponding to example B1, glucose Tmin=47±15 min).

The pharmacokinetic results obtained with the formulations described in examples B1 and B38 are presented in FIG. 16. The analysis of these curves shows that the formulation of example B38 comprising compound 2 and citrate at 9.3 mM as excipients (curve plotted with the squares corresponding to example B38, insulin Tmax=22±21 min) induces human insulin absorption similar to that obtained with the aspart insulin commercial formulation (Novolog®) of example B1 (curve plotted with the triangles corresponding to example B1, insulin Tmax=19±12 min).

Since the time parameters for the aspart insulin (Novolog®) between examples C5 and C8 are similar, it may be deduced by extrapolation that the formulation of example B38 induces acceleration of the lowering of glycemia and of the absorption of human insulin relative to the commercial formulation of human insulin (example B3).

C9: Pharmacodynamic and Pharmacokinetic Results for the Insulin Solutions of Examples B1 and B53

| Example | Insulin | Compound | Polyanionic compound | Number of pigs |
|---|---|---|---|---|
| B1 | Aspart | — | — | 12 |
| B53 | Human | Compound 8 | Citrate 9.3 mM | 8 |

The pharmacodynamic results obtained with the formulations described in examples B1 and B53 are presented in FIG. 17. The analysis of these curves shows that the formulation based on human insulin of example B53 comprising compound 8 and citrate at 9.3 mM as excipients (curve plotted with the squares corresponding to example B53, glucose Tmin=63±36 min) makes it possible to obtain action virtually as rapid as that obtained with the aspart insulin commercial formulation (Novolog®) of example B1 (curve plotted with the triangles corresponding to example B1, glucose Tmin=53±19 min).

The pharmacokinetic results obtained with the formulations described in examples B1 and B53 are presented in FIG. 18. The analysis of these curves shows that the formulation of example B53 comprising compound 8 and citrate at 9.3 mM as excipients (curve plotted with the squares corresponding to example B53, insulin Tmax=19±12 min) induces human insulin absorption similar to that obtained with the aspart insulin commercial formulation (Novolog®) of example B1 (curve plotted with the triangles corresponding to example B1, insulin Tmax=19±6 min).

Since the time parameters for the aspart insulin (Novolog®) between examples C5 and C9 are similar, it may be deduced by extrapolation that the formulation of example B53 induces acceleration of the lowering of glycemia and of the absorption of human insulin relative to the commercial formulation of human insulin (example B3).

D Circular Dichroism

D1: Association State of Lispro Insulin Evaluated by Circular Dichroism in the Presence of Compound 1

Circular dichroism makes it possible to study the secondary and quaternary structure of insulin. The insulin monomers are organized as dimers and as hexamers. The hexamer is the physically and chemically most stable form of insulin. Two hexameric forms exist, the R6 form and the T6 form. Lispro insulin has a strong CD signal at 251 nm characteristic of the R6 hexameric form (most stable form). Loss of the CD signal at 251 nm is linked to destabilization of the hexamer (and thus the first sign of transformation of the hexamer into dimer).

EDTA and the EDTA/citrate mixture completely destructure the R6 form of lispro insulin (FIG. 11). EDTA thus has a pronounced effect on the hexamer.

In contrast, citrate alone, compound 1 alone, and also the mixture compound 1/citrate and compound 1/polyanionic compound 1, have virtually no impact on the CD signal at 251 nm. These compounds therefore have virtually no impact on the R6 structure of the hexamer and, all the less so, on the hexameric structure.

D2: Association State of Human Insulin Evaluated by Circular Dichroism in the Presence of Compound 1

Circular dichroism makes it possible to study the secondary and quaternary structure of insulin. The insulin monomers are organized as dimers and as hexamers. The hexamer is the physically and chemically most stable form of insulin. The CD signal at 275 nm is characteristic of the hexameric form of insulin (hexamer signal at about −3000, signal for the dimer between −200° and −250°, and signal for the monomer below −200°). Loss of the CD signal at 275 nm is therefore characteristic of destabilization of the hexamer into dimers or monomers.

EDTA and the EDTA/citrate combination have a very pronounced impact on the hexameric structure of human insulin (total dissociation of the hexamer into dimers, FIG. 12). In contrast, citrate alone, compound 1 alone, the polyanionic compound 1 alone and also the compound 1/citrate and compound 1/polyanionic compound 1 combinations have no impact on the hexameric structure of human insulin. Unlike EDTA, the human insulin formulations comprising compound 1 and citrate or the polyanionic compound 1 do not show any dissociation of the human insulin hexamer.

D3: Association State of Lispro Insulin Evaluated by Circular Dichroism in the Presence of Compounds 1 to 11

Circular dichroism makes it possible to study the secondary and quaternary structure of insulin. The insulin monomers are organized as dimers and as hexamers. The hexamer is the physically and chemically most stable form of insulin. Two hexameric forms exist, the R6 form and the T6 form. Lispro insulin has a strong CD signal at 251 nm characteristic of the R6 hexameric form (most stable form). Loss of the CD signal at 251 nm is linked to destabilization of the hexamer (and thus the first sign of transformation of the hexamer into dimer). The results obtained are presented in FIG. 19. This figure describes on the x-axis:

A: lispro insulin (100 IU/mL)
B: lispro insulin+7.3 mg/mL of compound 2
C: lispro insulin+7.3 mg/mL of compound 2+citrate at 9.3 mM
D: lispro insulin+7.3 mg/mL of compound 1
E: lispro insulin+7.3 mg/mL of compound 1+citrate at 9.3 mM
F: lispro insulin+7.3 mg/mL of compound 3
G: lispro insulin+7.3 mg/mL of compound 3+citrate at 9.3 mM
H: lispro insulin+7.3 mg/mL of compound 4
I: lispro insulin+7.3 mg/mL of compound 4+citrate at 9.3 mM
J: lispro insulin+7.3 mg/mL of compound 5
K: lispro insulin+7.3 mg/mL of compound 5+citrate at 9.3 mM
L: lispro insulin+7.3 mg/mL of compound 6
M: lispro insulin+7.3 mg/mL of compound 6+citrate at 9.3 mM
N: lispro insulin+7.3 mg/mL of compound 7
O: lispro insulin+7.3 mg/mL of compound 7+citrate at 9.3 mM
P: lispro insulin+7.3 mg/mL of compound 8
Q: lispro insulin+7.3 mg/mL of compound 8+citrate at 9.3 mM
R: lispro insulin+7.3 mg/mL of compound 9
S: lispro insulin+7.3 mg/mL of compound 9+citrate at 9.3 mM
T: lispro insulin+7.3 mg/mL of compound 10
U: lispro insulin+7.3 mg/mL of compound 10+citrate at 9.3 mM
V: lispro insulin+7.3 mg/mL of compound 11
W: lispro insulin+7.3 mg/mL of compound 11+citrate at 9.3 mM and on the y-axis the circular dichroism signal at 251 nm (deg·cm$^2$·dmol$^{-1}$).

Compounds 1 to 11 alone and also compounds 1 to 11 in combination with citrate have no impact on the CD signal at 251 nm for lispro insulin. Compounds 1 to 11 therefore have no impact on the R6 structure of the hexamer and, all the less so, on the hexameric structure of lispro insulin.

D4: Association State of Human Insulin Evaluated by Circular Dichroism in the Presence of Compounds 1 to 11

Circular dichroism makes it possible to study the secondary and quaternary structure of insulin. The insulin monomers are organized as dimers and as hexamers. The hexamer is the physically and chemically most stable form of insulin. The CD signal at 275 nm is characteristic of the hexameric form of insulin (hexamer signal at about −300° C., signal for the dimer between −200° and −250°, and signal for the monomer below −200°). Loss of the CD signal at 275 nm is therefore characteristic of destabilization of the hexamer into dimers or monomers. The results obtained are presented in FIG. 20. This figure describes on the x-axis:

A: human insulin (100 IU/mL)
B: human insulin+7.3 mg/mL of compound 2
C: human insulin+7.3 mg/mL of compound 2+citrate at 9.3 mM
D: human insulin+7.3 mg/mL of compound 1
E: human insulin+7.3 mg/mL of compound 1+citrate at 9.3 mM
F: human insulin+7.3 mg/mL of compound 3
G: human insulin+7.3 mg/mL of compound 3+citrate at 9.3 mM
H: human insulin+7.3 mg/mL of compound 4
I: human insulin+7.3 mg/mL of compound 4+citrate at 9.3 mM
J: human insulin+7.3 mg/mL of compound 5
K: human insulin+7.3 mg/mL of compound 5+citrate at 9.3 mM
L: human insulin+7.3 mg/mL of compound 6
M: human insulin+7.3 mg/mL of compound 6+citrate at 9.3 mM
N: human insulin+7.3 mg/mL of compound 7
O: human insulin+7.3 mg/mL of compound 7+citrate at 9.3 mM
P: human insulin+7.3 mg/mL of compound 8
Q: human insulin+7.3 mg/mL of compound 8+citrate at 9.3 mM
R: human insulin+7.3 mg/mL of compound 9
S: human insulin+7.3 mg/mL of compound 9+citrate at 9.3 mM
T: human insulin+7.3 mg/mL of compound 10
U: human insulin+7.3 mg/mL of compound 10+citrate at 9.3 mM
V: human insulin+7.3 mg/mL of compound 11
W: human insulin+7.3 mg/mL of compound 11+citrate at 9.3 mM and on the y-axis the circular dichroism signal at 275 nm (deg·cm$^2$·dmol$^{-1}$).

Compounds 1 to 11 alone and also compounds 1 to 11 in combination with citrate have no impact on the CD signal at 275 nm for human insulin. Compounds 1 to 11 therefore have no impact on the hexameric structure of human insulin.

E Dissolution of Human Insulin and Insulin Analogs at the Isoelectric Point

E1. Dissolution of Human Insulin at its Isoelectric Point

Human insulin has an isoelectric point at 5.3. At this pH of 5.3, human insulin precipitates. A test demonstrating the formation of a complex of human insulin with the various compounds is performed at the isoelectric point. If an interaction exists, it is possible to dissolve the insulin at its isoelectric point.

A 200 IU/mL human insulin solution is prepared. Solutions of compounds at different concentrations (8, 30 or 100 mg/mL) in water are prepared. An equivolume (50/50) mixture between the human insulin solution and the solution of compound is prepared to lead to a solution containing 100 IU/mL of human insulin and the desired concentration of compound (4, 15 or 50 mg/mL). The pH of the various solutions is adjusted to pH 5.3 by adding 200 mM acetic acid.

The appearance of the solution is documented. If the solution is turbid, the compound at the test concentration does not allow dissolution of the human insulin. If the solution is translucent, the compound allows dissolution of the human insulin at the test concentration. In this way, the concentration of compound required to dissolve the human insulin at its isoelectric point may be determined. The lower this concentration, the greater the affinity of the compound for human insulin.

The results obtained are presented in Table 3. The results show that the compounds and the polysaccharides do not have the same properties in terms of human insulin dissolution.

TABLE 3

| Compounds (examples) or Polysaccharides (counterexamples) | Dissolution of human insulin at 100 IU/mL with the compound at 4 mg/mL | Dissolution of human insulin at 100 IU/mL with the compound at 15 mg/mL | Dissolution of human insulin at 100 IU/mL with the compound at 50 mg/mL |
|---|---|---|---|
| Counterexamples | | | |
| Polysaccharide 1 | Yes | Yes | Yes |
| Polysaccharide 4 | Yes | Yes | Yes |
| Polysaccharide 3 | Yes | Yes | Yes |
| Polysaccharide 2 | Yes | Yes | Yes |
| Polysaccharide 5 | Yes | Yes | Yes |
| Examples | | | |
| Compound 1 | No | No | Yes |
| Compound 2 | No | No | Yes |
| Compound 3 | No | No | Yes |
| Compound 4 | No | No | Yes |
| Compound 6 | No | No | Yes |
| Compound 8 | No | No | Yes |
| Compound 9 | No | No | Yes |
| Compound 10 | No | No | Yes |

E2. Dissolution of Lispro Insulin at its Isoelectric Point

Lispro insulin has an isoelectric point at 5.3. At this pH, lispro insulin precipitates. A test demonstrating the formation of a complex of lispro insulin with the various compounds is performed at the isoelectric point. If an interaction exists, it is possible to dissolve the lispro insulin at its isoelectric point.

The commercial formulation of lispro insulin (Humalog®) is dialyzed against 1 mM $PO_4$ buffer (pH 7). After dialysis, the lispro insulin concentration is about 90 IU/mL. The lyophilized compound is weighed out and dissolved in the lispro insulin solution to lead to formulations containing lispro insulin at 90 IU/mL and the compound at the desired concentrations (4, 15 or 50 mg/mL). The pH of the various solutions is adjusted to pH 5.3 by adding 200 mM acetic acid.

The appearance of the solution is documented. If the solution is turbid, the compound at the test concentration does not allow dissolution of the lispro insulin. If the solution is translucent, the compound allows dissolution of the lispro insulin at the test concentration. In this way, the concentration of compound required to dissolve the lispro insulin at its isoelectric point may be determined. The lower this concentration, the greater the affinity of the compound for the lispro insulin.

The results obtained are presented in Table 4. The results show that the compounds and the polysaccharides do not have the same properties in terms of lispro insulin dissolution.

TABLE 4

| Compounds (examples) or Polysaccharides (counterexamples) | Dissolution of lispro insulin at 90 IU/mL with the compound at 4 mg/mL | Dissolution of lispro insulin at 90 IU/mL with the compound at 15 mg/mL | Dissolution of lispro insulin at 90 IU/mL with the compound at 50 mg/mL |
|---|---|---|---|
| Counterexamples | | | |
| Polysaccharide 1 | Yes | Yes | Yes |
| Polysaccharide 3 | Yes | Yes | Yes |
| Polysaccharide 2 | Yes | Yes | Yes |

TABLE 4-continued

| Compounds (examples) or Polysaccharides (counterexamples) | Dissolution of lispro insulin at 90 IU/mL with the compound at 4 mg/mL | Dissolution of lispro insulin at 90 IU/mL with the compound at 15 mg/mL | Dissolution of lispro insulin at 90 IU/mL with the compound at 50 mg/mL |
|---|---|---|---|
| Examples | | | |
| Compound 1 | No | No | Yes |
| Compound 2 | No | No | Yes |
| Compound 3 | No | No | Yes |

F Interaction with Albumin

F1:

In order to determine the interactions between the various polysaccharides or compounds and a model protein such as albumin, a Centricon test (membrane with a cut-off threshold of 50 kDa) was performed. A solution of polysaccharide or of compound at 7.3 mg/mL was diluted three-fold in a solution of BSA (bovine serum albumin) at 20 mg/mL in PBS (concentration in the mixture: 2.43 mg/mL of polysaccharide or of compound, 13.3 mg/mL of albumin and about 100 mM of salts).

This mixture was centrifuged on a Centricon to make about half the volume pass through the membrane. The albumin is quantitatively retained on the Centricon membrane. The polysaccharides and compounds analyzed alone pass in large majority through the membrane (for the polysaccharides having the largest molar masses, about 20% of the polysaccharide is retained).

After centrifugation, the polysaccharide or compound is assayed by UV in the filtrate. The percentage of polysaccharide or compound bound to the albumin is calculated via the following equation:

(1−[polysaccharide or compound in the filtrate in the presence of albumin]/[polysaccharide or compound in the filtrate in the absence of albumin])*100

The results obtained are presented in Table 5. It is very clearly observed that the polysaccharides of molar mass 5-15 kDa are strongly retained by the albumin in this test. In contrast, the compounds of the invention of lower molar mass are markedly less retained by the albumin in this test.

TABLE 5

| Polysaccharide or Compound | % Polysaccharide or % Compound bound to BSA |
| --- | --- |
| Counterexamples | |
| Polysaccharide 4 | 97% |
| Polysaccharide 1 | 95% |
| Polysaccharide 3 | 77% |
| Polysaccharide 5 | 86% |
| Polysaccharide 2 | 82% |
| Examples | |
| Compound 2 | 21% |
| Compound 1 | 20% |
| Compound 3 | 27% |
| Compound 4 | 24% |
| Compound 5 | 24% |
| Compound 6 | 26% |
| Compound 7 | 27% |
| Compound 8 | 27% |
| Compound 9 | 43% |
| Compound 11 | 35% |

The invention claimed is:

1. A composition comprising insulin in hexameric form, at least one substituted anionic compound and a polyanionic compound, in an aqueous solution:
wherein the insulin in hexameric form is human insulin or an insulin analog;
said substituted anionic compound being chosen from substituted anionic compounds, in isolated form or as a mixture, consisting of a backbone formed from a discrete number u of between 1 and 8 (1≤u≤8) of identical or different saccharide units, linked via identical or different glycoside bonds, wherein u is the same for all of the at least one substituted anionic compounds, said saccharide units being chosen from the group consisting of hexoses, in cyclic form or in open reduced form, wherein they are substituted with:
a) at least one substituent of general formula I:

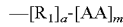   Formula I the substituents being identical or different when there are at least two substituents, in which:
the radical -[AA] denotes an amino acid residue,
the radical —$R_1$— being:
either a bond and then a=0 and the amino acid residue -[AA] is directly linked to the backbone via a function G,
or a C2 to C15 carbon-based chain, and then a=1, optionally substituted and/or comprising at least one heteroatom chosen from O, N and S and at least one acid function before the reaction with the amino acid, said chain forming with the amino acid residue -[AA] an amide function, and is attached to the backbone by means of a function F resulting from a reaction between a hydroxyl function borne by the backbone and a function or substituent borne by the precursor of the radical —$R_1$—,
F is an ether, ester or carbamate function,
G is a carbamate function,
m is equal to 1 or 2,
the degree of substitution of the saccharide units, j, with —$[R_1]_a$-$[AA]_m$ being strictly greater than 0 and less than or equal to 6, 0≤j≤6;
b) and, optionally, one or more substituents —$R'_1$,
the substituent —$R'_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —$R'_1$,
F' is an ether, ester or carbamate function,
the degree of substitution of the saccharide units, i, with —$R'_1$, being between 0 and 6−j, 0≤i≤6−j, and
F, F' and G are identical or different,
i+j≤6,
—$R'_1$ is identical to or different from —$R_1$—,
the free salifiable acid functions borne by the substituent —$R'_1$ are in the form of alkali metal cation salts,
said glycoside bonds, which may be identical or different, being chosen from the group consisting of glycoside bonds of (1,1), (1,2), (1,3), (1,4) or (1,6) type, in an alpha or beta geometry,
and
said polyanionic compound is chosen from the group consisting of citric acid and $Na^+$, $K^+$, $Ca^{2+}$ or $Mg^{2+}$ salts thereof.

2. The composition as claimed in claim 1, wherein the insulin is a human insulin.

3. The composition as claimed in claim 1, wherein the insulin is an insulin analog.

4. The composition as claimed in claim 3, wherein the insulin analog is chosen from the group consisting of the insulin lispro (Humalog®), the insulin aspart (Novolog®, Novorapid®) and the insulin glulisine (Apidra®).

5. The composition as claimed in claim 3, wherein the insulin analog is the insulin lispro (Humalog®).

6. The composition as claimed in claim 1, wherein the substituted anionic compound/insulin mass ratio is between 0.5 and 10.

7. The composition as claimed in claim 1, wherein the concentration of substituted anionic compound is between 1.8 and 36 mg/mL.

8. A pharmaceutical formulation comprising the composition as claimed in claim 1.

9. The pharmaceutical formulation as claimed in claim 8, wherein the insulin concentration is between 240 and 3000 μM (40 to 500 IU/mL).

10. The pharmaceutical formulation as claimed in claim 9, wherein the insulin concentration is between 600 and 1200 μM (100 and 200 IU/mL).

11. An insulin pharmaceutical formulation comprising insulin, at least one substituted anionic compound having a backbone formed from a discrete number u of between 1 and 8 (1≤u≤8) of identical or different saccharide units, linked via identical or different glycoside bonds, wherein u is the same for all of the at least one substituted anionic compounds, said saccharide units being chosen from the group consisting of hexoses, in cyclic form or in open reduced form, said substituted anionic compound comprising partially substituted carboxyl functional groups, the unsubstituted carboxyl functional groups being salifiable, and a polyanionic compound that is chosen from the group consisting of citric acid and Na$^+$, K$^+$, Ca$^{2+}$ or Mg$^{2+}$ salts thereof, wherein the insulin pharmaceutical formulation makes it possible, after administration, to accelerate the passage of the insulin into the blood and to reduce the glycemia more rapidly when compared with a formulation free of substituted anionic compound.

12. The insulin pharmaceutical formulation as claimed in claim 11, wherein the substituted anionic compound is chosen from substituted anionic compounds consisting of a saccharide backbone formed from a discrete number u of between 1 and 8 (1≤u≤8) of identical or different saccharide units, linked via identical or different glycoside bonds, wherein u is the same for all of the at least one substituted anionic compounds, said saccharide units being chosen from hexoses, in cyclic form or in open reduced form, wherein they are substituted with:

a) at least one substituent of general formula I:

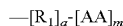      Formula I the substituents being identical or different when there are at least two substituents, in which:
the radical -[AA] denotes an amino acid residue, said amino acid being chosen from the group consisting of phenylalanine, alpha-methylphenylalanine, 3,4-dihydroxyphenylalanine, tyrosine, alpha-methyltyrosine, O-methyltyrosine, alpha-phenylglycine, 4-hydroxyphenylglycine and 3,5-dihydroxyphenylglycine, and the alkali metal cation salts thereof, said derivatives being in L or D absolute configuration, -[AA]- is attached to the backbone of the molecule via a radical —R$_1$— or directly attached to the backbone via a function G, —R$_1$— being:
either a bond G, and then a=0,
or a C2 to C15 carbon-based chain, and then a=1, which is optionally substituted and/or comprising at least one heteroatom chosen from O, N and S and at least one acid function before the reaction with the amino acid, said chain forming with the amino acid residue -[AA] an amide function, and is attached to the backbone by means of a function F resulting from a reaction between a hydroxyl function or a substituent borne by the backbone and a function or a substituent borne by the precursor of the radical —R$_1$—, F is an ether, ester or carbamate function,
G is a carbamate function,
m is equal to 1 or 2,
the degree of substitution, j, with —[R$_1$]$_a$-[AA]$_m$ being strictly greater than 0 and less than or equal to 6, 0<j≤6, b) and, optionally, one or more substituents —R'$_1$;
the substituent —R'$_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —R'$_1$, F' is an ether, ester or carbamate function,
the degree of substitution of the saccharide units, i, with —R'$_1$, being between 0 and 6-j, 0≤i≤6-j, and
—R'$_1$— is identical to or different from —R$_1$,
F, F' and G are identical or different,
the free salifiable acid functions are in the form of alkali metal cation salts,
said glycoside bonds, which may be identical or different, being chosen from the group consisting of glycoside bonds of (1,1), (1,2), (1,3), (1,4) or (1,6) type, in an alpha or beta geometry,
i+j≤6.

13. A composition comprising insulin in hexameric form, at least one substituted anionic compound and a polyanionic compound, in an aqueous solution:
wherein the insulin in hexameric form is human insulin or an insulin analog;
said substituted anionic compound being chosen from substituted anionic compounds, in isolated form or as a mixture, consisting of a backbone formed from a saccharide unit

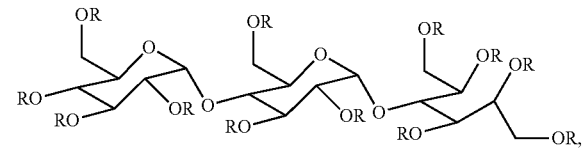

wherein R is selected from the group consisting of H, —[R$_1$]$_a$-[AA]$_m$, and —R'$_1$, wherein substituent —[R$_1$]$_a$-[AA]$_m$ is

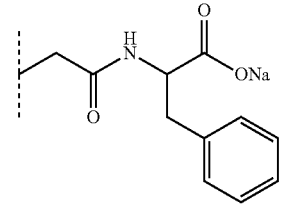

and substituent —R'$_1$ is

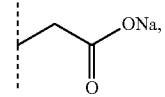

with a degree of substitution of the saccharide unit, j, with —[R$_1$]$_a$-[AA]$_m$ being 0.65 and a degree of substitution of the saccharide unit, i, with —R'$_1$, being 1.0, and
said polyanionic compound is chosen from the group consisting of citric acid and Na$^+$, K$^+$, Ca$^{2+}$ or Mg$^{2+}$ salts thereof.

14. A composition comprising insulin in hexameric form, at least one substituted anionic compound and a polyanionic compound, in an aqueous solution:
wherein the insulin in hexameric form is human insulin or an insulin analog;
said substituted anionic compound being chosen from substituted anionic compounds, in isolated form or as a mixture, consisting of a backbone formed from a saccharide unit

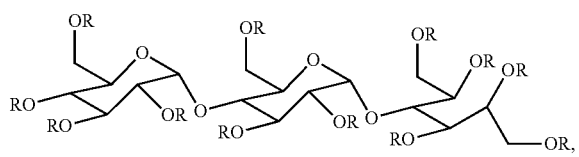

wherein R is selected from the group consisting of H, —[R₁]ₐ-[AA]ₘ, and —R'₁, wherein substituent —[R₁]ₐ-[AA]ₘ is

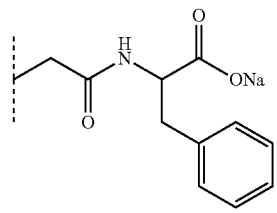

and substituent —R'₁ is

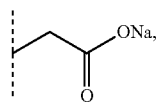

with a degree of substitution of the saccharide unit, j, with —[R₁]ₐ-[AA]ₘ being 0.4 and a degree of substitution of the saccharide unit, i, with —R'₁, being 1.25, and said polyanionic compound is chosen from the group consisting of citric acid and $Na^+$, $K^+$, $Ca^{2+}$ or $Mg^{2+}$ salts thereof.

* * * * *

UNITED STATES PATENT AND TRADEMARK OFFICE
CERTIFICATE OF CORRECTION

PATENT NO. : 9,700,599 B2  
APPLICATION NO. : 14/079516  
DATED : July 11, 2017  
INVENTOR(S) : Soula et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 338 days.

Signed and Sealed this  
Twenty-fifth Day of September, 2018

Andrei Iancu  
*Director of the United States Patent and Trademark Office*

UNITED STATES PATENT AND TRADEMARK OFFICE
CERTIFICATE OF CORRECTION

Page 1 of 1

| | |
|---|---|
| PATENT NO. | : 9,700,599 B2 |
| APPLICATION NO. | : 14/079516 |
| DATED | : July 11, 2017 |
| INVENTOR(S) | : Soula et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this
Seventh Day of February, 2023

Katherine Kelly Vidal
*Director of the United States Patent and Trademark Office*